United States Patent
Farmer

(10) Patent No.: US 12,343,174 B2
(45) Date of Patent: Jul. 1, 2025

(54) METHODS AND APPARATUS FOR REMOVING ARTIFACTS FROM AN ELECTRORETINOGRAM

(71) Applicant: Diagnosys LLC, Lowell, MA (US)

(72) Inventor: Jeffrey D. Farmer, Chelmsford, MA (US)

(73) Assignee: Diagnosys LLC, Lowell, MA (US)

( * ) Notice: Subject to any disclaimer, the term of this patent is extended or adjusted under 35 U.S.C. 154(b) by 920 days.

(21) Appl. No.: 17/509,818

(22) Filed: Oct. 25, 2021

(65) Prior Publication Data

US 2022/0125383 A1  Apr. 28, 2022

Related U.S. Application Data

(60) Provisional application No. 63/104,639, filed on Oct. 23, 2020.

(51) Int. Cl.
*G11C 11/16* (2006.01)
*A61B 5/00* (2006.01)
(Continued)

(52) U.S. Cl.
CPC ............ *A61B 5/7203* (2013.01); *A61B 5/297* (2021.01); *A61B 5/398* (2021.01); *A61B 5/7225* (2013.01)

(58) Field of Classification Search
CPC ........ H10N 50/01; H10N 50/10; H10N 50/85; H10B 61/00; G11C 11/161; H01F 10/329
See application file for complete search history.

(56) References Cited

U.S. PATENT DOCUMENTS 10,426,399 B1   10/2019  Kayyali et al.
2011/0164218 A1   7/2011  Ornberg et al.
(Continued)

FOREIGN PATENT DOCUMENTS

WO   WO 2008/067052   6/2008

OTHER PUBLICATIONS

The International Society for Clinical Electrophysiology of Vision (ISCEV), Standards, Guidelines and Extended Protocols, https://iscev.wildapricot.org/standards.
(Continued)

*Primary Examiner* — Jack Dinh
(74) *Attorney, Agent, or Firm* — Pandiscio & Pandiscio

(57) ABSTRACT

A method for removing artifacts from an electroretinogram, the method comprising: visually stimulating at least one eye of a test subject, and using at least two electrodes to measure electrical responses from the at least one eye of the test subject; recording the electrical responses during, and for a predetermined period of time after, the time at which a visual stimulation is applied, whereby to generate a data set, wherein each electrical response is represented as a sweep comprising a plurality of voltage amplitude values and a plurality of corresponding time values; applying an elevated high pass filter to each sweep, wherein the elevated high pass filter is configured to remove any signal components with a frequency value of <1 hz; and plotting the resulting data set as an electroretinogram, in which the plurality of voltage amplitude values of the remaining signal is plotted on a first axis of an electroretinogram, and the plurality of corresponding time values of the remaining signal is plotted on a second axis of the electroretinogram.

22 Claims, 46 Drawing Sheets

Schematic of subject setup, electrodes, and electronics for providing Flash stimulus to a subject and recording the ERG signal

(51) Int. Cl.
  *A61B 5/297*   (2021.01)
  *A61B 5/398*   (2021.01)
  *H01F 10/32*   (2006.01)
  *H10B 61/00*   (2023.01)
  *H10N 50/01*   (2023.01)
  *H10N 50/10*   (2023.01)
  *H10N 50/85*   (2023.01)

(56) References Cited

U.S. PATENT DOCUMENTS

| | | |
|---|---|---|
| 2012/0200859 A1 | 8/2012 | Breitenstein et al. |
| 2015/0105689 A1 | 4/2015 | Miller |
| 2020/0029851 A1 | 1/2020 | Siwott |
| 2020/0237861 A1 | 7/2020 | Hageman et al. |

OTHER PUBLICATIONS

Frishman et al., ISCEV Extended Protocol for the Photopic Negative Response (PhNR) of the Full-Field Electroretinogram, Doc Ophthalmol, May 2018, vol. 136, pp. 207-211.

Viswanathan et al., The Photopic Negative Response of the Flash Electroretinogram in Primary Open Angle Glaucoma, Investive Ophthalmology & Visual Science, Feb. 2001, vol. 32, No. 2, pp. 514-522.

Schematic of subject setup, electrodes, and electronics for providing Pattern stimulus to a subject and recording the ERG signal Schematic of subject setup, electrodes, and electronics for providing Flash stimulus to a subject and recording the ERG signal

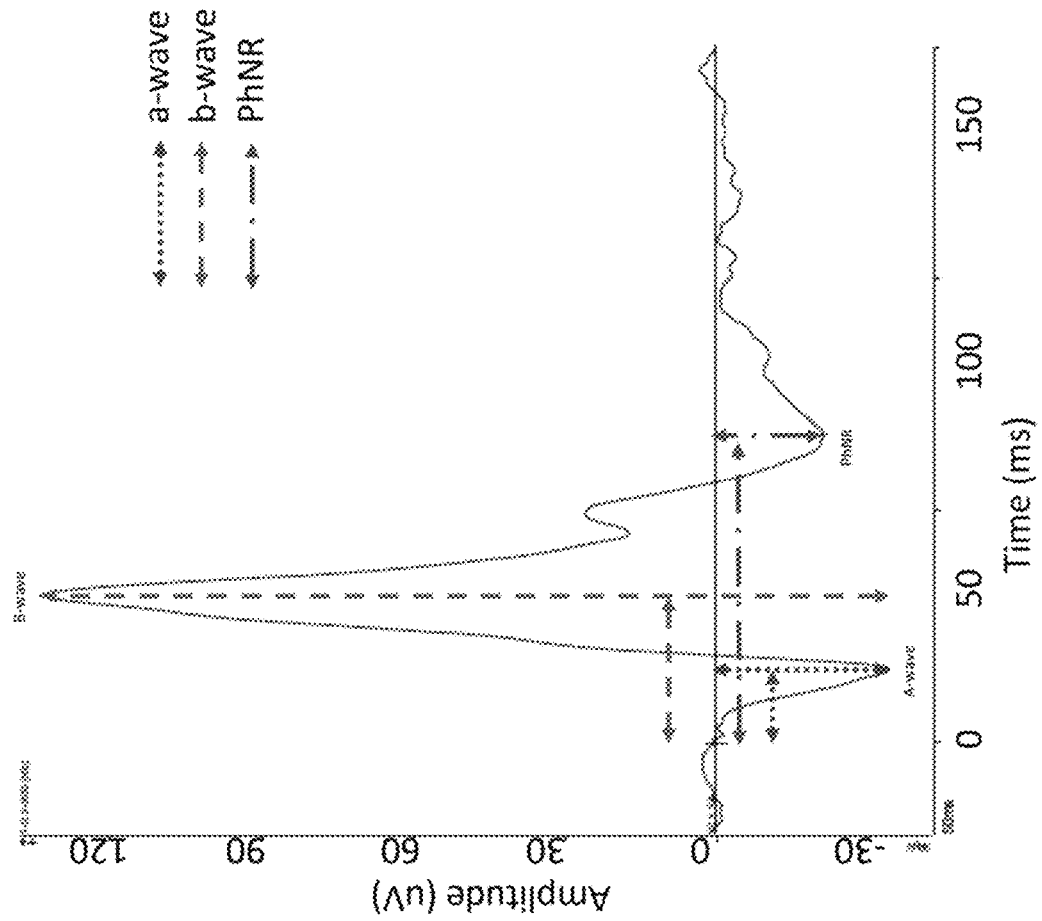

Typical ERG response for a PhNR test

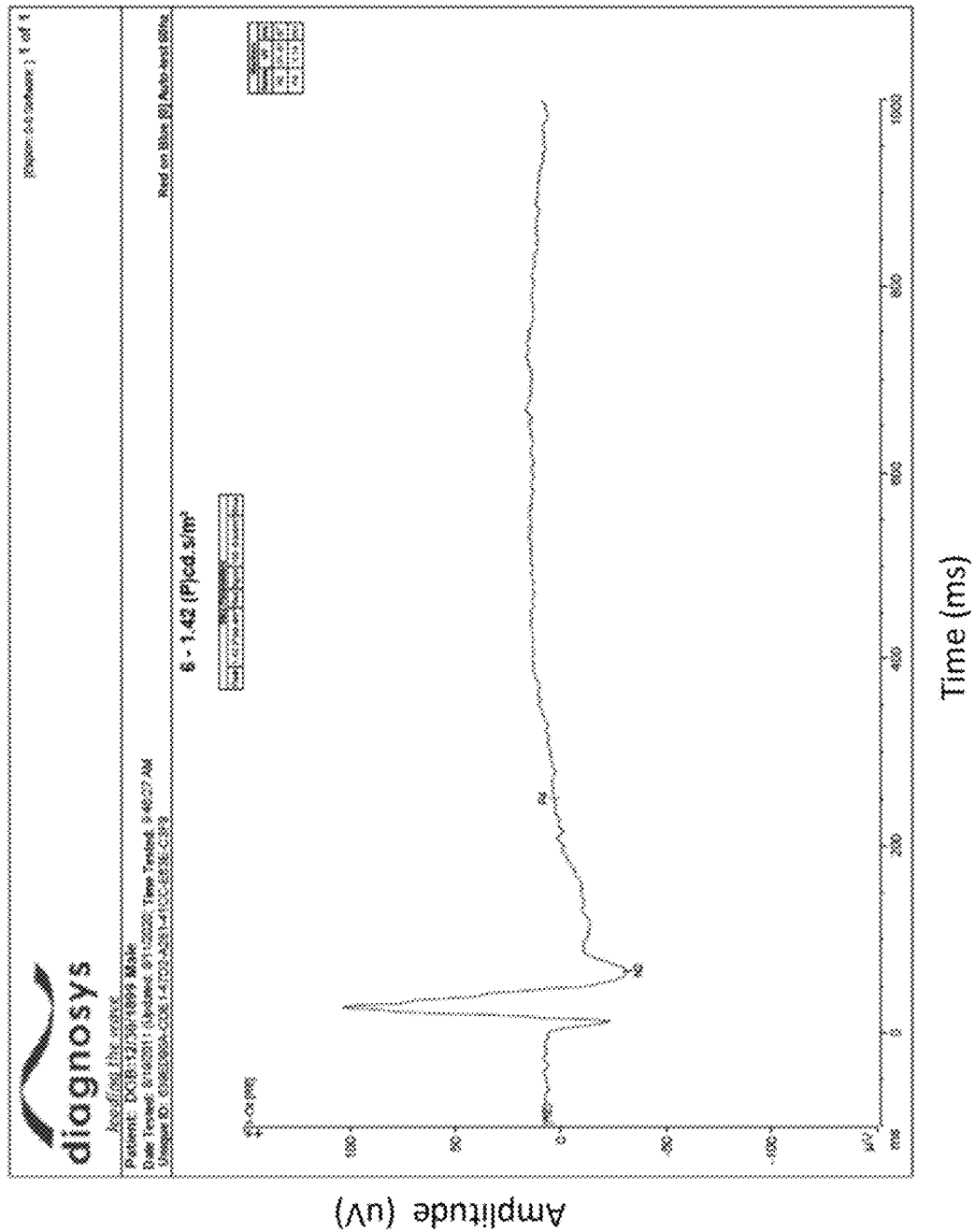
FIG. 4a PhNR response from non-human primate, with little to no muscle artifacts PhNR response from non-human primate, with little to no muscle artifacts PhNR response from a human subject, with little to no muscle artifacts

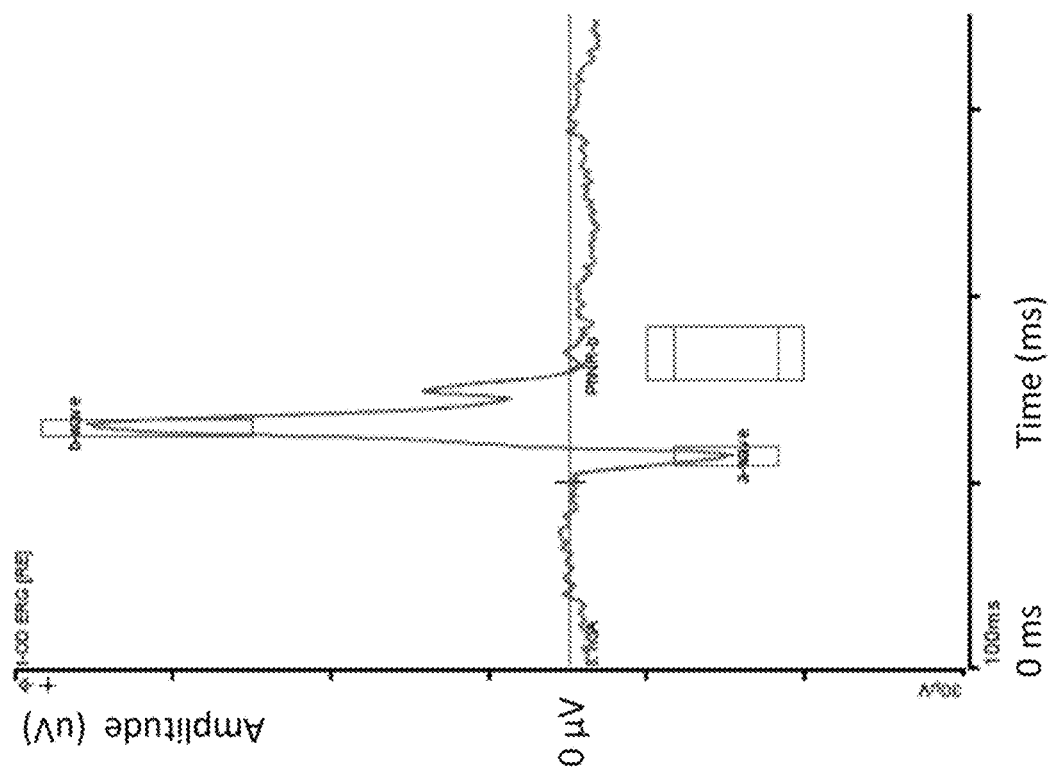

Example PhNR recording with ISCEV standard filtering applied: 0.3 to 300 hz

Example PhNR recording with the following level of EHPF applied: 0.5 to 300 hz

Example PhNR recording with the following level of EHPF applied: 1.0 to 300 hz

Example PhNR recording with the following level of EHPF applied: 2.5 to 300 hz

Example PhNR recording with the following level of EHPF applied: 5 to 300 hz

Example PhNR recording with the following level of EHPF applied: 7.5 to 300 hz

Example PhNR recording with the following level of EHPF applied: 10 to 300 hz

Example PhNR recording with the following level of EHPF applied: 15 to 300 hz

Example PhNR recording with ISCEV standard filtering applied: 0.3 to 300 hz

Example PhNR recording with the following level of EHPF applied: 0.5 to 300 hz

Example PhNR recording with the following level of EHPF applied: 1.0 to 300 hz

Example PhNR recording with the following level of EHPF applied: 2.5 to 300 hz

Example PhNR recording with the following level of EHPF applied: 5 to 300 hz

Example PhNR recording with the following level of EHPF applied: 7.5 to 300 hz

Example PhNR recording with the following level of EHPF applied: 10 to 300 hz

Example PhNR recording with the following level of EHPF applied: 15 to 300 hz

Example PhNR recording on a glaucoma patient, with EHPF applied at 7.5 hz, using the Fourier filter method Example PhNR recording on a glaucoma patient, with EHPF applied at 7.5 hz, using the Fourier filter method PhNR recording with significant eye twitch contributions; initial data PhNR recording with significant eye twitch contributions; initial data PhNR recording with significant eye twitch contributions; applying example PSF #1

PhNR recording with significant eye twitch contributions; after applying example PSF #1

Example PSF #1 (130) used in conjunction with a blink rejection filter

Example PSF #1 (130) used without a blink rejection filter

Example PSF #2 (140) used in conjunction with a blink rejection filter

Example PSF #2 (140) used without a blink rejection filter

Example PSF #3 (155) used in conjunction with a blink rejection filter

Example PSF #3 used without a blink rejection filter

Example PSF #4

Example PhNR luminance series test after applying an EHPF and PSF in combination

Schematic of subject setup, electrodes, camera and electronics for providing Pattern stimulus to a subject and recording the ERG signal, while monitoring for eye artifacts Schematic of subject setup, electrodes, camera and electronics for providing Flash stimulus to a subject and recording the ERG signal, while monitoring for eye artifacts

METHODS AND APPARATUS FOR REMOVING ARTIFACTS FROM AN ELECTRORETINOGRAM

REFERENCE TO PENDING PRIOR PATENT APPLICATION

This patent application claims benefit of prior U.S. Provisional Patent Application Ser. No. 63/104,639, filed Oct. 23, 2020 by Diagnosys LLC and Jeffrey D. Farmer for ERG ARTIFACT REMOVAL FILTER TECHNIQUES.

The above-identified patent application is hereby incorporated herein by reference.

FIELD OF THE INVENTION

This invention relates to novel methods and apparatus for performing electroretinography in general, and more particularly to novel methods and apparatus for removing artifacts from electroretinograms generated by performing electroretinography.

BACKGROUND OF THE INVENTION

Ophthalmic electrophysiology equipment, such as that manufactured and sold by Diagnosys LLC of Lowell, MA, is typically used for stimulating an eye of a test subject using flashes of light and/or moving patterns of light, and then measuring the resulting electrical response generated at the retina of the test subject and plotting the resulting electrical response so as to obtain a graphical representation of the amplitude of the electrical response versus the time period during stimulation (e.g., approximately 4 milliseconds), and for an arbitrary amount of time after the stimulation has been delivered to a test subject (e.g., approximately 150 milliseconds). This graphical representation is commonly referred to as an "electroretinogram" or a "retinogram". Such electrical stimulation and response monitoring is typically performed using electrodes that are applied on (or near) the eye of the test subject, and/or by using electrodes applied on (or near) the visual cortex of the test subject to measure the electrical response generated at the visual cortex, i.e., to obtain a visual evoked potential (VEP). Additional electrodes (sometimes referred to as "reference electrodes" and "ground electrodes") may be applied to other locations of the test subject's body in order to make electrical measurements that are important for performing the electroretinography test.

Ophthalmic electrophysiology is currently considered to be the only objective measure of visual function; all other ophthalmic diagnostics are either subjective measures of visual function, or a measure of anatomical structure.

There are a wide array of standard electroretinography (ERG) tests that may be performed, including full-field ERG, Pattern ERG, multi-focal ERG, focal ERG, etc. Similarly, a wide array of tests exist for testing the visual evoked potential (VEP) of a test subject, including pattern reversal VEP, pattern onset VEP and flash VEP.

With both ERG and VEP tests, the test is typically conducted by using multiple flashes of light and/or moving patterns of light, with a corresponding number of electrical response recordings (sometimes hereinafter referred to as "sweeps") being measured (i.e., using two or more electrodes to measure the differential signal between the two or more electrodes) over a selected period of time and recorded during the course of the test so as to produce an electroretinogram. An average of the individual electrical responses recorded (i.e., recordings) is then typically calculated and reported as a single test result.

After a number of individual recordings (i.e., sweeps) have been made, it is possible to choose which of the individual recordings (i.e., "sweeps") to include or exclude from the final average calculation which produces the single test result. Such a choice of which sweeps to include in the final average calculation may be done manually (e.g., by the clinician performing the test) or automatically (e.g., by a computer, according to a predetermined algorithm). Additionally, various filtering techniques may be applied to individual sweeps, groups of sweeps, or to all sweeps obtained when performing ERG on a test subject before the final average test result is calculated.

An exemplary system 5 for performing ERG on a subject is shown in FIGS. 1 and 2. Exemplary system 5 generally comprises an electrode array 10, a display 15 (e.g., a monitor, a flash stimulator, etc.), an amplifier 20 for amplifying electrical signals measured by the electrodes of electrode array 10, a controller 25 for controlling display 15 and/or the flash stimulator 15 and/or the electrodes of electrode array 10, and a computer 30 comprising appropriate software. More particularly, electrode array 10 typically comprises a right eye active electrode 35 for being placed near or contacting the right eye of the test subject, a right eye reference electrode 40 for contacting the test subject proximate to the subject's right eye, a left eye active electrode 45 for being placed near or contacting the left eye of the test subject, a left eye reference electrode 50 for contacting the test subject proximate to the subject's left eye, and a ground electrode 55 for contacting another part of the test subject's body. A system similar to system 5 is typically used for obtaining VEP recordings, except that with such a VEP system, an active electrode (not shown) attached to the scalp of the test subject above the area of the brain associated with the visual cortex is used instead of the active electrodes 35, 45 on the eyes of the test subject. It will be appreciated that various combinations of electrodes can be used for obtaining both ERG and VEP recordings, as will be apparent to one of ordinary skill in the art in view of the present disclosure. These are well described in international standards and publications and can be found at www.iscev.org, a website published by the international standards group called the International Society for Clinical Electrophysiology of Vision (ISCEV).

It should also be appreciated that, when using a monocular stimulator (i.e., a stimulator which only stimulates a single eye at any given time), the fellow eye (i.e., the eye not being stimulated at the same time as the stimulated eye) may be used as the reference. With such a monocular stimulator system, 3 electrodes are preferably used: one electrode near or contacting each eye of the test subject (i.e., one electrode serving as an active electrode and a second electrode serving as the reference electrode, and then vice versa when the stimulator is used to stimulate the fellow eye), and one electrode configured as a ground electrode.

The human test subject being tested is typically awake during the ERG (or VEP) test. The test subject is typically instructed to remain still during the test, and to look straight ahead at a fixation point. The goal of performing an ERG or VEP test is to record the electrical response of the retina of a test subject's eye and/or that of the visual pathway in a human brain ending at the test subject's visual cortex.

However, even the most relaxed test subject, fixating as well as possible on the fixation point, will often move in ways so as to produce undesirable "artifacts" during the test which are recorded by the system's electrodes/amplifier. As used herein, the term "artifacts" refers to any electrical signals recorded by the electrodes/amplifier which do not originate in the retina or visual pathway from the eye to the brain's visual cortex.

Many artifacts appearing in ERG and VEP test results are well understood, described in the literature and handled by existing ophthalmic electrophysiology systems. Such known artifacts include electrical noise resulting from other machines located in the area where the test is performed. These artifacts result from electrical signals which typically oscillate at the frequency of the electrical main power supply used in the region of the world where the test is being performed, typically 50 or 60 hz cyclical noise. Given the reasonably consistent frequency of this known artifact source, there are well-known ways to reject and/or filter out this artifact noise.

Another common artifact is generated by the test subject blinking their eye(s) during the test. A typical human test subject will blink their eye(s) about one time every 10 seconds. Thus, during a test that can last between 1 and 5 minutes, many blinks will occur and produce artifacts. The electrical signal generated by the test subject's blink is measured by the electrode/amplifier, and is typically quite large compared to even the largest ERG or VEP electrical signal. A blink causes an electrical artifact to be recorded by the electrode by physically moving the electrode relative to the test subject's eye, by recording the muscular electrical signals associated with the blink, or both. The recorded amplitude coming from a blink is usually 1 millivolt or larger. ERG and VEP signal amplitudes are typically in the range of 1 to 200 microvolts (μV), and usually no larger than 500 μV. A common way of rejecting signals that result from the test subject's blinks is to manually (or automatically) reject recorded sweeps with amplitudes larger than +/−1 millivolt (or similar levels depending on the specifics of the test).

Artifacts caused by small muscle contractions (e.g., "eye twitches") or involuntary physical responses to external stimuli (e.g., pupil dilation) generally result in electrical artifacts that are significantly smaller than artifacts due to "blinking" of the eye(s), and are therefore much more difficult to discern and remove from the resulting electroretinogram.

Given that many biological electrical artifacts emanate from the area around the eye of a test subject due to eye movements, pupillary movements, muscle contractions and the relatively close proximity of the ERG electrodes to those sources of artifacts, the ERG can be significantly affected by even small muscle artifacts.

ERG has historically been used primarily to measure the function of photoreceptor, bipolar and amacrine cells in the retina of the eye (and notably ERG has not typically been used to measure the function of the retinal ganglion cells, for reasons which will be discussed in further detail below). With most test subjects, these electrical signals (i.e., responses) occur within 50 milliseconds (ms) or less after the optical flash or pattern rotation stimulus of the ERG test is presented to the eye(s) of the test subject. Most muscle responses that generate electrical artifacts due to the optical stimulus will typically occur at 100 ms (or later) after the optical flash or pattern rotation stimulus has been presented to the eye(s) of the test subject. The fastest muscle responses recorded in a human test subject occurred at about 55 ms after the optical flash or pattern rotation has been presented to the eye(s) of the test subject. Given this fact, muscle-related artifacts have not generally been an issue for ERG recordings, since the delay between the stimulus and the onset time of the muscle response allows the muscle-related artifacts to be eliminated from the ERG recordings, or simply ignored. This is also because such muscle-related artifacts appear after (i.e., later in the trace) the non-ganglion cell retinal responses that have been measured.

Recently researchers and clinicians have developed versions of the ERG test that enable measurement of the ganglion cells in a retina. The ganglion cells are the third major step (after photoreceptor and bipolar cells) in the electrical cascade response of the retina to certain optical stimuli. The peak electrical response for the ganglion cells is in the range of 50 to 100 ms after the test subject's eye(s) is exposed to a flash stimuli, and most typically in the range of 60 to 80 ms after the subject's eye(s) is exposed to a flash stimuli. See, for example, FIGS. 3a and 3b, which show typical ERG responses obtained from photoreceptor cells (labeled as the "a-wave"), bipolar cells (labeled as the "b-wave"), and ganglion cells (labeled as the "PhNR"). FIG. 3a shows the standard way that time and amplitude of the a-wave, b-wave and PhNR peaks are measured from time 0 (when the flash stimuli occurs) and 0 amplitude. As with other ERG measurements, normal versus disease states are determined by the timing and amplitude (both positive or negative from 0) of these peaks. FIG. 3b shows an exemplary test report for an ERG configured as a PhNR test of both eyes at two stimulus frequencies.

Given that muscle reactions can occur within 55 ms after the test subject's eye is exposed to the optical stimuli, such muscle reactions are a source of artifacts in tests designed to measure the ganglion cell (sometimes hereinafter referred to as "PhNR") response. Typically, such muscle reaction artifacts result from very slight eye movements and/or eye twitches that occur randomly or in-phase with the optical stimuli (i.e., they are caused by, and at a relatively constant time after, the optical stimuli) and are measured by the electrodes, along with retinal response signals. The artifacts frequently overlap in time with the PhNR retinal response (which ranges from 50 to 100 ms after exposure to a flash stimuli). The presence of such artifacts in the resulting electroretinogram is a major confounding factor in correctly measuring the PhNR retinal response; it is not well recognized as an issue, and the problem of how to remove such artifacts from the electroretinogram has not previously been solved. Thus, it remains very difficult to accurately measure the retinal PhNR in the presence of these muscle reaction-related artifacts (or other similar artifacts).

The electrodes (e.g., the aforementioned electrodes 35, 40, 45, 50) and amplifier (e.g., the aforementioned amplifier 20) of an ERG system (e.g., the aforementioned system 5) are typically configured to record all electrical signals that are detected by the electrodes during a test, at all electrical resonant frequencies. Generally, some filtering of frequencies that are not of interest is performed during signal recording or in post-analysis of the resulting electroretinogram. Such analog filtering results in a data set in which targeted frequencies have been removed before the final electroretinogram is generated for clinical evaluation. Typically, and by international ISCEV standard, the ERG and VEP recordings are done with a bandpass filter set as wide as 0.3 to 300 hz (i.e., to remove data with frequencies that occur below 0.3 hz or above 300 hz), and as narrow as 1 to 100 hz (i.e., to remove data with frequencies that occur below 1 hz or above 100 hz). For example, the ISCEV international standard specifies the following bandpass filter for the standard ERG: "The system should record frequencies that include at least the range from 0.3 to 300 Hz". And the ISCEV international standard specifies the following bandpass filter for the standard VEP: "The recording frequency band of bandpass amplifiers should include the range from 1 to 100 Hz". Finally, the ISCEV international standard specifies the following bandpass filter for the standard PhNR test: "The low-frequency filter should be 0.3 Hz or lower; the high-frequency filter, a minimum of 300 Hz".

Typical response frequencies of the retina to an optical stimulus in the form of a flash, and those that tend to occur from muscle artifacts recorded by the ERG electrodes, overlap in their frequency ranges. Most of the electrical energy recorded from the retina is in the range of 1 to 100 hz frequency, with the majority of that energy in the range of 10 to 60 hz. Most of the electrical energy recorded from the eye muscle artifacts, such as eye twitches and slight eye movements, is in the range of 1 to 20 hz frequency, with the majority of that energy in the range of 1 to 10 hz.

Eye muscle artifacts create electrical signals that can appear very similar to retinal PhNR signals; such electrical signals can overlap in time and frequency space, and are a major confounding factor to conducting a successful PhNR measurement of retinal ganglion cell (RGC) function. In some cases, clinicians recognize the presence of eye muscle artifacts in a test and discard the test results altogether, resulting in wasted time by the patient, technician, and clinician, with no valid test being recorded. In other cases, the clinician does not recognize the presence of artifacts in a test, resulting in a strong possibility of an incorrect interpretation of PhNR and, in the worst case, an incorrect diagnosis of RGC disease or health. Except for very highly trained test subjects, these types of muscle artifacts are unavoidable during the test, even when the subject tries their very best to avoid generating them.

The correct timing and form of the PhNR response can be determined empirically using exemplary cases where no (or minimal) muscle artifacts occurred during the ERG test. By way of example but not limitation, studies have been conducted on monkeys who are tested while sedated under general anesthesia, and on highly trained/practiced humans. In both cases, little to no eye muscle artifacts occur during the ERG (including the PhNR) recording. FIGS. 4a, 4b, 5a and 5b show recordings derived from test subjects with minimal eye muscle artifacts and represent a "true waveform" response from a non-human primate retina (FIGS. 4a and 4b) and a human retina (FIGS. 5a and 5b). It will be appreciated that the "true waveform" responses for both classes of test subjects are very similar in their shape, amplitude and timing of peaks. The PhNR timing is measured from time=0 (i.e., when the flash stimuli occur) to the time of the PhNR peak (typically 60-80 ms after the subject's eye has been exposed to a stimulus). The PhNR amplitude is measured from a baseline of 0 volts down to the amplitude of the PhNR peak. A larger PhNR peak amplitude is generally associated with more RGC electrical activity and therefore with better retinal ganglion cell health. FIG. 4a (non-human primate) and FIG. 5a (human) are exemplary recordings from healthy retinas. Note that for purposes of plotting efficiency, the data appearing in FIG. 5a is presented in a tiled graph display where there is a common horizontal axis (i.e., for each of the 4 individual tests, and for the average of the 4 individual tests), while the vertical axis overlaps for the "average" plot versus the "individual tests" plot with each having their own zero point denoted as "0 μV". FIGS. 4b (non-human primate) and 5b (human) are recordings derived from retinas that have been damaged by the presence of glaucoma, a disease which kills RGCs and is represented by a lower amplitude PhNR response.

The foregoing empirically-derived test results form the basis for an objective measure to achieve the removal of the effect of muscle artifacts so as to produce a measurement primarily composed of retinal response in the PhNR amplitude which is devoid of unwanted artifacts in the recorded signal.

Since it is not practical to sedate human test subjects before performing ERG to obtain an accurate measurement of retinal response in the PhNR amplitude, and since restricting such a test only to highly-trained volunteers is medically undesirable, a need exists for novel methods and apparatus for reducing or eliminating muscle-based artifacts from ERG recordings while preserving signals representative of the retinal response of the test subject.

SUMMARY OF THE INVENTION

The present invention comprises the provision and use of novel methods and apparatus for reducing or eliminating muscle-based artifacts from ERG recordings while preserving signals representative of the retinal response of the test subject.

In one preferred form of the invention, there is provided a method for removing artifacts from an electroretinogram, the method comprising:
  visually stimulating at least one eye of a test subject, and using at least two electrodes to measure electrical responses from the at least one eye of the test subject;
  recording the electrical responses during, and for a predetermined period of time after, the time at which a visual stimulation is applied, whereby to generate a data set, wherein each electrical response is represented as a sweep comprising a plurality of voltage amplitude values and a plurality of corresponding time values;
  applying an elevated high pass filter to each sweep, wherein the elevated high pass filter is configured to remove any signal components with a frequency value of <1 hz; and
  plotting the resulting data set as an electroretinogram, in which the plurality of voltage amplitude values of the remaining signal is plotted on a first axis of an electroretinogram, and the plurality of corresponding time values of the remaining signal is plotted on a second axis of the electroretinogram.

In another preferred form of the invention, there is provided a system for removing artifacts from an electroretinogram, the system comprising:
  apparatus configured to visually stimulate at least one eye of a test subject, and using at least two electrodes to measure electrical responses from the at least one eye of the test subject;
  a processing unit configured to:
    record the electrical response during, and for a predetermined period of time after, the time at which a visual stimulation is applied, whereby to generate a data set, wherein each electrical response is represented as a sweep comprising a plurality of voltage amplitude values and a plurality of corresponding time values;
  apply an elevated high pass filter to each sweep, wherein the elevated high pass filter is configured to remove any signal components with a frequency value of <1 hz; and
  plot the resulting data set as an electroretinogram, in which the plurality of voltage amplitude values of the remaining signal is plotted on a first axis of a electroretinogram, and the plurality of corresponding time values of the remaining signal is plotted on a second axis of the electroretinogram.

In another preferred form of the invention, there is provided a method for removing artifacts from an electroretinogram, the method comprising:
  visually stimulating at least one eye of a test subject, and using at least two electrodes to measure electrical responses from the at least one eye of the test subject;
  recording the electrical responses during, and for a predetermined period of time after, the time at which one or more visual stimuli are applied, whereby to generate a data set, wherein each electrical response is represented as a sweep comprising a plurality of voltage amplitude values and a plurality of corresponding time values;
  plotting the voltage amplitude values of the data set on a first axis of an electroretinogram, and plotting the time values of the data set on a second axis of the electroretinogram, so as to produce a electroretinogram comprising a plurality of sweeps, wherein each sweep is defined to start at the time of a stimuli and generally represents a combination of signal components from (i) the electrical response of the retina of the at least one eye of the test subject to the visual stimulation, and (ii) an artifact;
  identifying a zone of the electroretinogram plot defined by a predetermined upper voltage amplitude limit, a predetermined lower voltage amplitude limit, a predetermined start time limit, and a predetermined end time limit, with at least one of the voltage amplitude limits being smaller than the largest voltage amplitude value representing a recorded electrical response of the retina;
  removing sweeps having voltage amplitude values that do not fall within the zone, whereby to produce a filtered electroretinogram depicting the sweeps not removed.

In another preferred form of the invention, there is provided a system for removing artifacts from an electroretinogram, the system comprising:
  apparatus configured to visually stimulate at least one eye of a test subject, and using at least two electrodes to measure electrical responses from the at least one eye of the test subject;
  a processing unit configured to:
    record the electrical responses during, and for a predetermined period of time after, the time at which one or more visual stimuli are applied, whereby to generate a data set, wherein each electrical response is represented as a sweep comprising a plurality of voltage amplitude values and a plurality of corresponding time values;
    plot the voltage amplitude values of the data set on a first axis of an electroretinogram, and plot the time values of the data set on a second axis of the electroretinogram, so as to produce a electroretinogram comprising a plurality of sweeps, wherein each sweep is defined to start at the time of a stimuli and generally represents a combination of signal components from (i) the electrical response of the retina of the at least one eye of the test subject to the visual stimulation, and (ii) an artifact;
    identify a zone of the electroretinogram plot defined by a predetermined upper voltage amplitude limit, a predetermined lower voltage amplitude limit, a predetermined start time limit, and a predetermined end time limit, with at least one of the voltage amplitude limits being smaller than the largest voltage amplitude value representing a recorded electrical response of the retina;
    remove sweeps having voltage amplitude values that do not fall within the zone, whereby to produce a filtered electroretinogram depicting the sweeps not removed.

In another preferred form of the invention, there is provided a method for removing artifacts from an electroretinogram, the method comprising:
  visually stimulating at least one eye of a test subject, and using at least two electrodes to measure electrical responses from the at least one eye of the test subject;
  recording the electrical responses during, and for a predetermined period of time after, the time at which one or more visual stimuli are applied, whereby to generate a data set, wherein each electrical response is represented as a sweep comprising a plurality of voltage amplitude values and a plurality of corresponding time values;
  plotting the voltage amplitude values of the data set on a first axis of an electroretinogram, and plotting the time values of the data set on a second axis of the electroretinogram, so as to produce a electroretinogram comprising a plurality of sweeps, wherein each sweep is defined to start at the time of a stimuli and generally represents a combination of signal components from (i) the electrical response of the retina of the at least one eye of the test subject to the visual stimulation, and (ii) an artifact;
  calculating an average voltage amplitude value for the plurality of sweeps for each time value;
  calculating the root mean square (RMS) difference between the voltage amplitude value of each sweep at each time value and the average voltage amplitude value for all of the plurality of sweeps for that time value;
  ranking the root mean square (RMS) difference of each sweep based on the difference between the calculated root mean square (RMS) difference of each sweep at each time value and the average voltage amplitude value for the plurality of the sweeps for that time value; and
  discarding those ranked sweeps that are ranked below a predetermined value relative to the remaining sweeps, whereby to produce an electroretinogram depicting the sweeps not discarded.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 3a and 3b show typical ERG responses obtained from photoreceptor, bipolar and ganglion cells after a test subject's eye is exposed to a flash stimuli;

FIGS. 4a, 4b, 5a and 5b show recordings derived from test subjects exhibiting minimal eye muscle artifacts;

FIGS. 17*a*, 17*b*, 18*a* and 18*b* show the benefits of test-to-test repeatability that result from using a Preferred Sweep Filter (PSF) formed in accordance with the present invention.

DETAILED DESCRIPTION OF THE PREFERRED EMBODIMENTS

The present invention comprises the provision and use of novel methods and apparatus for reducing or eliminating muscle-based artifacts from ERG recordings while preserving signals representative of the retinal response of the test subject.

More particularly, the present invention generally comprises two novel methods for reducing or eliminating muscle-based artifacts that can be used independently of one another, or in concert with one another, and which are intended to reduce or eliminate the effect of eye muscle artifacts in an ERG recording while leaving most, if not all, of the retinal response intact in the recording.

The first method according to the present invention uses an Elevated High Pass Filter (EHPF) to evaluate and improve the recorded signal in frequency space.

The second method according to the present invention uses a Preferred Sweep Filter (PSF) to evaluate and improve the recorded signal in time space.

Both the EHPF of the present invention and the PSF of the present invention may be used independently of one another, or in concert with one another, and both the EHPF and the PSF may be used while actively recording ERG data, or in post-analysis of ERG data. Both novel methods of the present invention will hereinafter be discussed in further detail below.

Elevated High Pass Filter (EHPF)

The EHPF of the present invention is configured to primarily remove the effects of muscle energy artifacts while leaving retinal energy recorded during an ERG/PhNR test. To remove the effects of muscle energy, various filter techniques may be utilized, including, but not limited to, analog filters such as a Bessel, Butterworth, Chebyshev or other similar filters of various orders which will be apparent to one of ordinary skill in the art in view of the present disclosure. In one preferred form of the present invention, these analog filter(s) are applied as a bandpass filter either during the active recording (i.e., to reject sweeps automatically if they do not meet a specified criteria set by the EHPF) or in post-analysis of the ERG recording after the test is concluded. The analog filter(s) may be applied in a single-pass filtering step or in a double-pass filtering step (which steps are generally common ways of applying bandpass filters). Additionally (or alternatively), if desired, a Fourier transform may be applied to the recorded signal to transform the recorded energy from voltage amplitude data versus time into a set of voltage magnitude data versus frequency, after which signal components at specific frequencies may be selected for removal. Finally, where the aforementioned Fourier method is employed, the signal is preferably recomposed and transformed back into voltage amplitude versus time in order to facilitate clinical evaluation, leaving only those frequencies selected in the bandpass filter.

Figure 1:
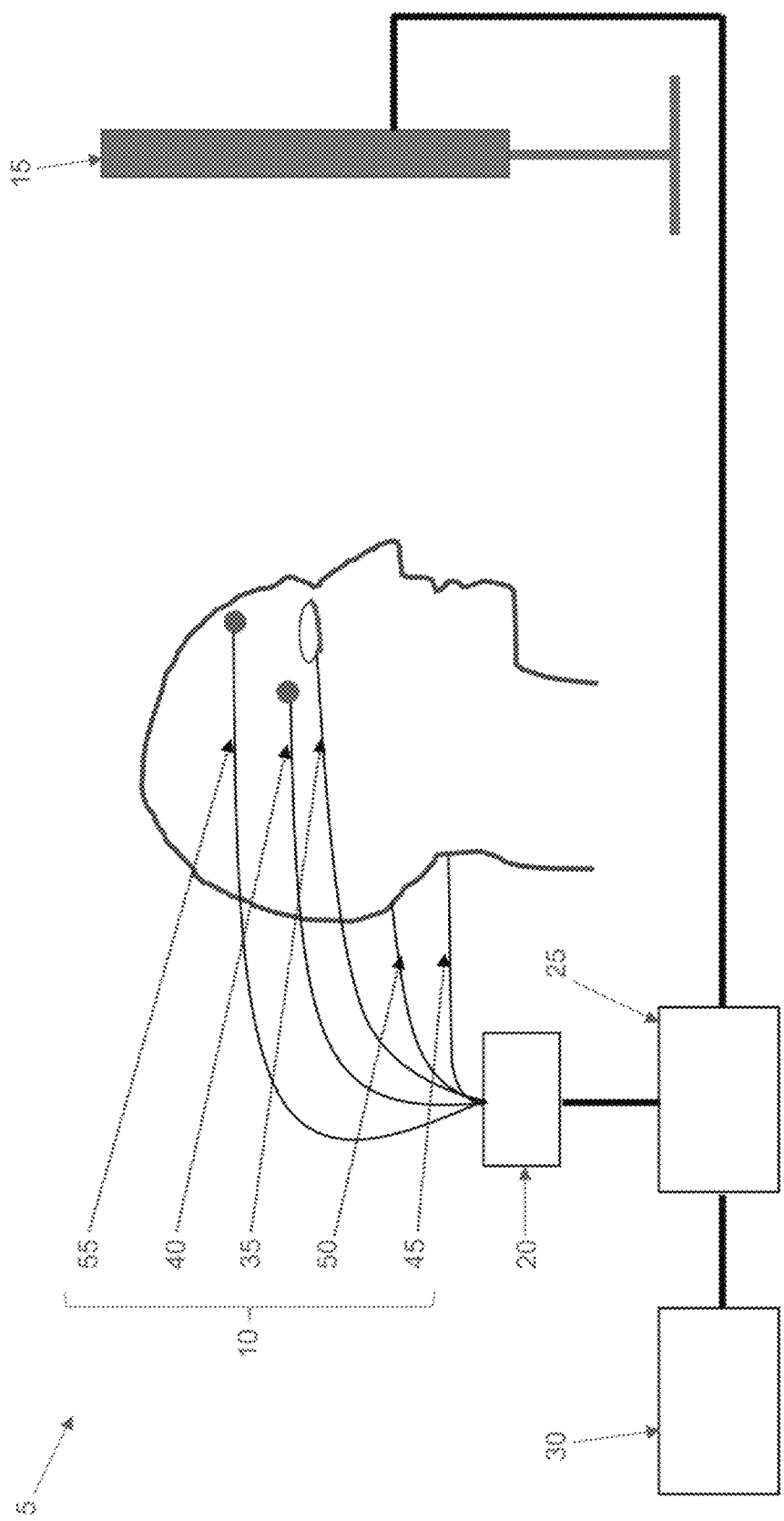
FIGS. 1 and 2 are schematic views showing an exemplary system for performing electroretinography (ERG) on a test subject.
Figure 2:
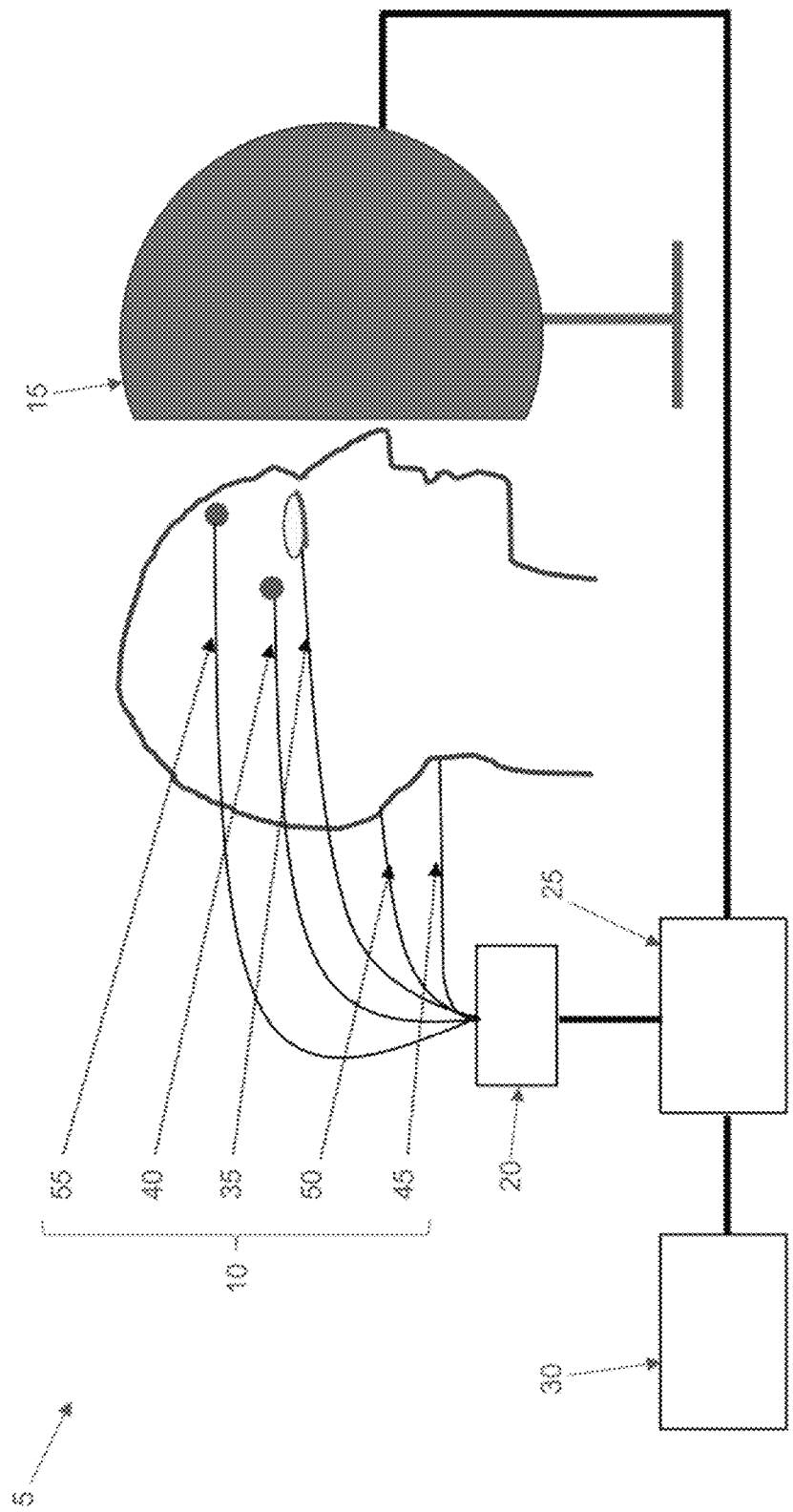
Figure 3B:
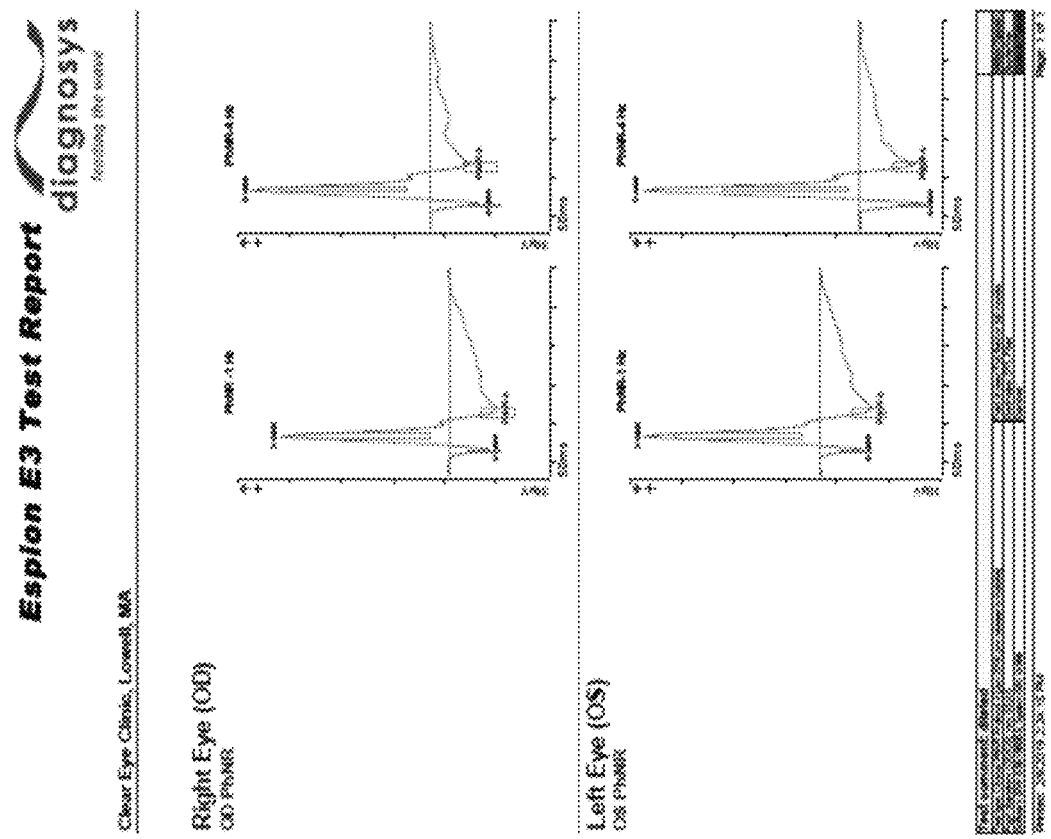
Figure 4B:
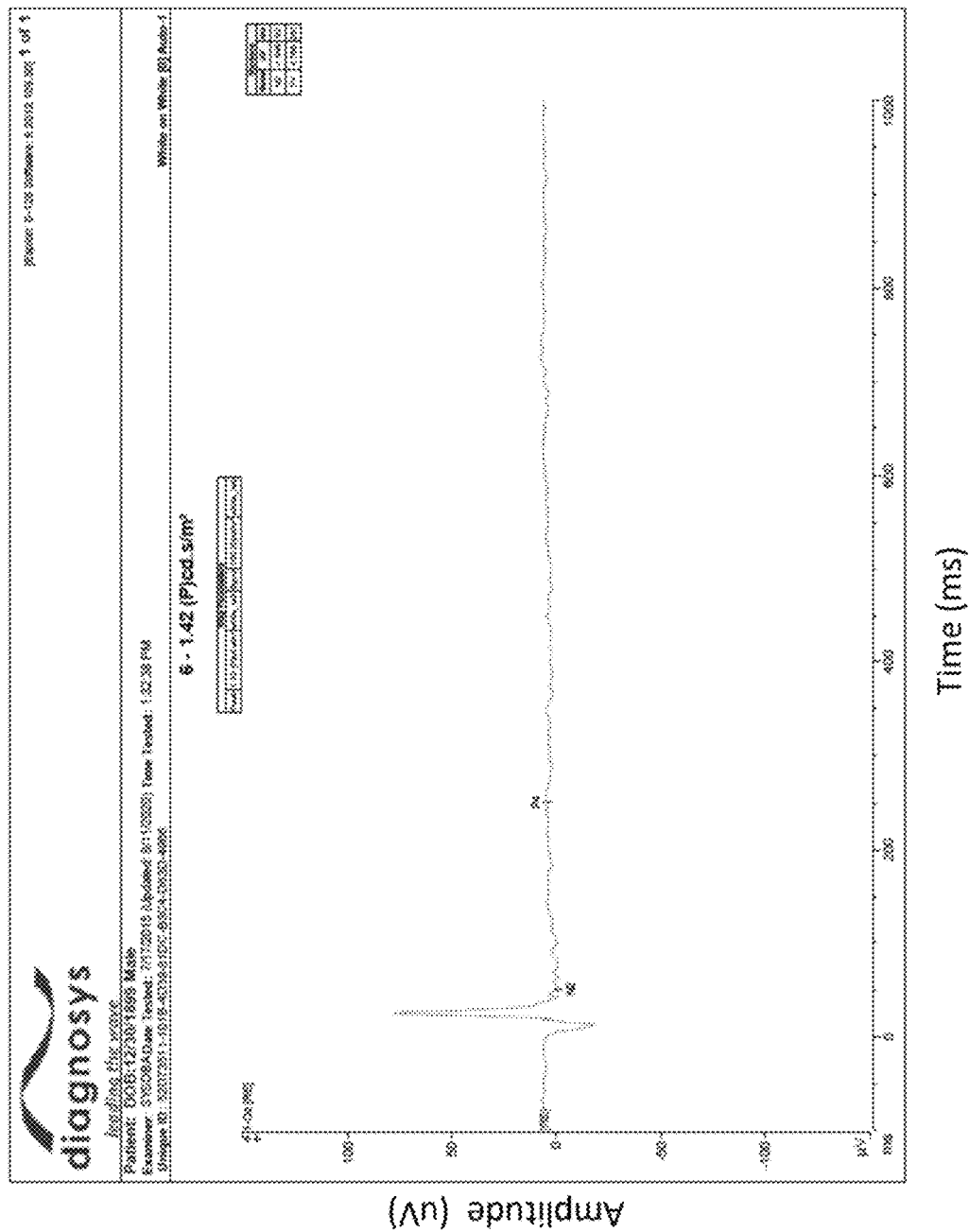
Figure 5A:
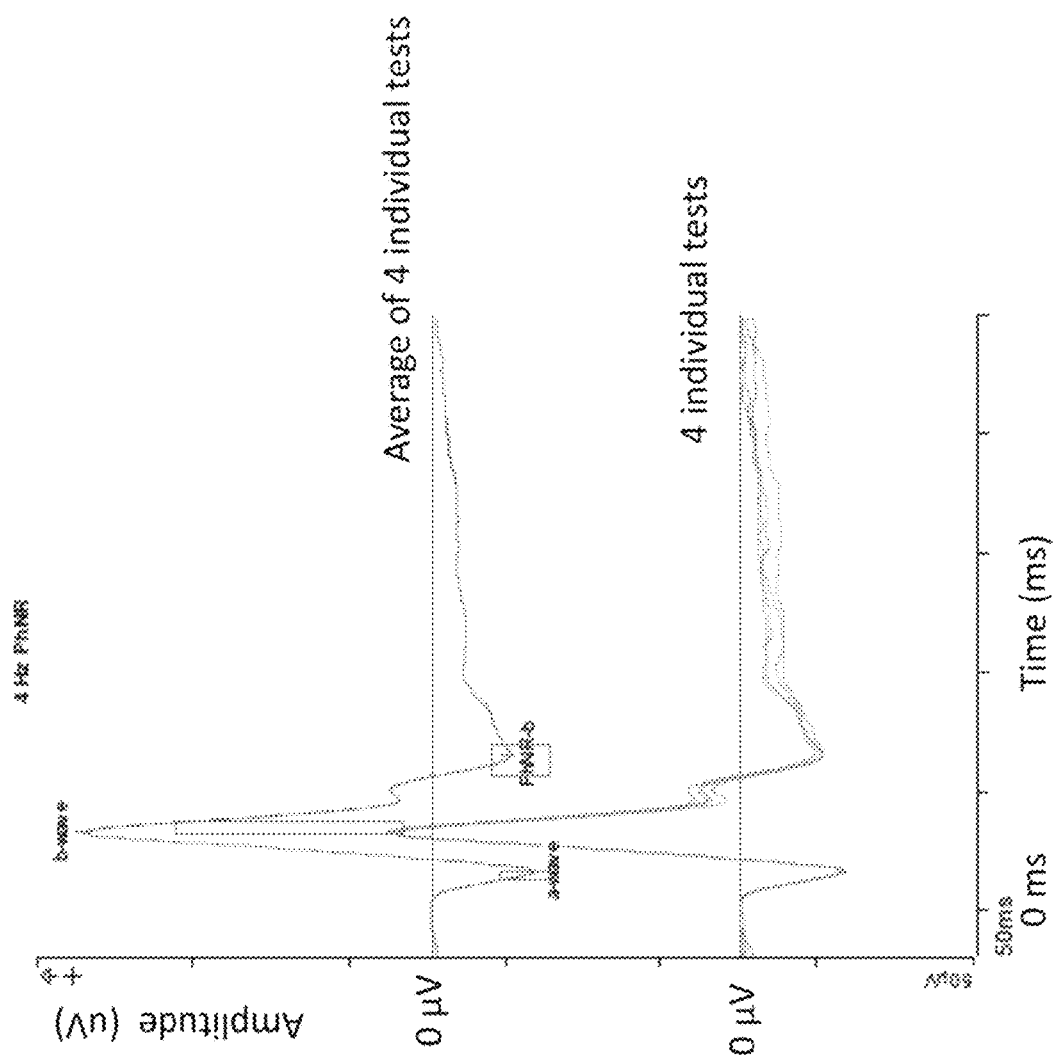

FIGS. 6*a*-6*h* and 7*a*-7*h* show the recordings resulting from two PhNR tests conducted on two human test subjects having normal retinas, but exhibiting significant eye muscle artifacts (e.g., slight eye movements and eye twitches) recorded during the test. In each of the recordings shown in FIGS. 6*a*-6*h* and 7*a*-7*h*, there are 4 individual test recordings at the bottom of each graph that were recorded in succession, and a test result at the top of each graph that represents the average of the 4 individual tests (i.e., FIGS. 6a-6h and 7a-7h use a tiled graphing scheme similar to that used in FIG. 5a discussed above).

Figure 6A:
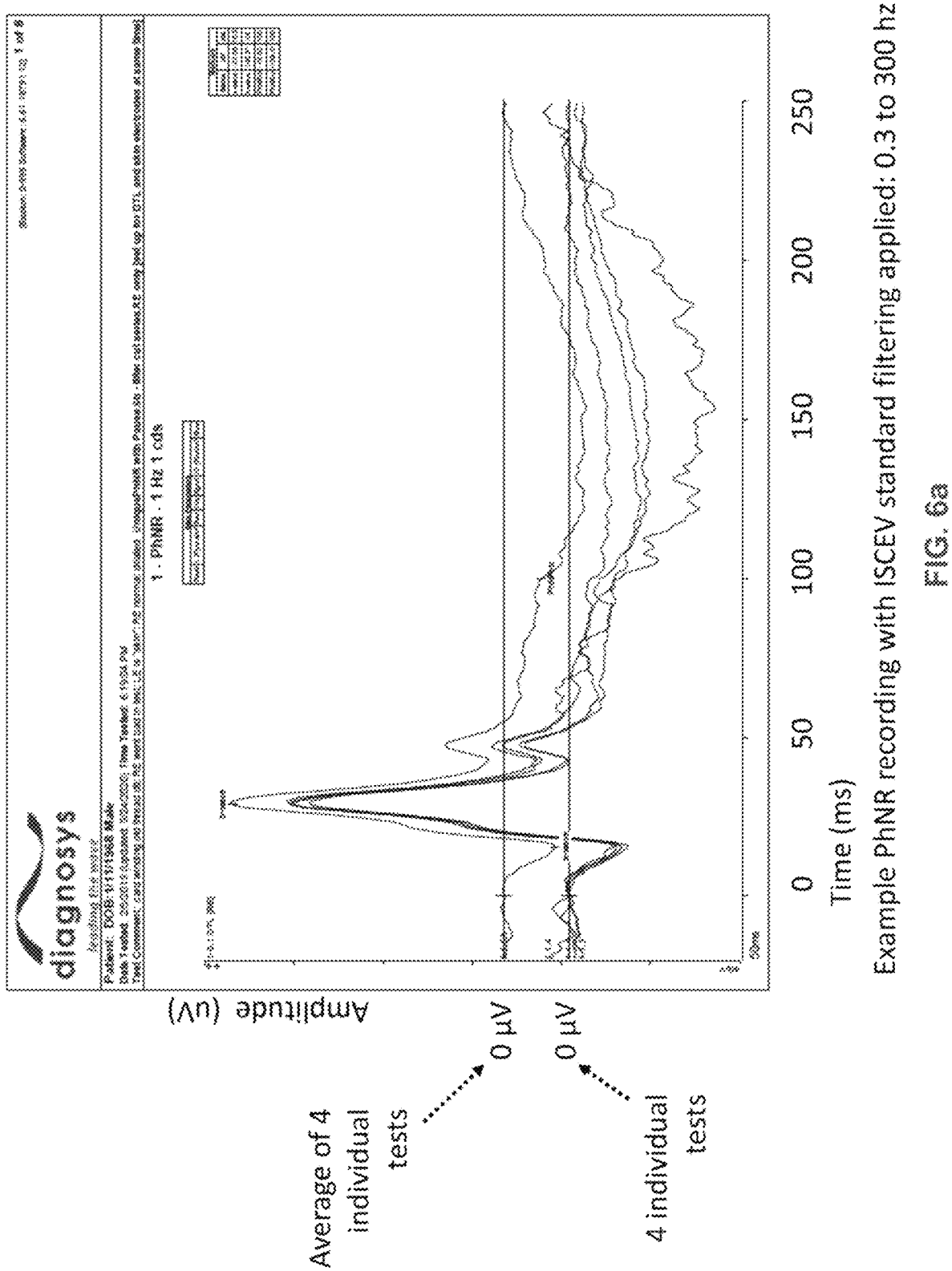
FIG. 6a shows a recording resulting from a PhNR test conducted on a human test subject having a healthy retina, but exhibiting significant eye muscle artifacts.
Figure 6B:
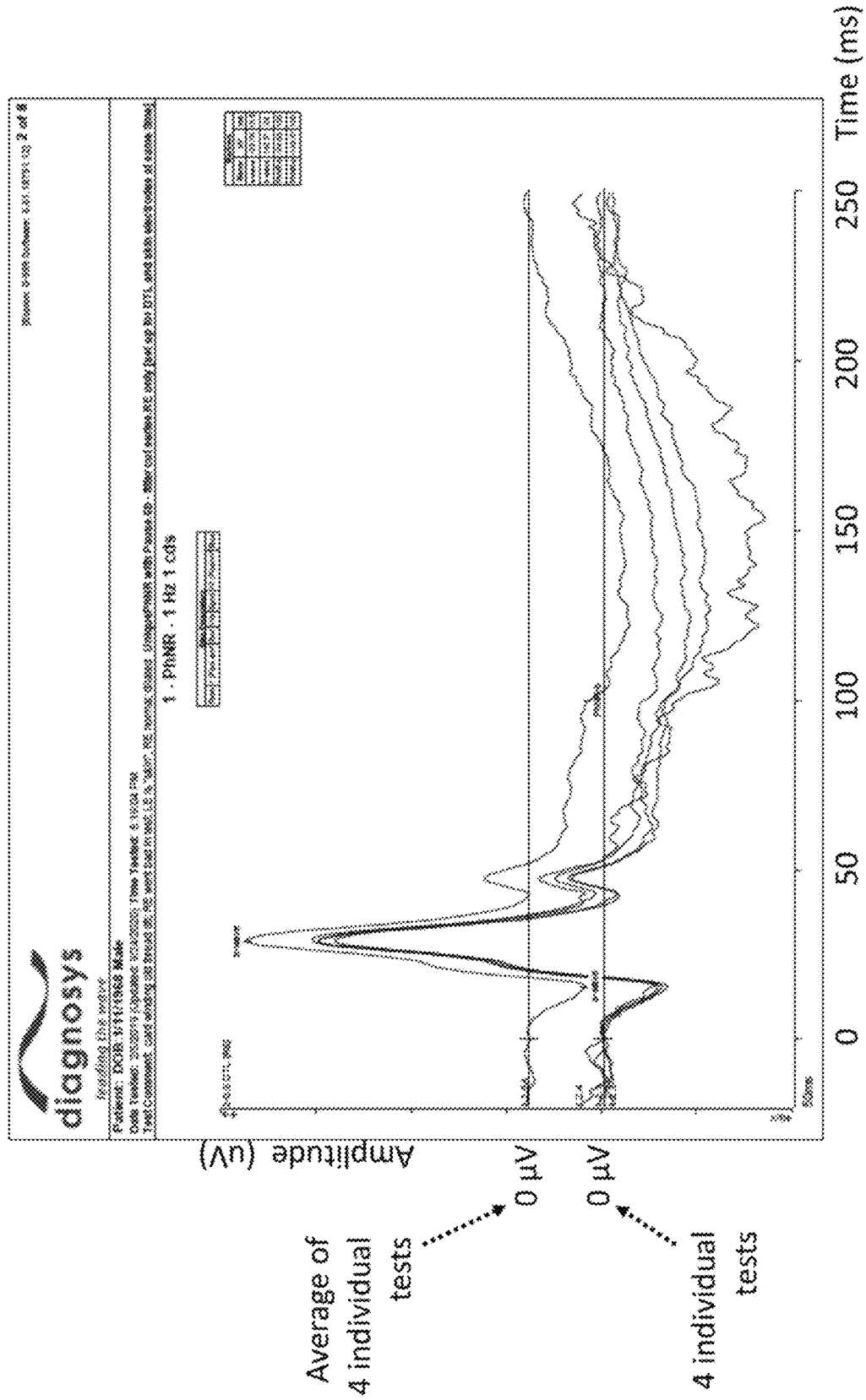
FIGS. 6*b*, 6*c*, 6*d*, 6*e*, 6*f*, 6*g* and 6*h* show the recording of FIG. 6*a* after an Elevated High Pass Filter (EHPF) formed in accordance with the present invention has been applied to the recording, with each figure showing the result of an EHPF having different parameters being applied to the recording of FIG. 6*a*.
Figure 6C:
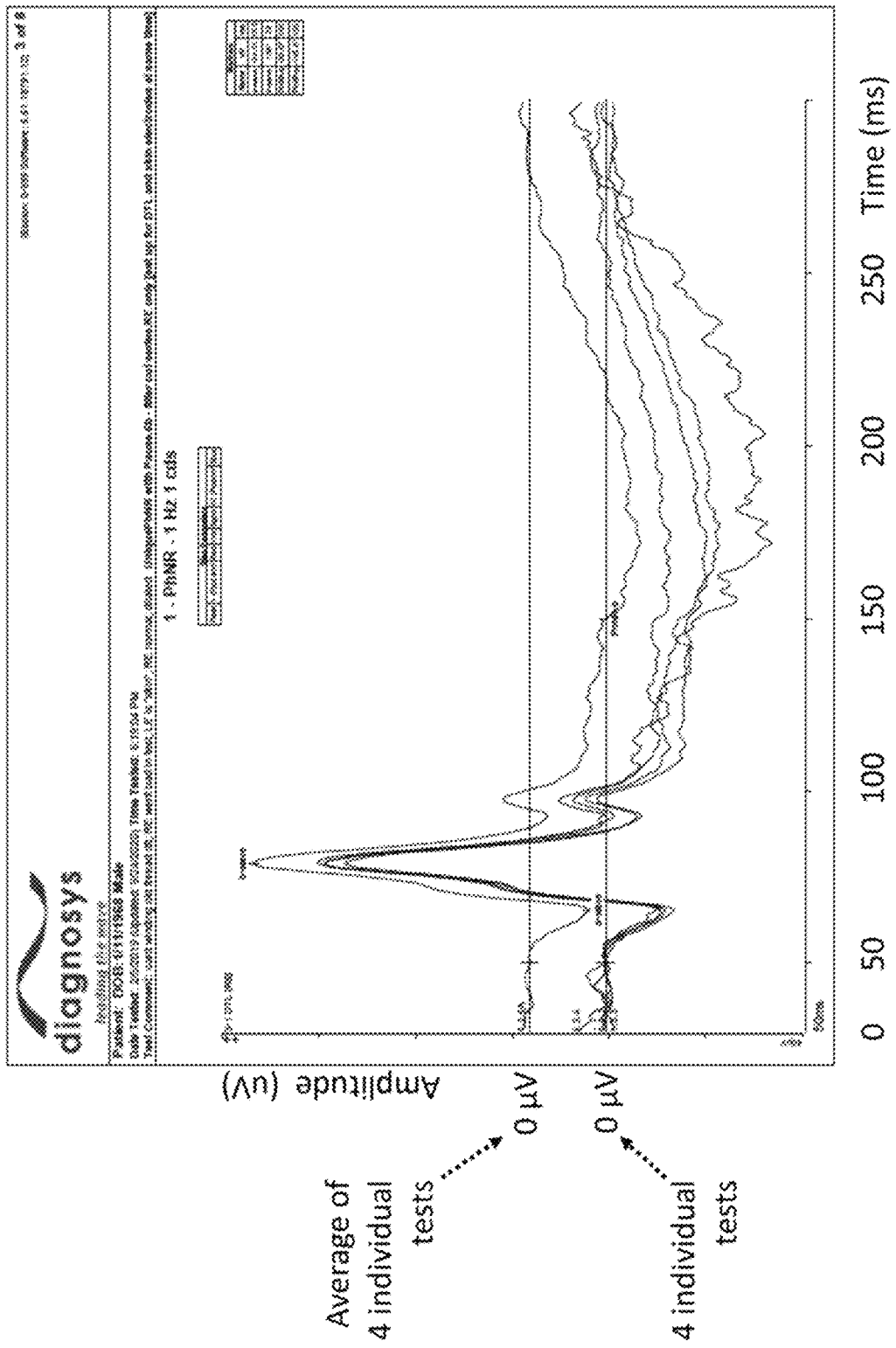
Figure 6D:
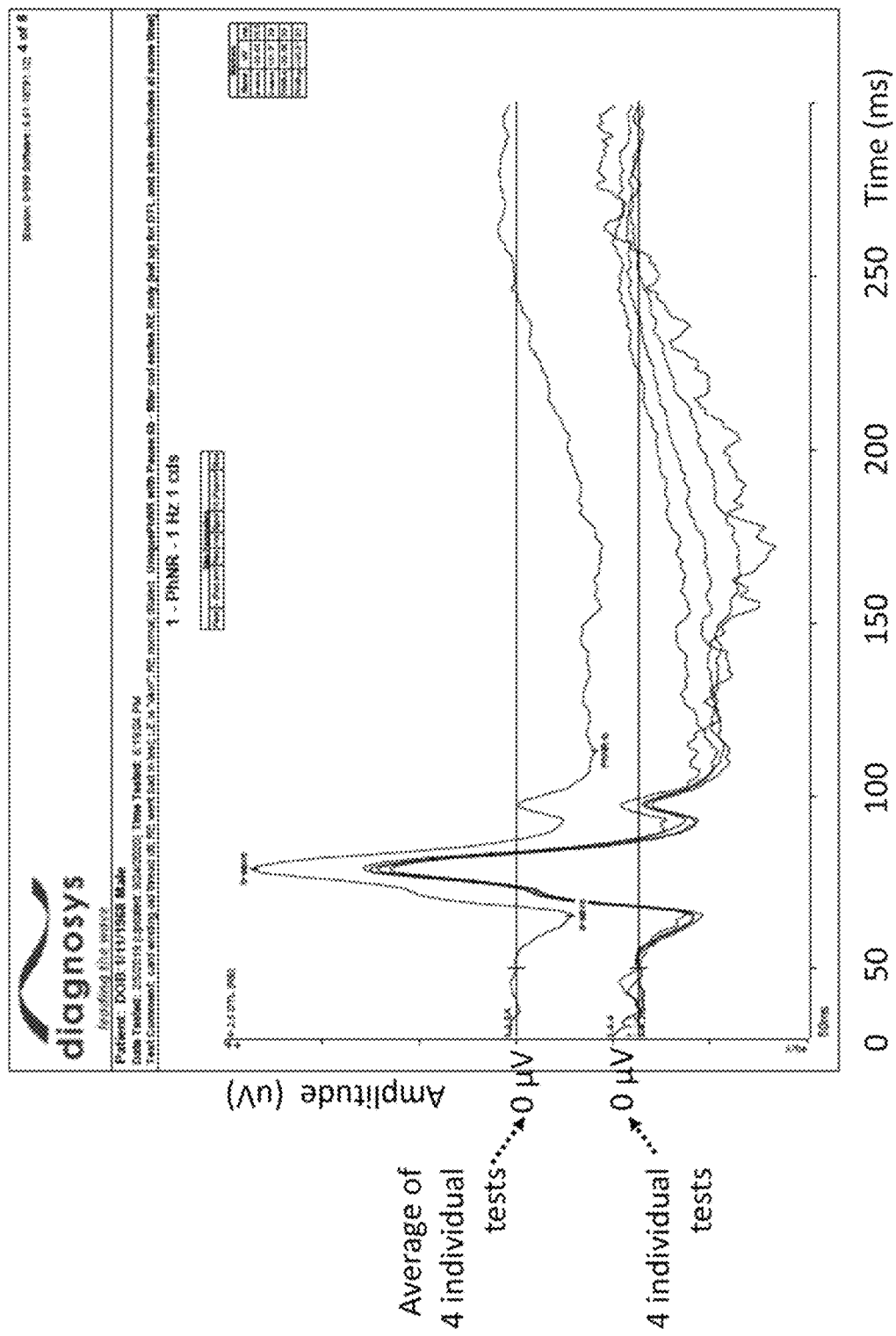
Figure 7A:
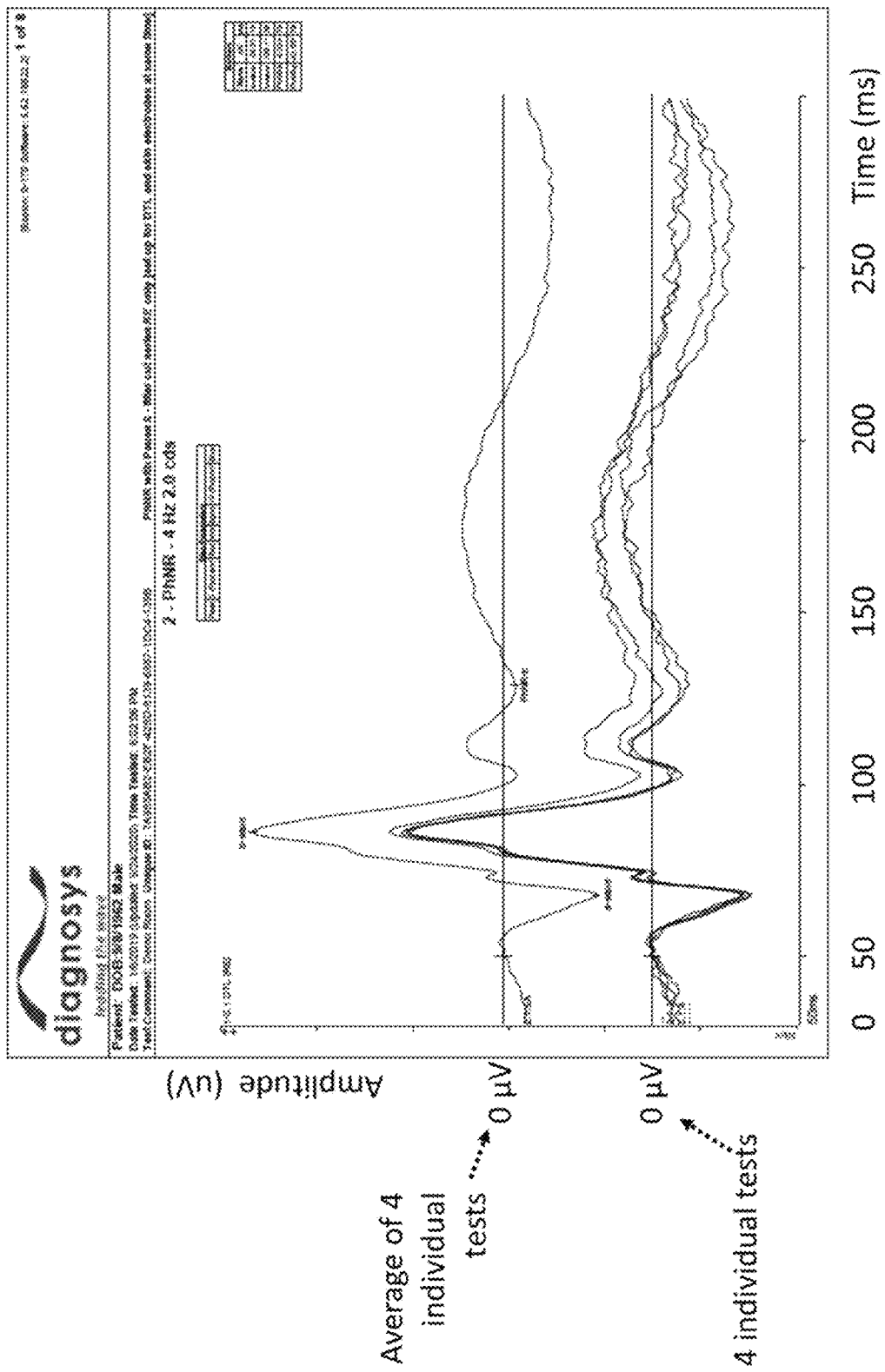
FIG. 7*a* shows another recording resulting from a PhNR test conducted on a human test subject having a healthy retina, but exhibiting significant eye muscle artifacts.
Figure 7B:
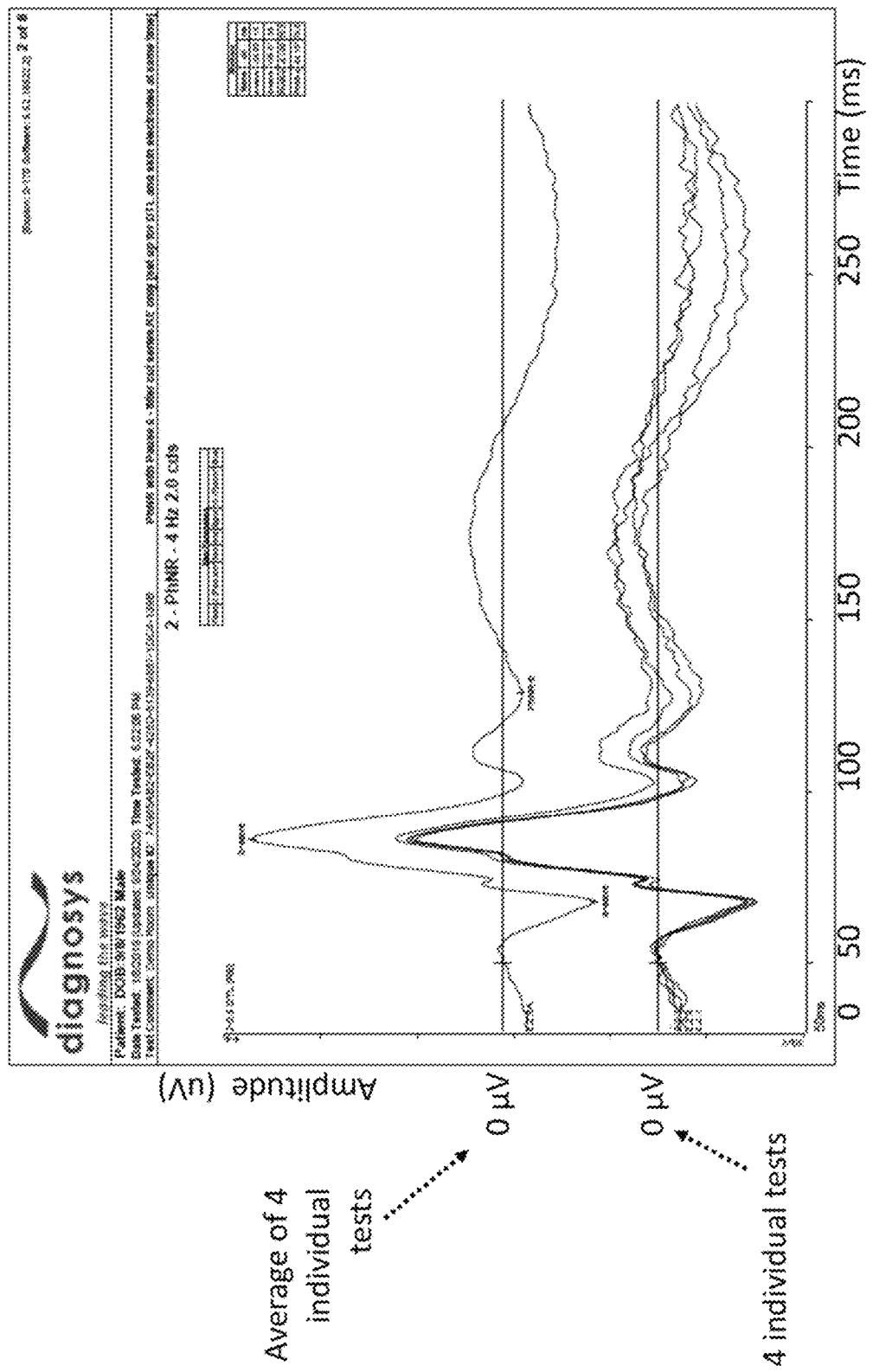
FIGS. 7*b*, 7*c*, 7*d*, 7*e*, 7*f*, 7*g* and 7*h* show the recording of FIG. 7*a* after an Elevated High Pass Filter (EHPF) formed in accordance with the present invention has been applied to the recording, with each figure showing the result of an EHPF having different parameters being applied to the recording of FIG. 7*a*.
Figure 7C:
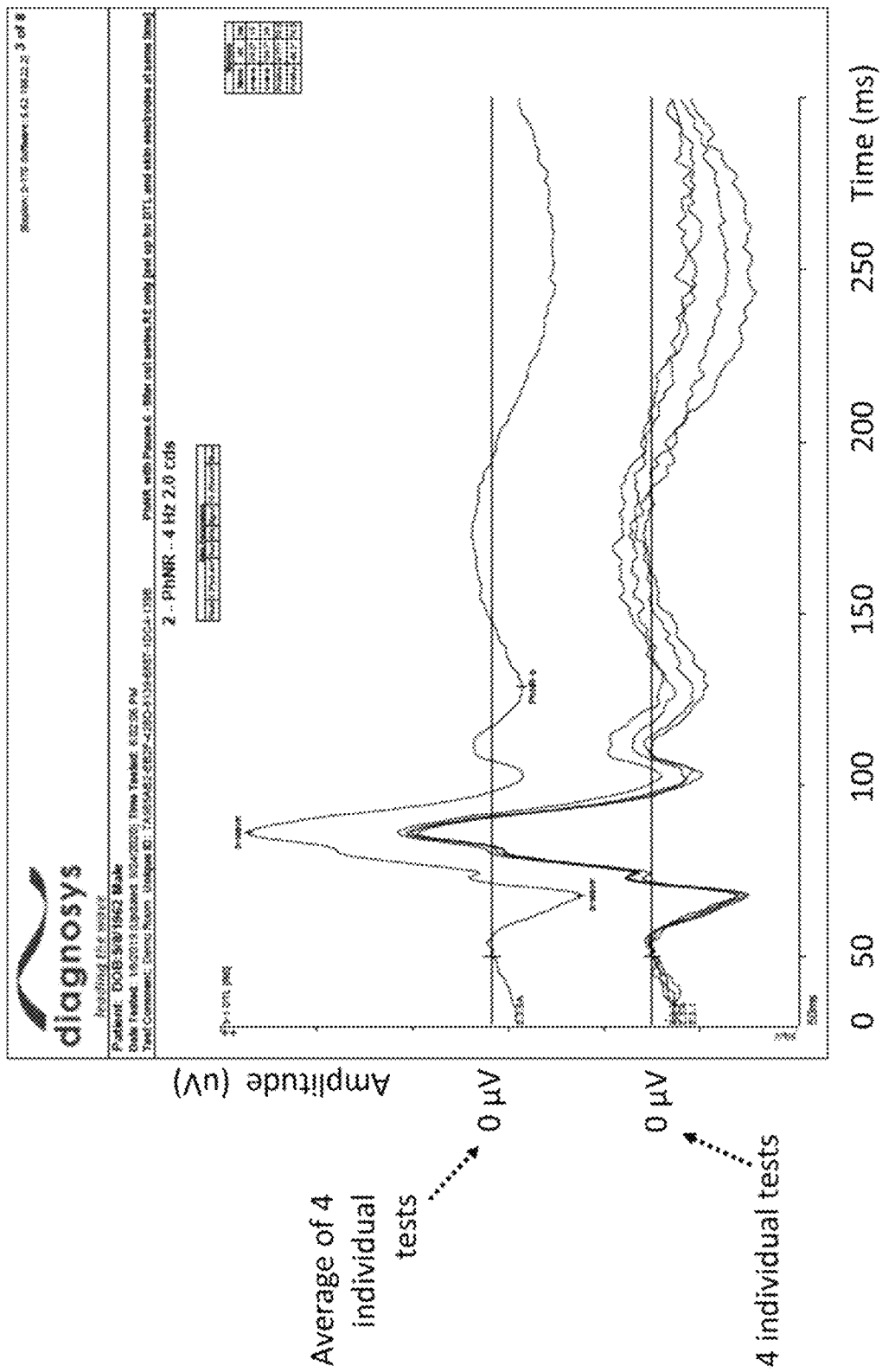
Figure 7D:
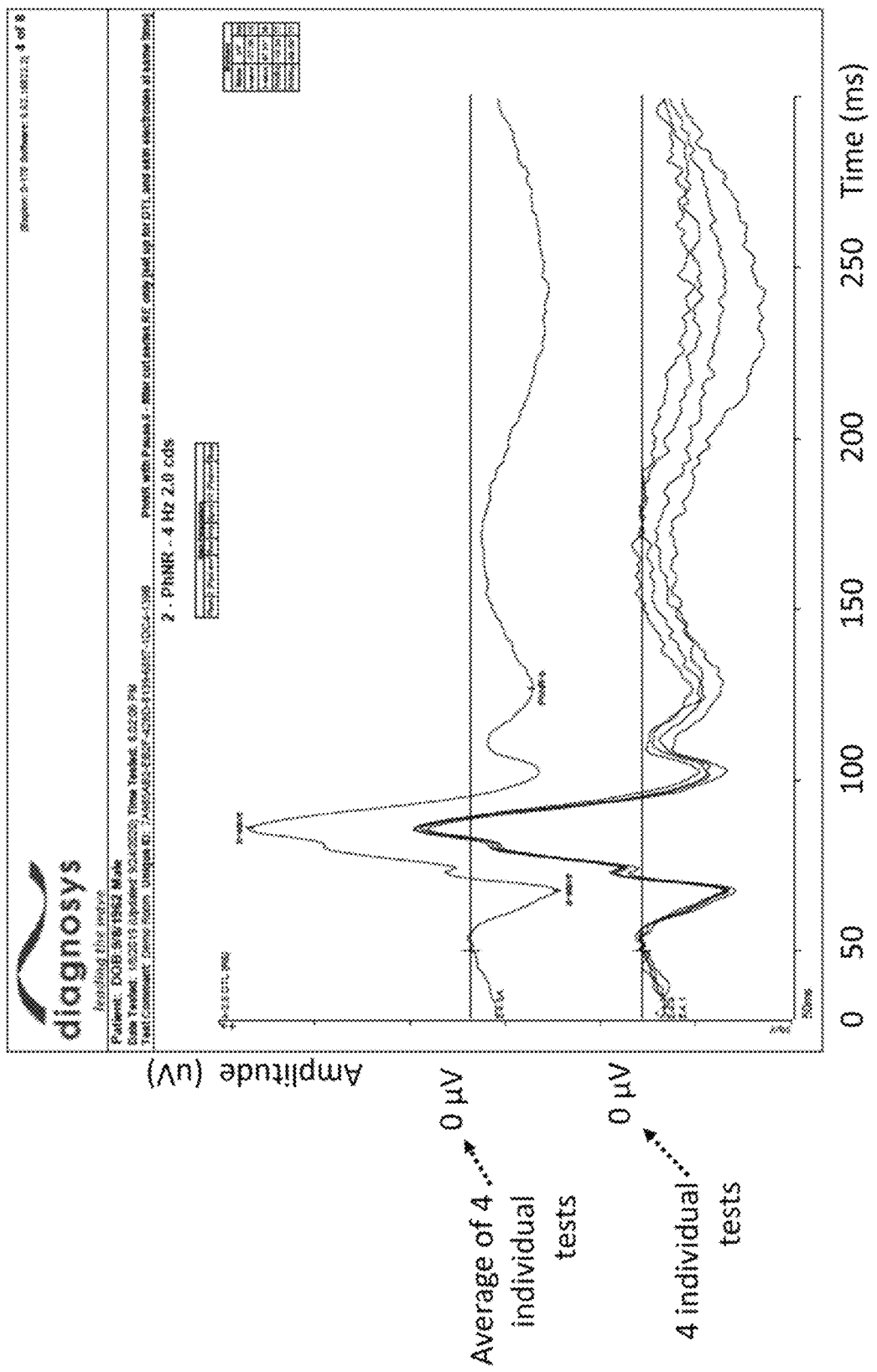
Figure 7E:
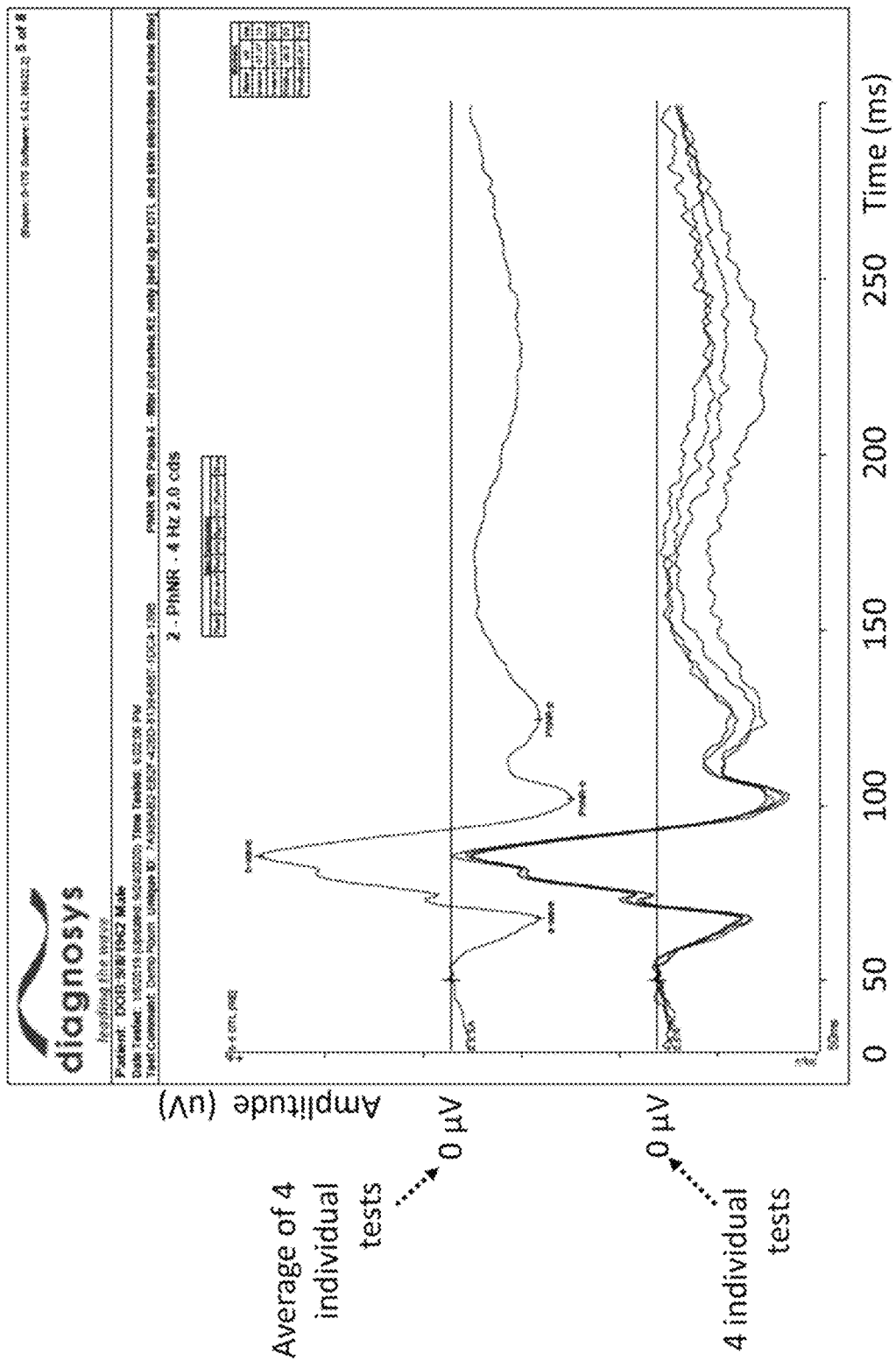
Figure 7F:
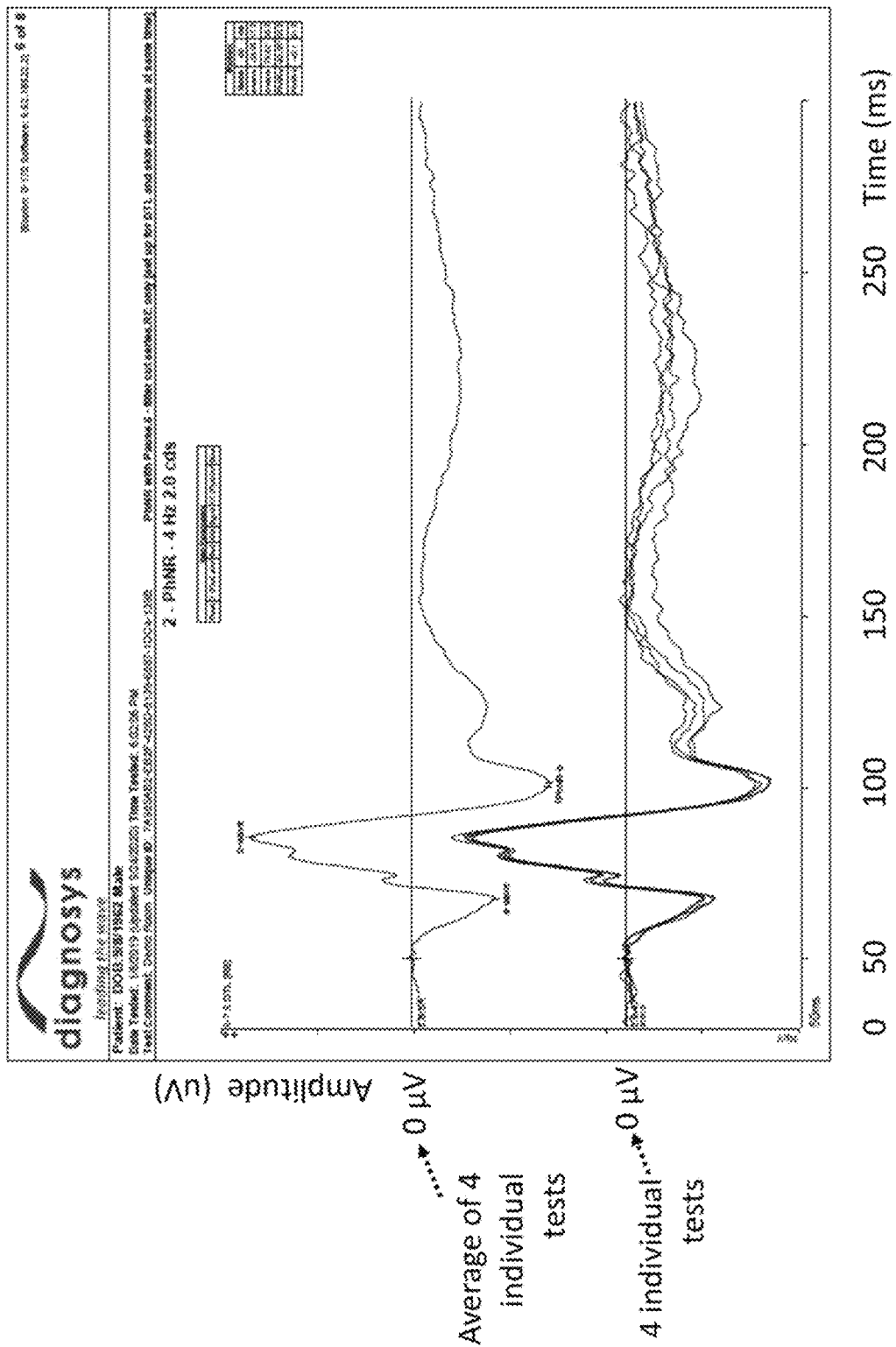
Figure 7G:
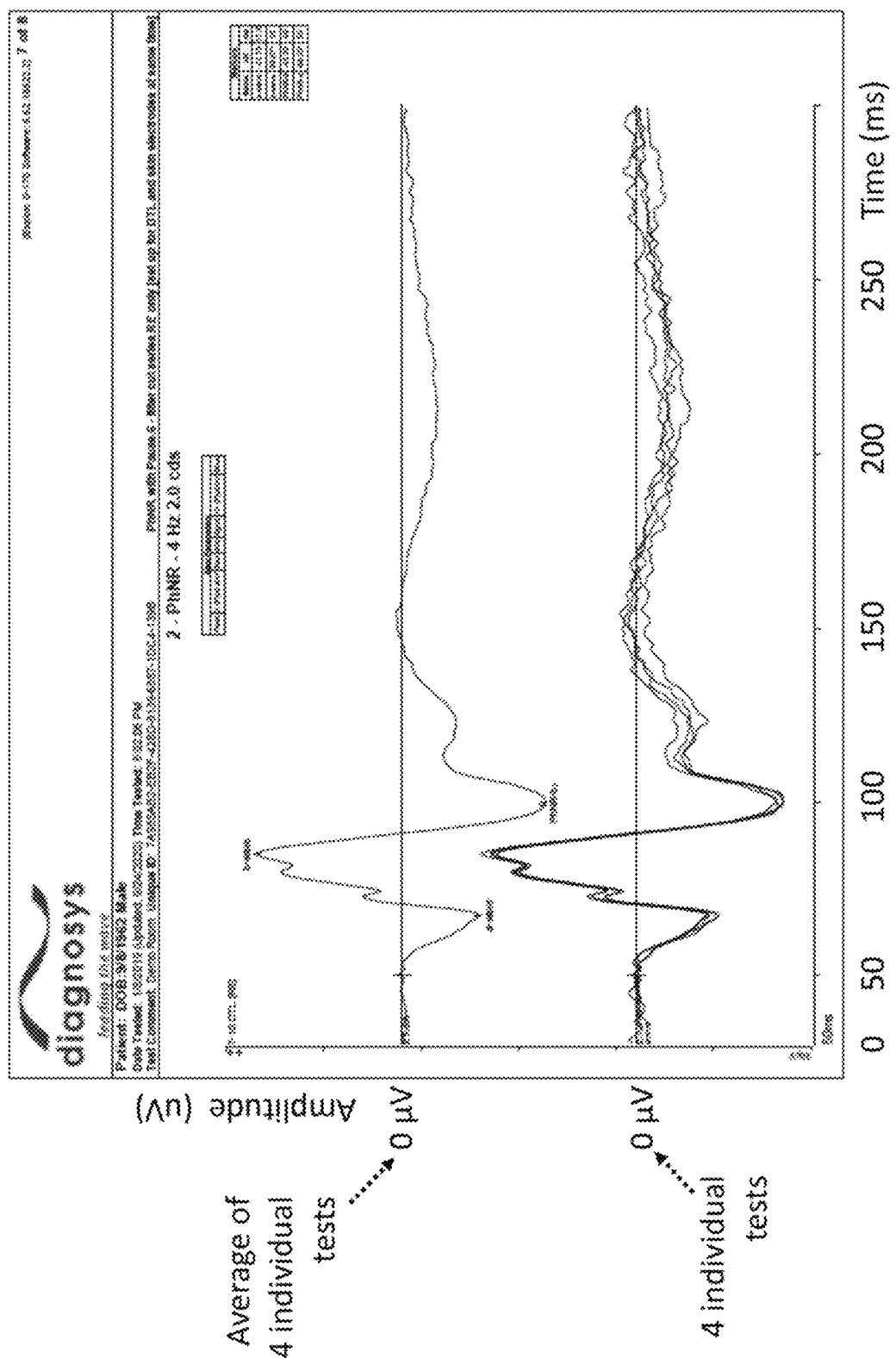
Figure 7H:
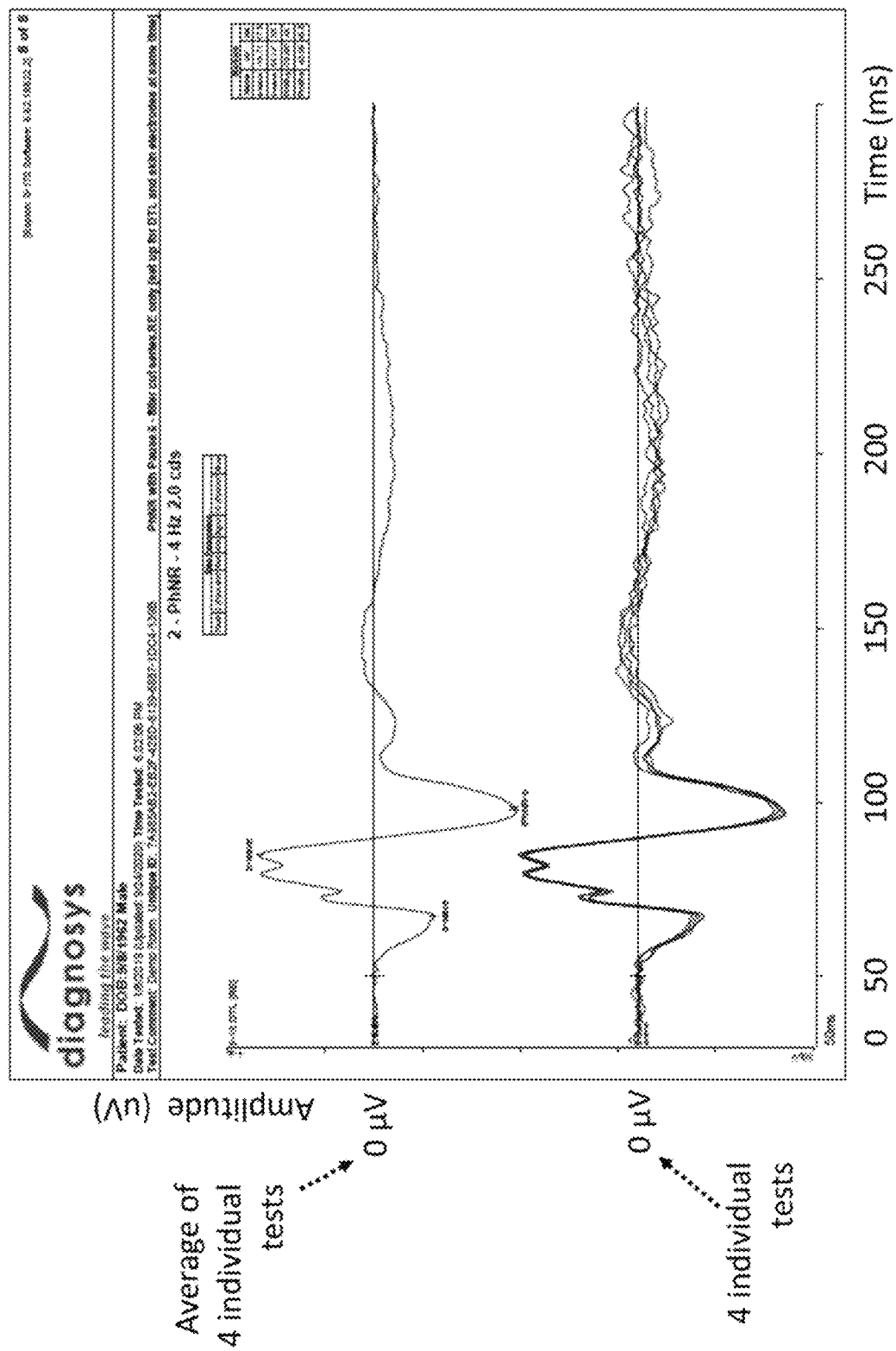

More particularly, and looking now at FIGS. 6a and 7a, in each group of figures, the first panel of each group of figures (i.e., FIGS. 6a and 7a of the first and second groups of figures, respectively) shows the recording filtered using the ISCEV standard 0.3 to 300 hz bandpass filter. The application of such a bandpass filter filtering in accordance with the ISCEV standards acts to remove most of the signal components having frequencies of less than 0.3 hz or more than 300 hz so that the frequencies of more than 0.3 hz and less than 300 hz remain in the recording. Three observations in each case illustrate the effect of eye muscle artifacts on the recording in which a bandpass filter filtering in accordance with the ISCEV standards is used to remove most of the signal components having frequencies of less than 0.3 hz or more than 300 hz.

First, the PhNR peak is very small (i.e., nearly zero). For a healthy test subject's retina that is an incorrect retinal recording (i.e., because the PhNR peak should be significantly more prominent).

Also, in tests that have no eye muscle artifacts, the recorded trace will gradually transition from the PhNR peak (at about 60-80 milliseconds after flash) back up to 0 μV because the retinal response will conclude approximately 100-150 milliseconds after the application of the flash stimulus. However, for both test subjects, with the tests using ISCEV standard 0.3 to 300 hz bandpass filter, the recordings do not transition smoothly back to 0 μV, but instead have large negative or positive amplitudes after the PhNR, which is likely caused by eye muscle artifacts, thus distorting the post-PhNR signal, and likely the PhNR peak itself.

Finally, the 4 individual test recordings using ISCEV standard 0.3 to 300 hz bandpass filter are seen to not be very repeatable. Given that these recordings were each made within 1-2 minutes of one another, and given that the retina did not physically change in that period of time, it is logical to conclude that the lack of repeatability is likely caused by eye muscle artifacts.

Looking now at FIGS. 6b-6h and 7b-7h, as the EHPF of the present invention is applied to greater frequency levels in order to remove frequency values that were previously retained in the recording, each of the aforementioned issues are resolved. More particularly, when frequency values that are greater than 0.3 hz, but less than a selected frequency (e.g., 0.5 hz (FIGS. 6b and 7b), 1 hz (FIGS. 6c and 7c), 2.5 hz (FIGS. 6d and 7d), 5 hz (FIGS. 6e and 7e), 7.5 hz (FIGS. 6f and 7f), 10 hz (FIG. 6g and 7g), or 15 hz (FIGS. 6h and 7h)) are removed from the recording, the PhNR normal negative peak appears, the traces work their way toward 0 μV amplitude not long after the PhNR peak, and the repeatability of the 4 individual traces is greatly improved. EHPF settings passing frequencies above 2.5, 5 or 7.5 hz (i.e., eliminating signal components with frequencies below 2.5, 5 or 7.5 hz, respectively) are thought to be optimal in eliminating most of the eye muscle energy artifact while leaving most of the RGC energy in the recording.

Figure 6E:
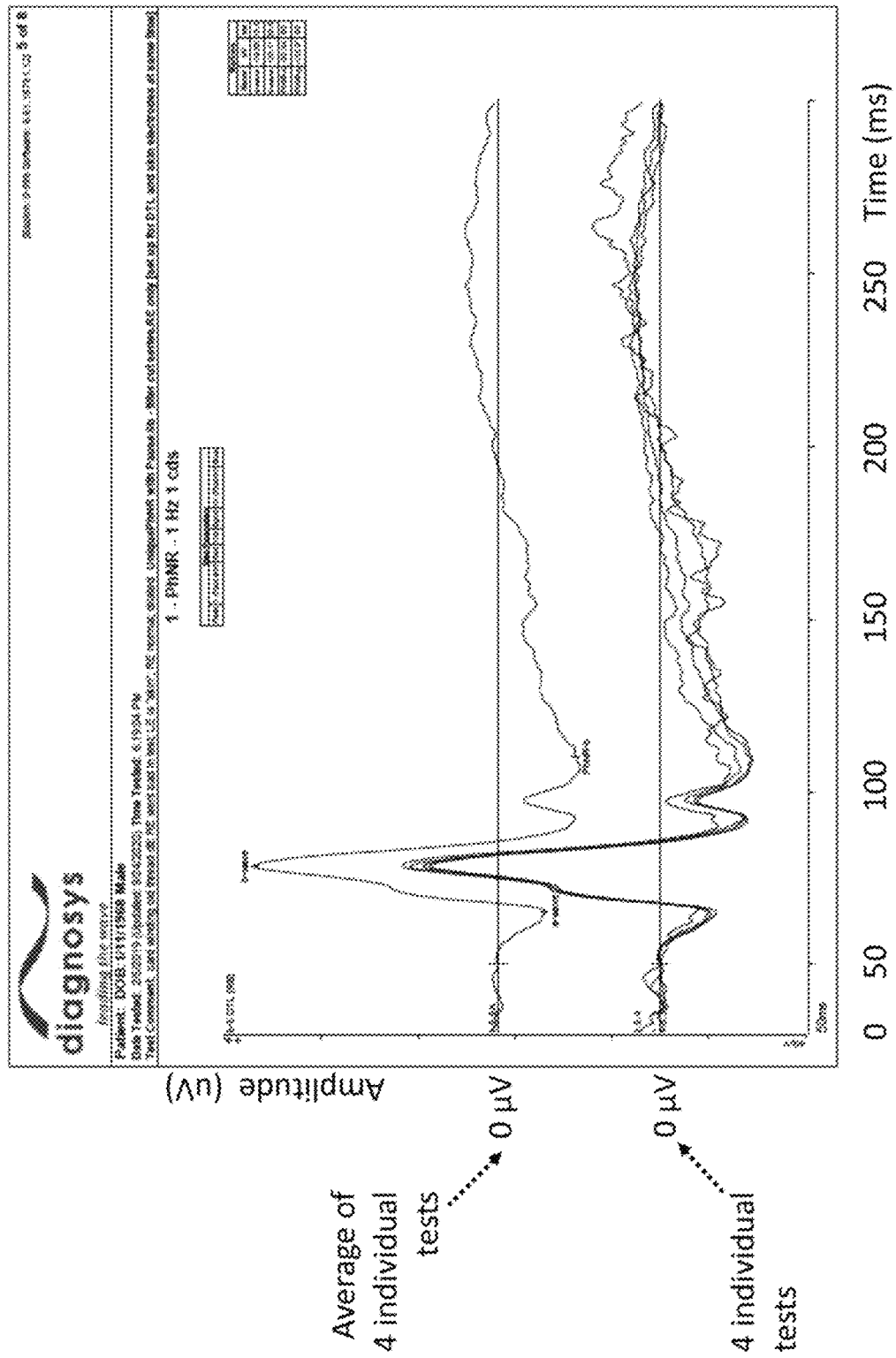
Figure 6F:
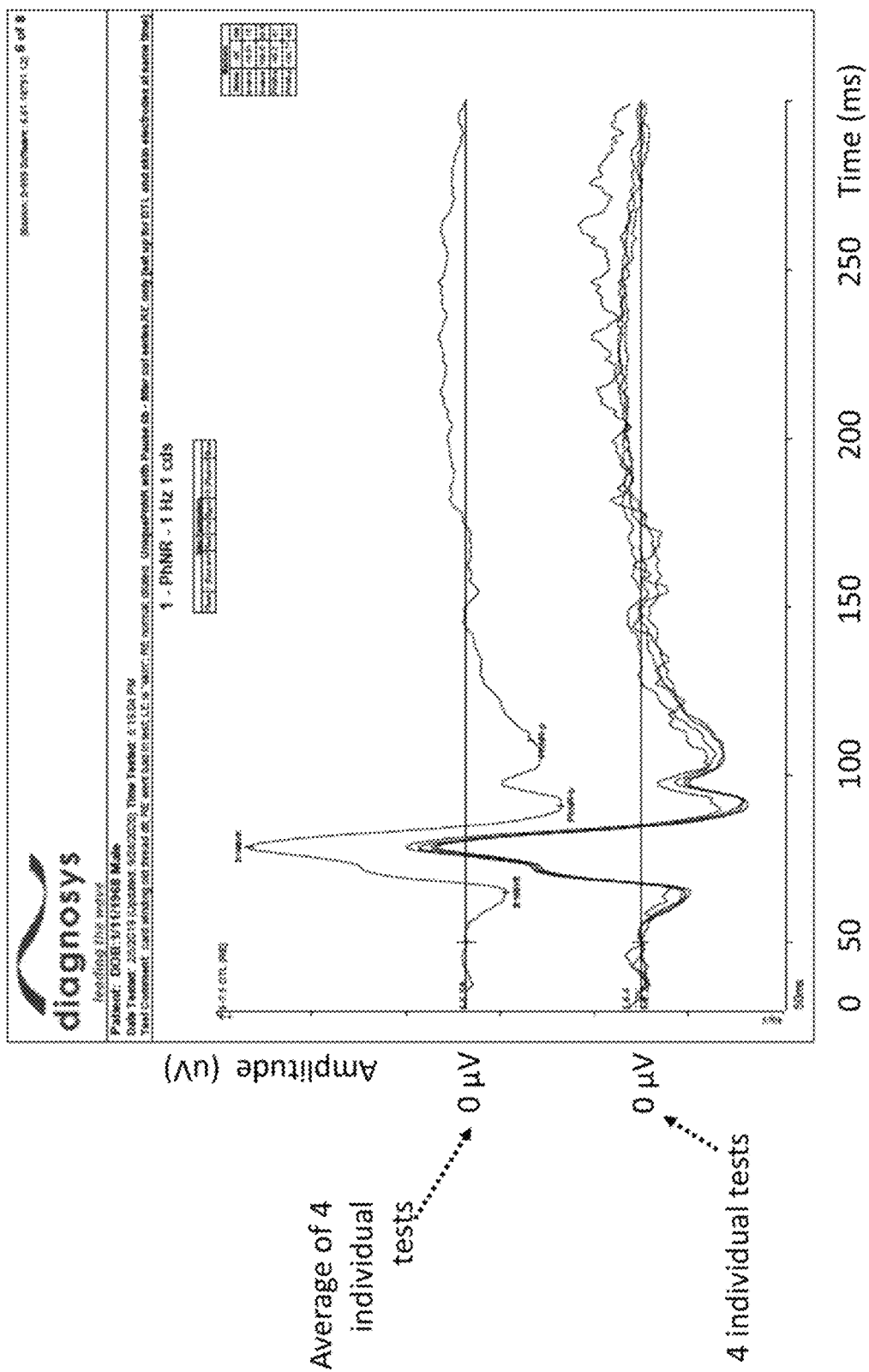
Figure 6G:
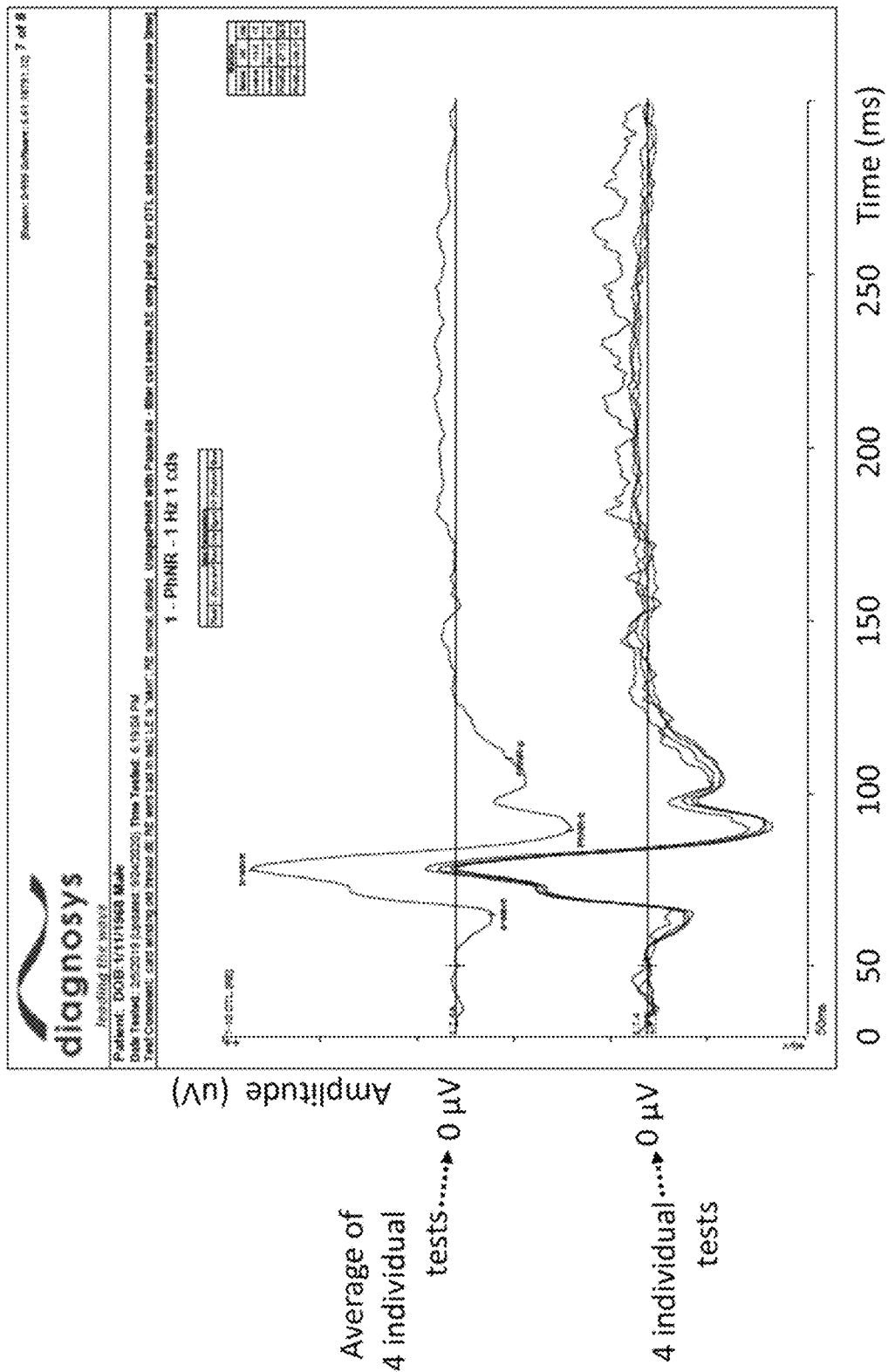
Figure 6H:
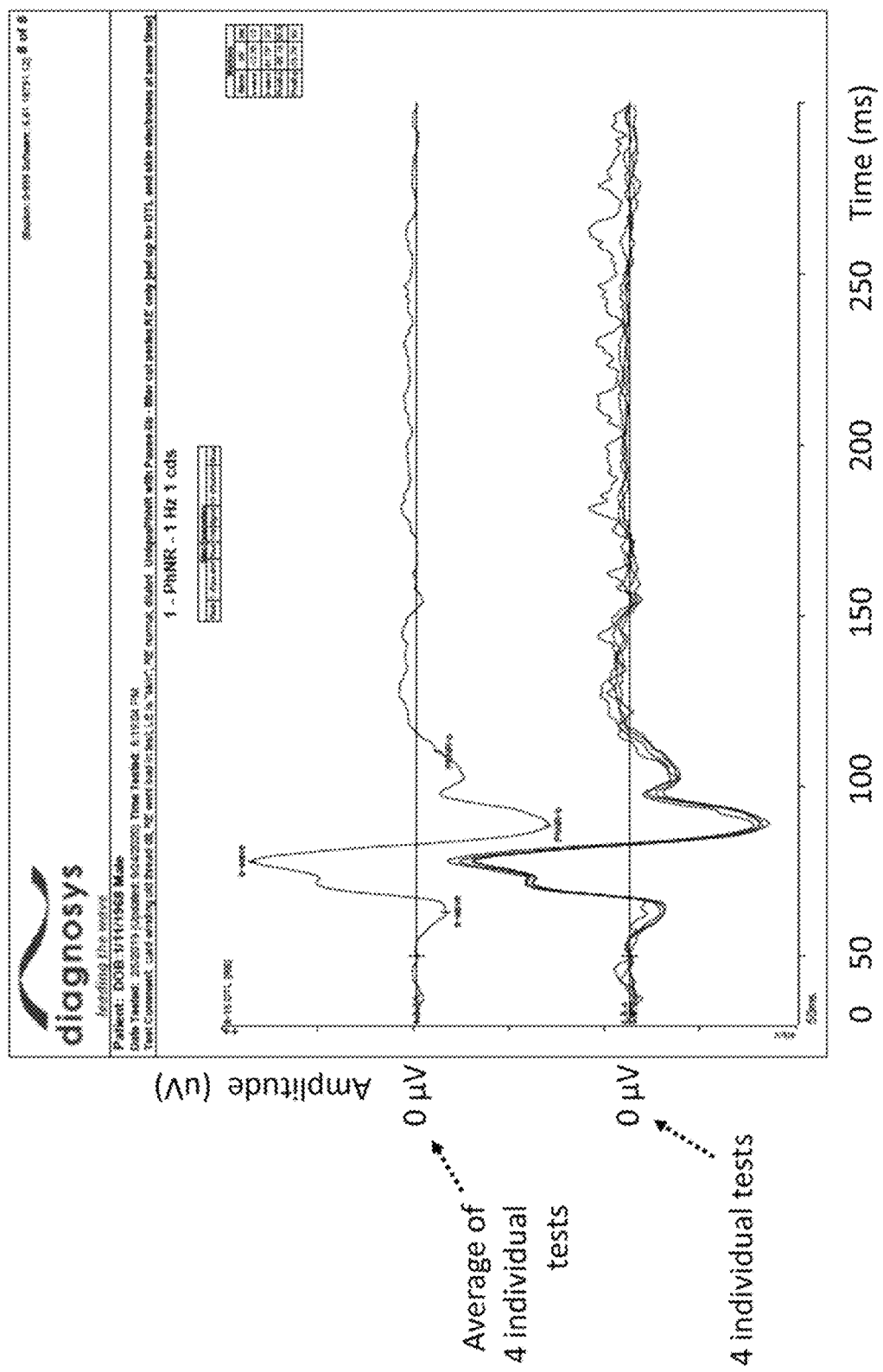

In one preferred form of the present invention, the EHPF comprises a bandpass filter that removes signal components exhibiting a frequency of less than 5 hz (FIG. 6e).

It should also be appreciated that it is common today to use a lower than 300 hz low pass filter (i.e., a filter that removes signal components with frequencies above that of the filter), but which are lower than the ISCEV standard of 300 hz. By way of example but not limitation, use of a lower than 300 hz low pass filter may help to eliminate some of the higher frequency noise that can exist in recorded signals. The EHPF of the present invention also works with a lower than 300 hz low pass filter, including values as low as 45 hz.

Figure 8A:
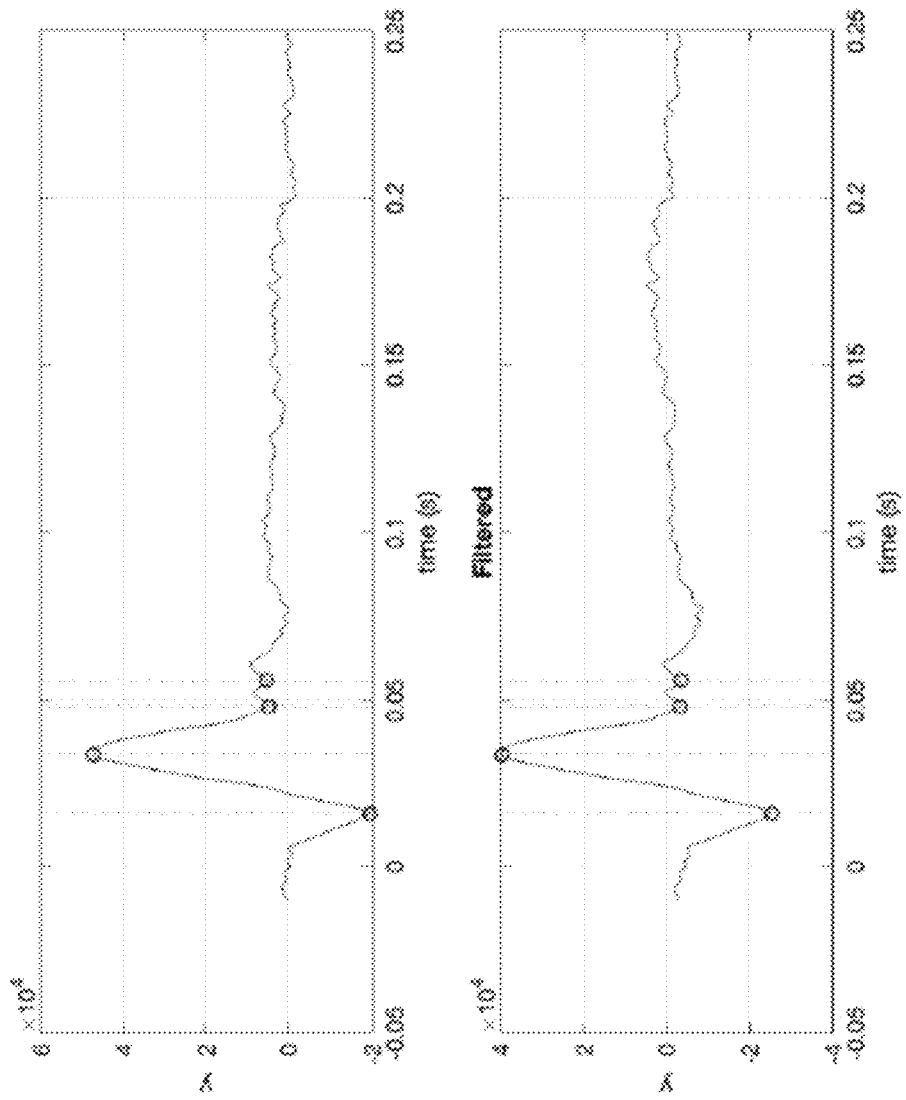
FIGS. 8*a* and 8*b* show recordings resulting from an ERG performed on a glaucoma patient, including the results obtained after an Elevated High Pass Filter (EHPF) formed in accordance with the present invention (in this case a Fourier filter type) have been applied to the respective recordings.
Figure 8B:
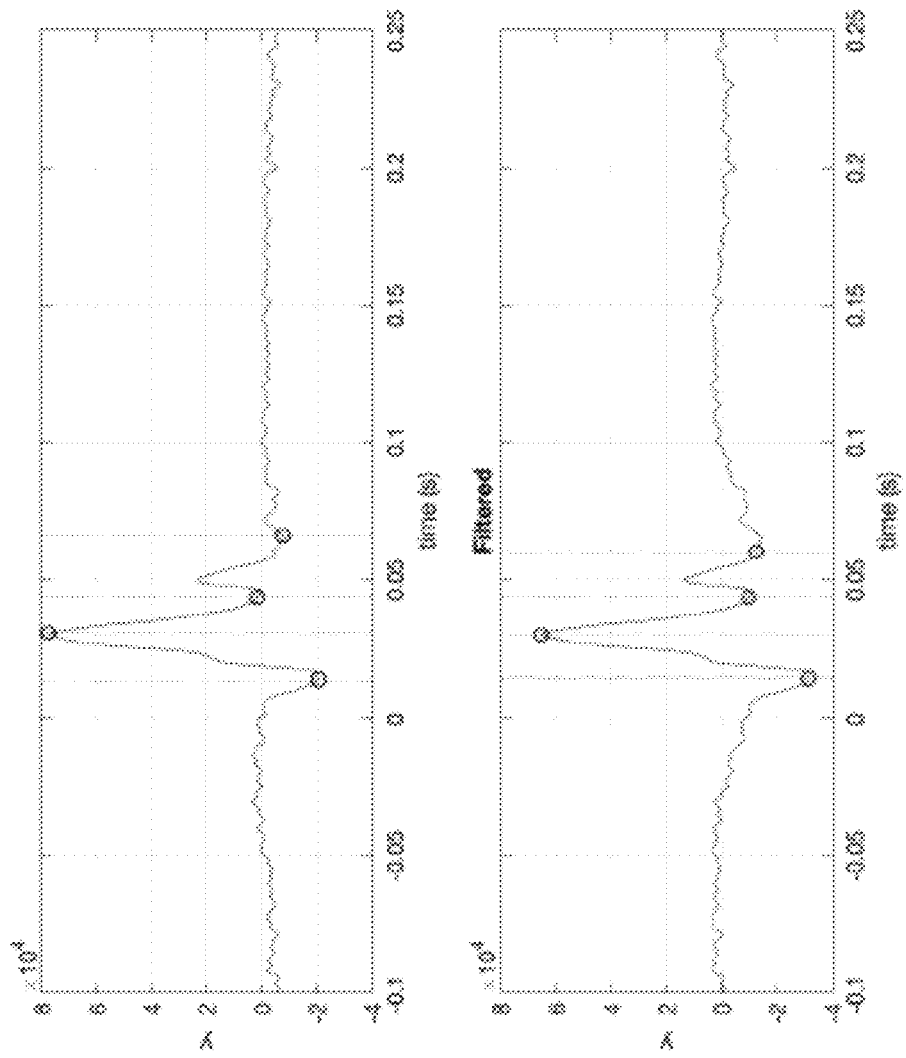

Looking now at FIGS. 8a and 8b, there is shown a recording resulting from an ERG performed on a glaucoma patient, including the results of a PhNR test. In each of FIGS. 8a and 8b, the upper panel shows the recording using standard 0.3 to 300 hz bandpass filtering (i.e., signal components having frequencies of more than 0.3 hz and less than 300 hz remain in the recording). In the lower panel of each of FIGS. 8a and 8b, a 7.5 hz EHPF has been applied (i.e., removing signal components having frequencies less than 7.5 hz), and it is observed that in both cases a low PhNR amplitude is recorded as expected for a glaucoma patient. Furthermore, in each of the recordings shown in FIGS. 8a and 8b, after the PhNR peak response, the recorded signal returns to 0 μV in a direct manner within 100-200 milliseconds after the flash stimulus.

Thus, FIGS. 8a and 8b show the validity of using the EHPF at 7.5 hz to remove signal components exhibiting frequencies less than 7.5 hz, even in a case with lower eye muscle artifacts and glaucoma. Both the low PhNR amplitude and the fact that the recorded signal returns to 0 μV within 100-200 milliseconds after the flash stimulus are important considerations in using a filter such as the EHPF of the present invention because, prior to the test, it generally is not known if the patient is normal or affected by glaucoma, and it is generally not known whether or not there will be significant eye muscle artifacts during the test.

Preferred Sweep Filter (PSF)

The Preferred Sweep Filter (PSF) of the present invention is configured to evaluate and improve the signal recorded during an ERG/PhNR test in time space. The PSF selects, based on the characteristics of each recorded signal, which sweeps of the recorded test should be eliminated (i.e., because those sweeps likely represent too much muscle artifact energy) from those sweeps which should be retained (i.e., because those sweeps represent proper measurements of retinal electrical activity).

Figure 9A:
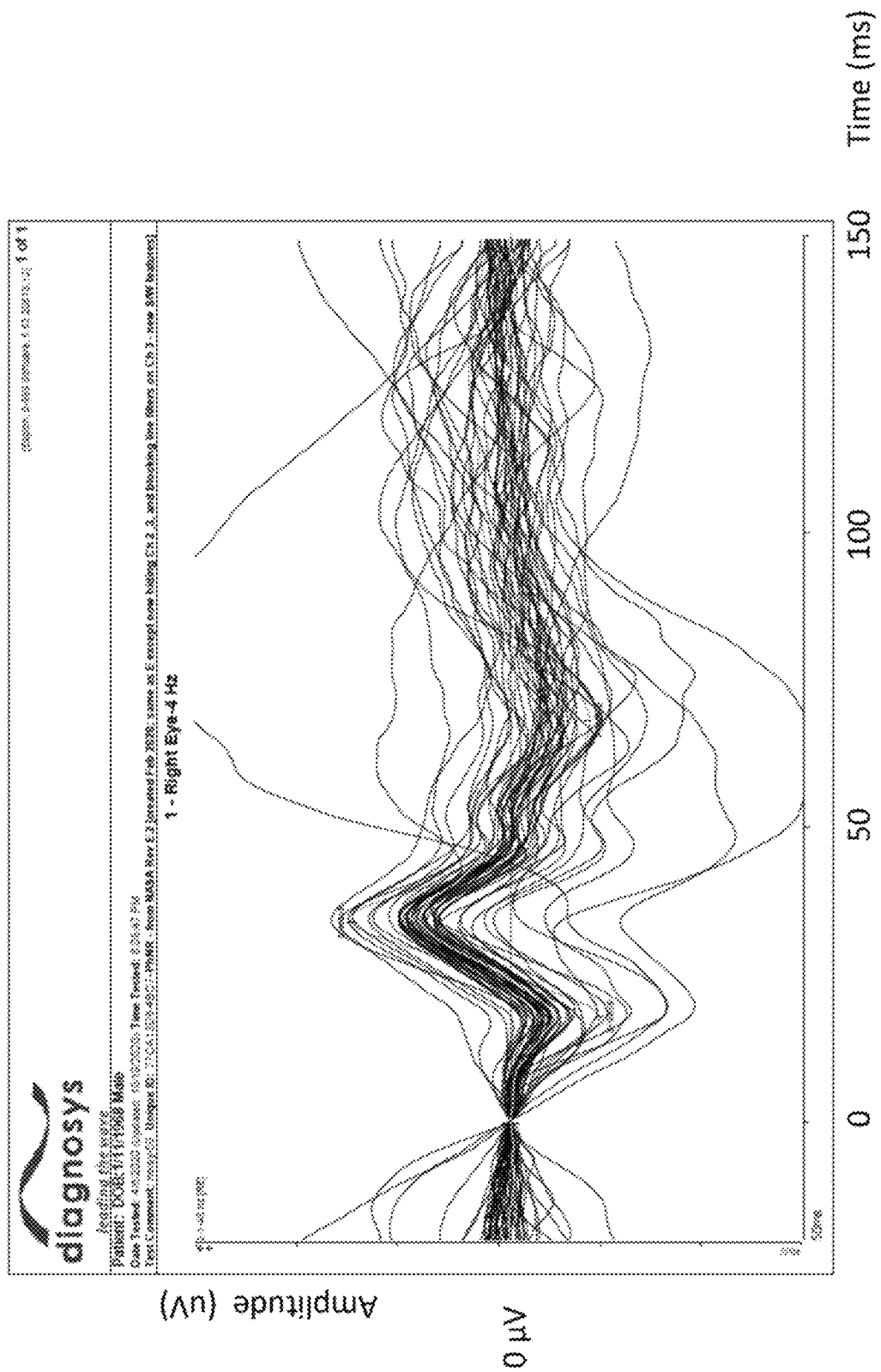
FIG. 9*a* shows an exemplary recording obtained by performing an ERG test comprising 50 sweeps.

FIG. 9a shows a typical recording obtained by performing an ERG test (in this case a PhNR ERG test) comprising 50 sweeps of the test, with each sweep being accorded a line on the resulting recording (in this case, each individual sweep is based on one recording for 150 milliseconds, each after a brief, e.g., 4 millisecond, flash of light that is presented to the subject's eye). Conventional methods typically call for averaging all 50 sweeps, and consider the final average of the 50 sweeps to be a single test result.

As discussed above, the goal of an ERG test is to record electrical energy from the retina, however, the problem is that muscle energy is also often recorded. The goal of the PSF is to eliminate as much of the recorded muscle energy as possible, while leaving as much of the recorded retinal energy as possible. As also discussed above, based on empirically-derived non-human primate and human PhNR recordings, it is known how a test result devoid of muscle artifact energy should appear in the resulting electroretinogram.

Figure 9B:
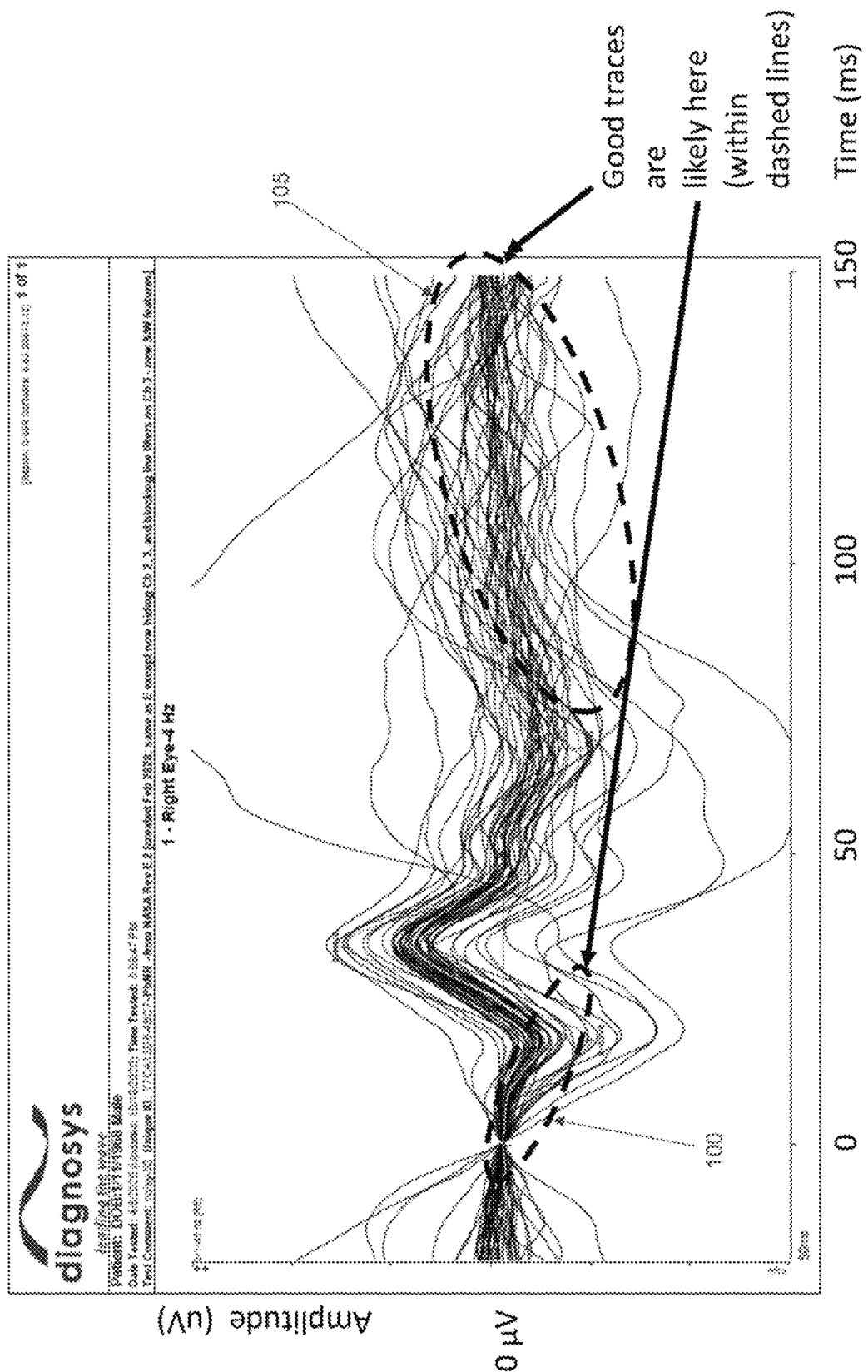
FIG. 9*b* shows further aspects of the exemplary recording of FIG. 9*a*, in which the sweeps which exhibit the lowest level of muscle artifacts have been identified.

Looking now at FIG. 9b, there are shown two dashed line ovals 100, 105. The portions of the sweeps contained within dashed line ovals 100, 105 represent the sweeps which exhibit the lowest levels of muscle artifacts (which can affect the end of a sweep and into the beginning of the next sweep), and hence, those are the sweeps the PSF is configured to select, while eliminating the other sweeps.

Finally, after selecting the desired sweeps using a PSF, the selected sweeps are averaged to calculate the single test result, with the single test result being much more representative of retinal electrical response and with significantly less muscle energy artifacts.

Figure 9C:
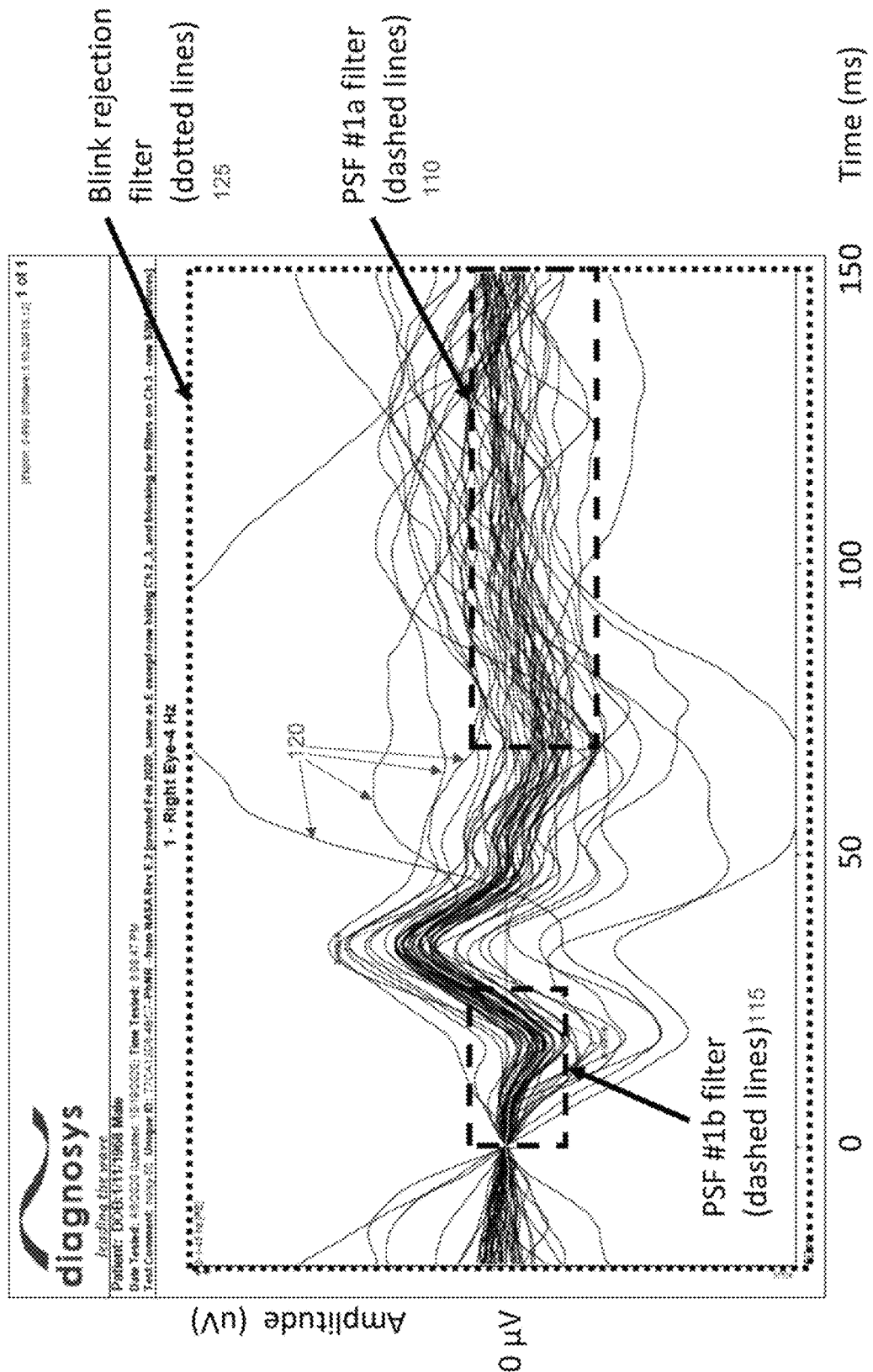
FIG. 9*c* shows two novel Preferred Sweep Filters (PSF) formed in accordance with the preset invention being applied to the recording of FIG. 9*a*.

Looking now at FIG. 9c, there is shown one preferred implementation of a PSF according to the present invention. More particularly, FIG. 9c shows a first PSF 110 (i.e., "PSF #1a filter") and a second PSF 115 (i.e., "PSF #1b filter") being applied to a recording comprising a plurality of sweeps 120. PSF 110 can be used alone, or PSF 115 can be used alone, or both PSF 110 and PSF 115 can be used in combination with one another. Still looking at FIG. 9c, there is also shown a typical blink artifact rejection filter 125 that is commonly used in ERG recordings today. A typical implementation of blink artifact rejection filter 125 is to reject any sweep that has an amplitude larger than +250 µV, or smaller than −250 µV, appearing at any point in the sweep recording. Other typical levels used are +/−500 µV, +/−1,000 µV, etc. When using a blink artifact rejection filter 125, the artifact rejection levels need to be larger than the largest typical ERG response that emanates from the retina. In the PhNR test, the b-wave (which comes primarily from bipolar cells in the retina) appearing in the recording is often as large as 200 µV, typically peaking at 30-40 ms after the flash. Blink rejection filters (e.g., blink artifact rejection filter 125) need to be larger than the b-wave, or they would eliminate "good" (i.e., useful) sweeps based on the b-wave response triggering the blink rejection filter and rejecting those "good" sweeps.

In the recording shown in FIG. 9c, PSF 110 and PSF 115 (represented in FIG. 9c by dashed line boxes) represent the concept of one implementation of the PSF. The areas where either (or both) of PSF 110 and PSF 115 are to be applied to the electroretinogram (or underlying data set) are areas known empirically to potentially contain undesirable artifacts. In this case all sweeps are analyzed during the time period between the two vertical lines of the dashed line box, for example between 70 and 150 ms when PSF 110 is applied (i.e., 150 ms is the end of the recording in this case). Any sweep that has an amplitude above or below the horizontal lines of PSF 110 between 70 and 150 ms is eliminated by PSF 110, and similarly for PSF 115 between 0 and 20 ms. Thus, it will be appreciated that PSF 110 shown in FIG. 9c eliminates sweeps that go above +10 µV or below −50 µV, between 70 and 150 ms after the flash stimuli. PSF 115 shown in FIG. 9c eliminates sweeps that go above +10 µV or below −30 µV, between 0 and 20 ms after the flash stimuli.

Figure 9D:
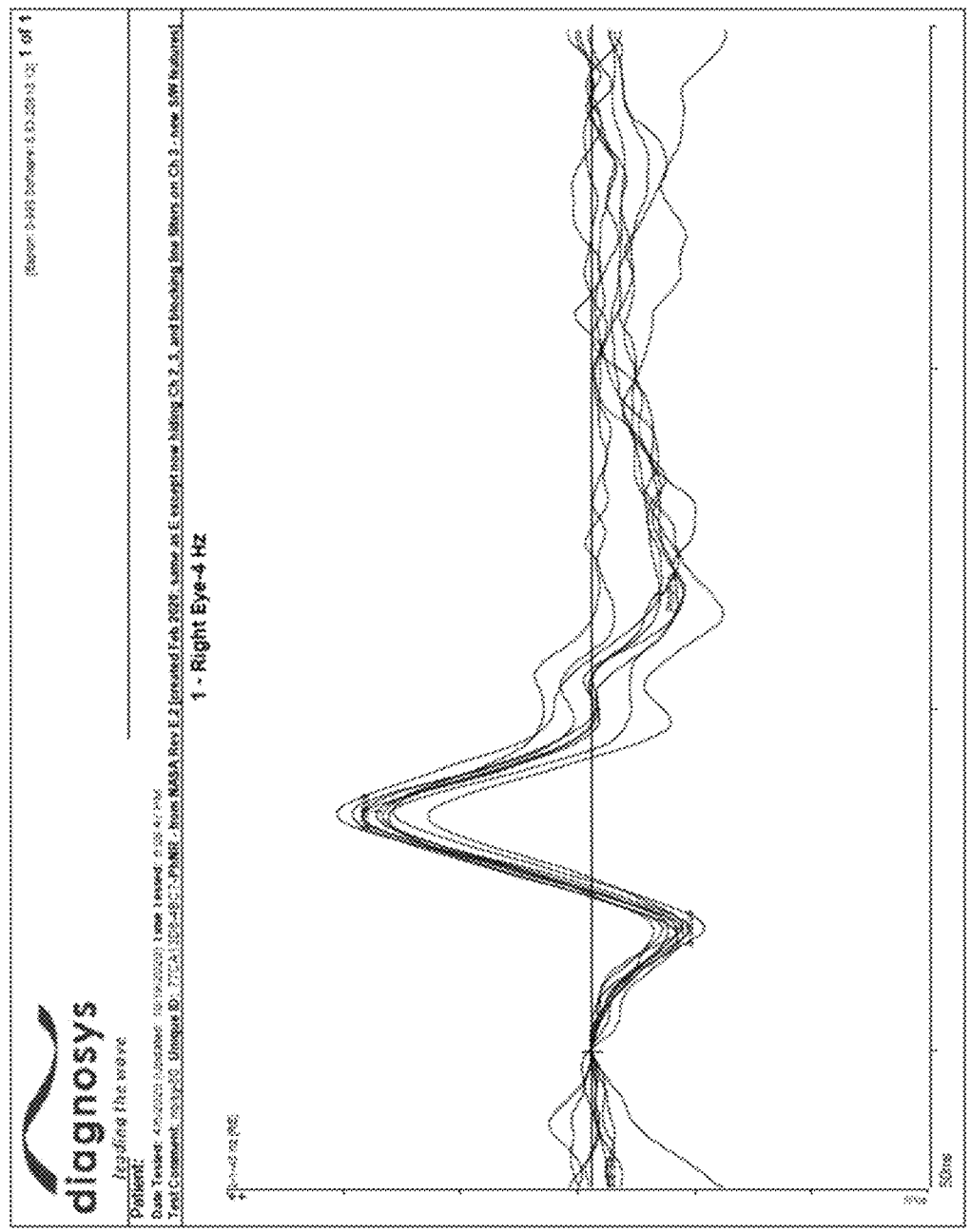
FIG. 9*d* shows the recording of FIG. 9*a* after application of one of the Preferred Sweep Filters (PSF) of FIG. 9*c* to the recording of FIG. 9*a*.

FIG. 9d shows the remaining sweeps after the PSF (i.e., PSF 110 and PSF 115) has been applied to all 50 sweeps in the recording. It will be appreciated that, after applying the PSF, the remaining sweeps primarily reflect only the retinal response characteristics. Specifically, reading the graph of FIG. 9d from left to right, there is shown:
1) a negative going a-wave emanating primarily from the retinal photoreceptors;
2) a positive going b-wave emanating primarily from the retinal bipolar cells; and
3) a negative going PhNR response which emanates primarily from the RGCs.

Thus it will be seen that the PSF of the present invention (e.g., PSF 110 and/or PSF 115) has eliminated sweeps having significant energy resulting from small eye and eyelid movements and twitches, both of which generate electrical signals of similar amplitude to the retinal signals and are much smaller than amplitudes generated by eye blinks.

Figure 10A:
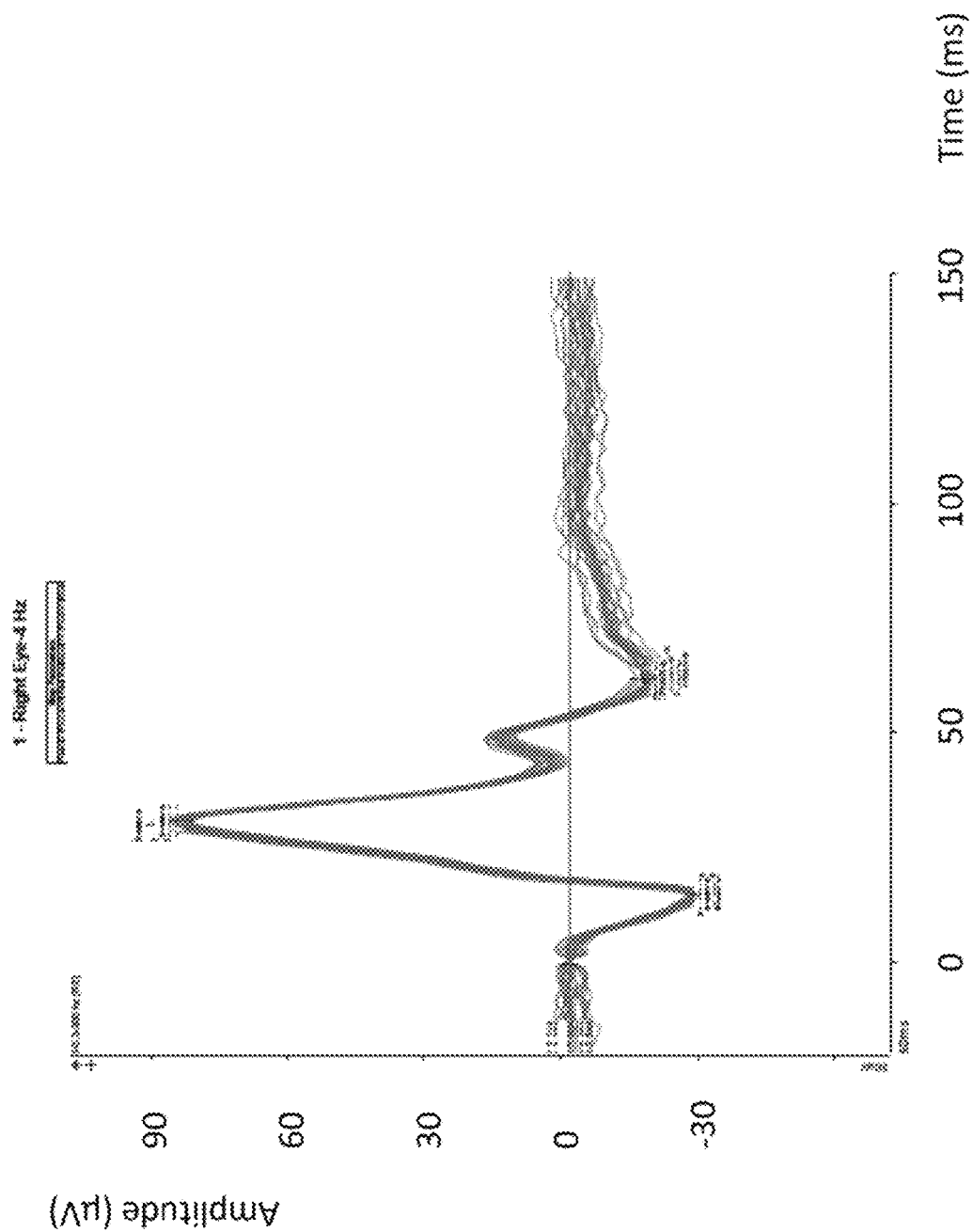
FIG. 10*a* shows a set of 15 tests, wherein each test comprises 50 sweeps, recorded during a test performed on a human test subject, wherein the test subject had almost no eye twitches or eye movements during the tests.

Functional retina performance is believed to not change in a measurable way over a period of a few hours. Therefore, a test of retinal function such as the PhNR ERG test should record similar results when repeated on one human subject within 1-2 hours if the tests are recording primarily retinal electrical response energy. FIG. 10a shows a set of 15 tests (each test comprising 50 sweeps) recorded during a test performed on a human subject. In the case of the recording shown in FIG. 10a, the human test subject is a well-trained test taker who was able to take each of the tests with almost no eye twitches or eye movements during the recordings. In comparing all 15 tests, it can be seen that very high repeatability of all 4 major characteristics of a successful PhNR test was achieved:
1) a-wave;
2) b-wave;
3) PhNR peak response; and
4) the recording returns to 0 µV in a gradual manner within 50-100 ms after the PhNR response (without large positive or negative deviations after the PhNR peak).

Figure 10B:
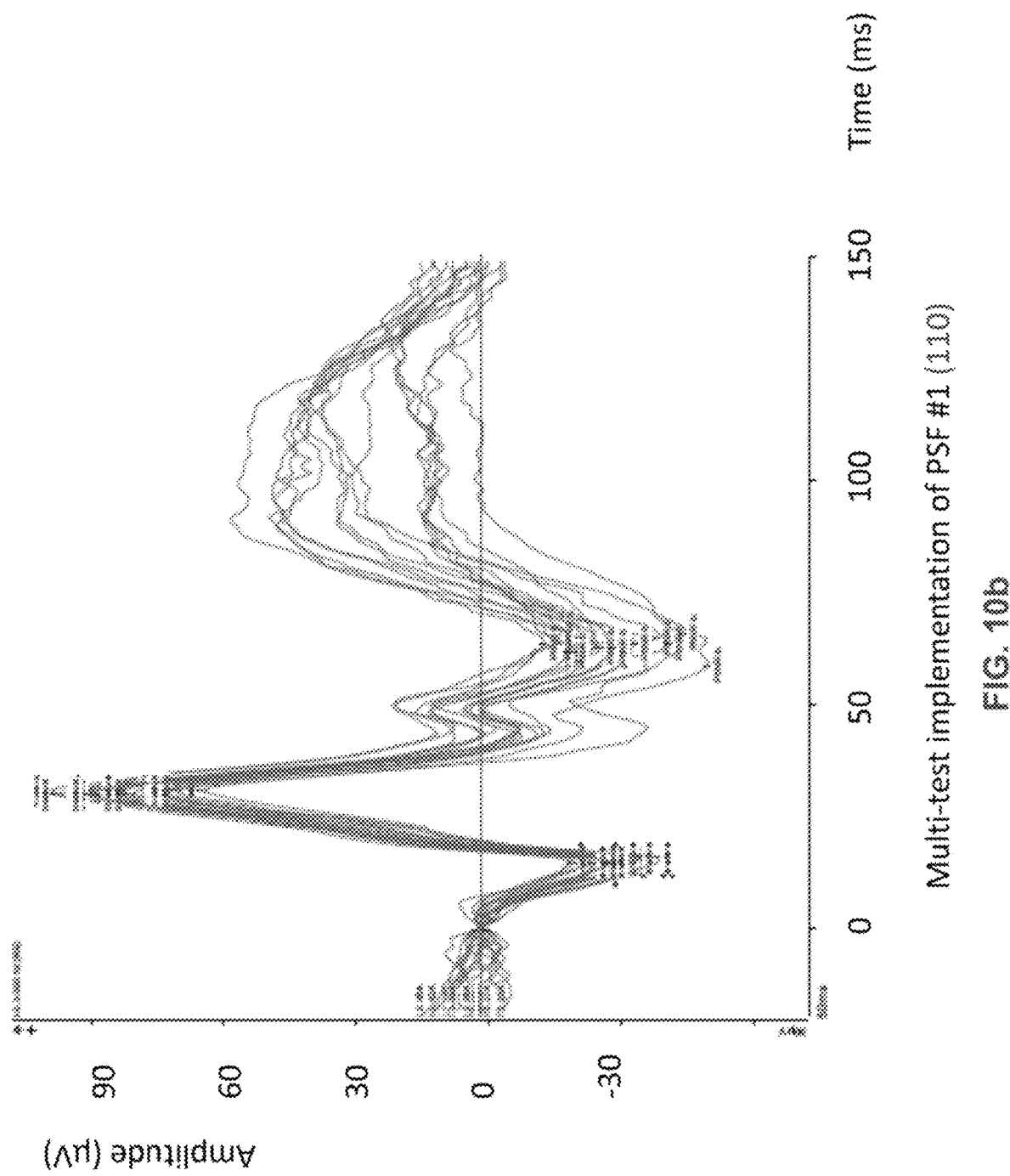
FIG. 10*b* shows a set of 15 tests recorded during a test performed on a human test subject, wherein the test subject intentionally engaged in eye twitches and eye movements during the tests.

FIG. 10b shows a set of 15 tests recorded during a test performed on the same subject (on the same day), wherein the subject intentionally created representative artifacts by engaging in movement such as small eye twitches and eye movements during the test. The 15 tests show typical characteristics of a PhNR test that is affected by these artifacts such as a poor repeatability of the a-wave, b-wave and PhNR peak response, as well as a large deviation (from a curve that should be gradually going back to 0 µV after the PhNR peak response) at about 100 ms.

Figure 10C:
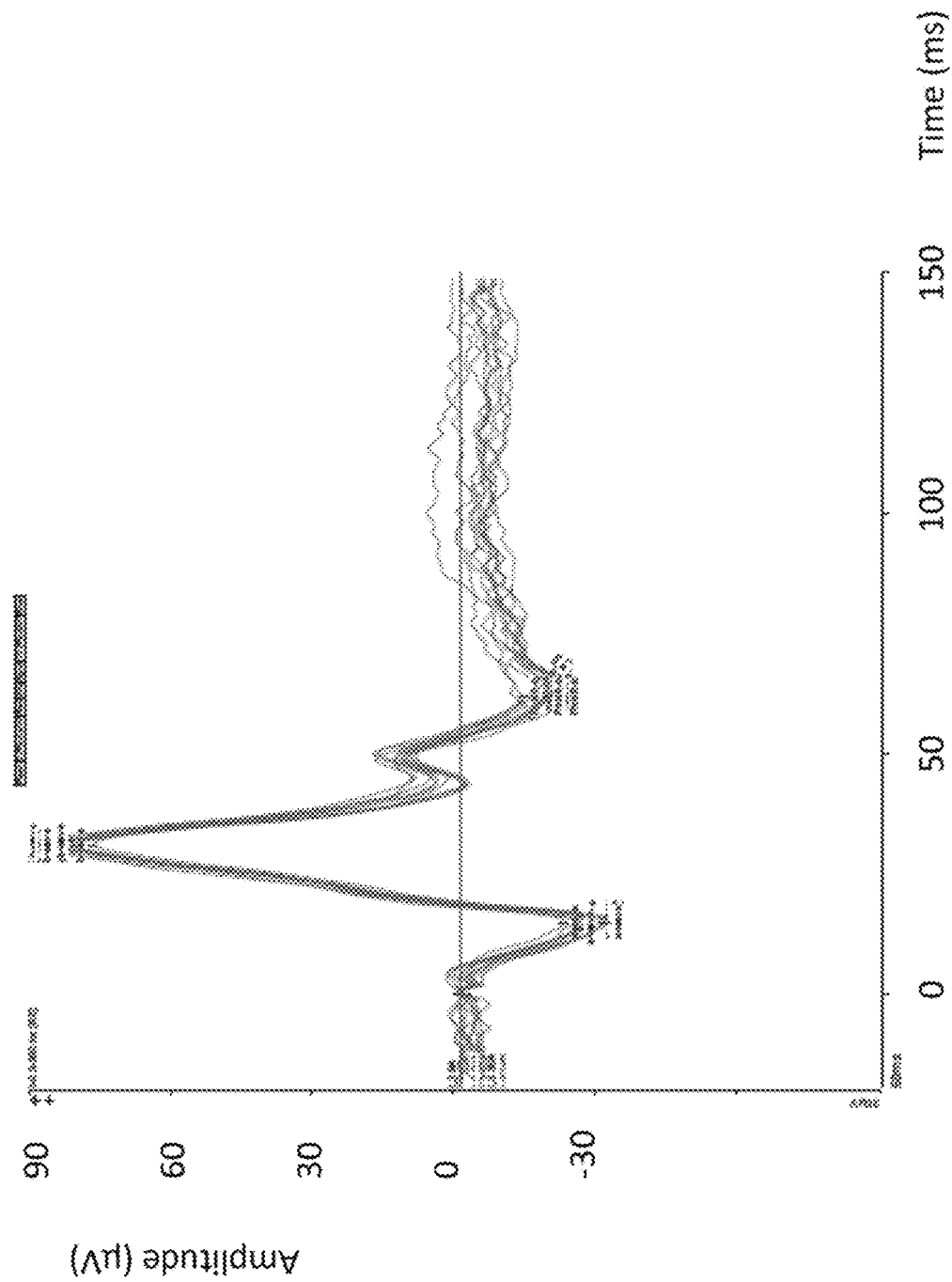
FIG. 10*c* shows the set of tests of FIG. 10*b* after a novel Preferred Sweep Filter (PSF) formed in accordance with the present invention has been applied to the recording of FIG. 10*b*.

FIG. 10c depicts the same set of tests as shown in FIG. 10b, but after PSF 110 has been applied individually to each of the 15 tests. It will be appreciated that the 15 tests, which sweeps reflect significant eye artifact energy, are now much more repeated for the three waves (a, b, PhNR) when applying the PSF 110.

Importantly, the recordings depicted in FIG. 10c (after application of PSF 110) generally return to 0 µV in a gradual manner within 50-100 ms after the PhNR peak response, indicating that most of the eye artifact energy has been eliminated while still preserving the retinal response.

Other implementations of the PSF of the present invention will be apparent to those skilled in the art in view of the present disclosure. By way of example but not limitation, PSF 110, as described above, is characterized by rejection criteria of +10 µV and −50 µV within the time window of 70 to 150 ms (i.e., resulting in a rectangular shaped PSF). Other implementations of PSF 110 may be used, including those with tighter amplitude restrictions (e.g., +5 µV and −30 µV) and over other time windows (e.g., starting at 50 or 60 ms, and ending at much later times such as 250 ms, 1,000 ms or at the end of the recording of a sweep whenever that might occur).

Figure 11A:
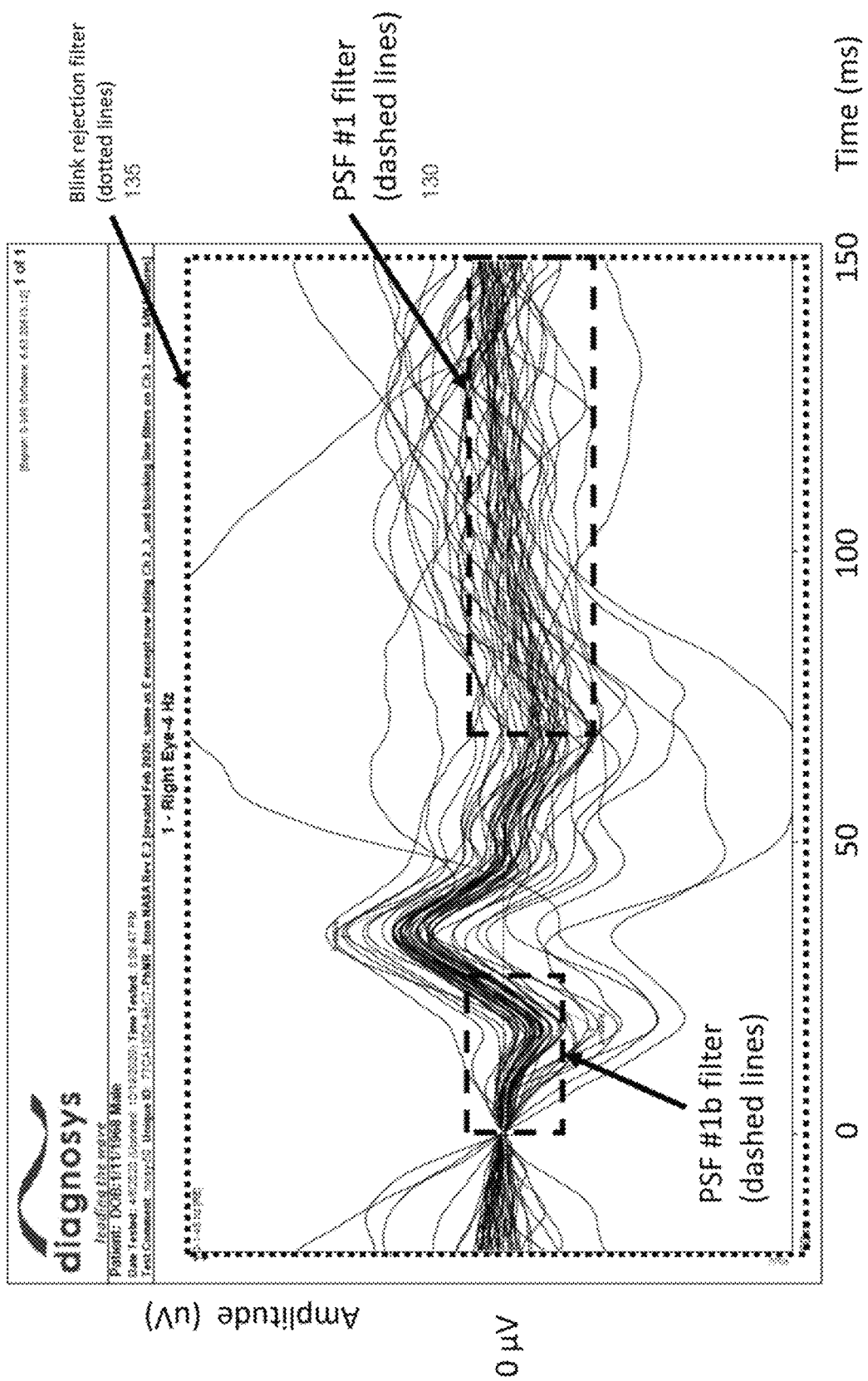
FIGS. 11*a* and 11*b* show other Preferred Sweep Filters (PSF) formed in accordance with the present invention.
Figure 11B:
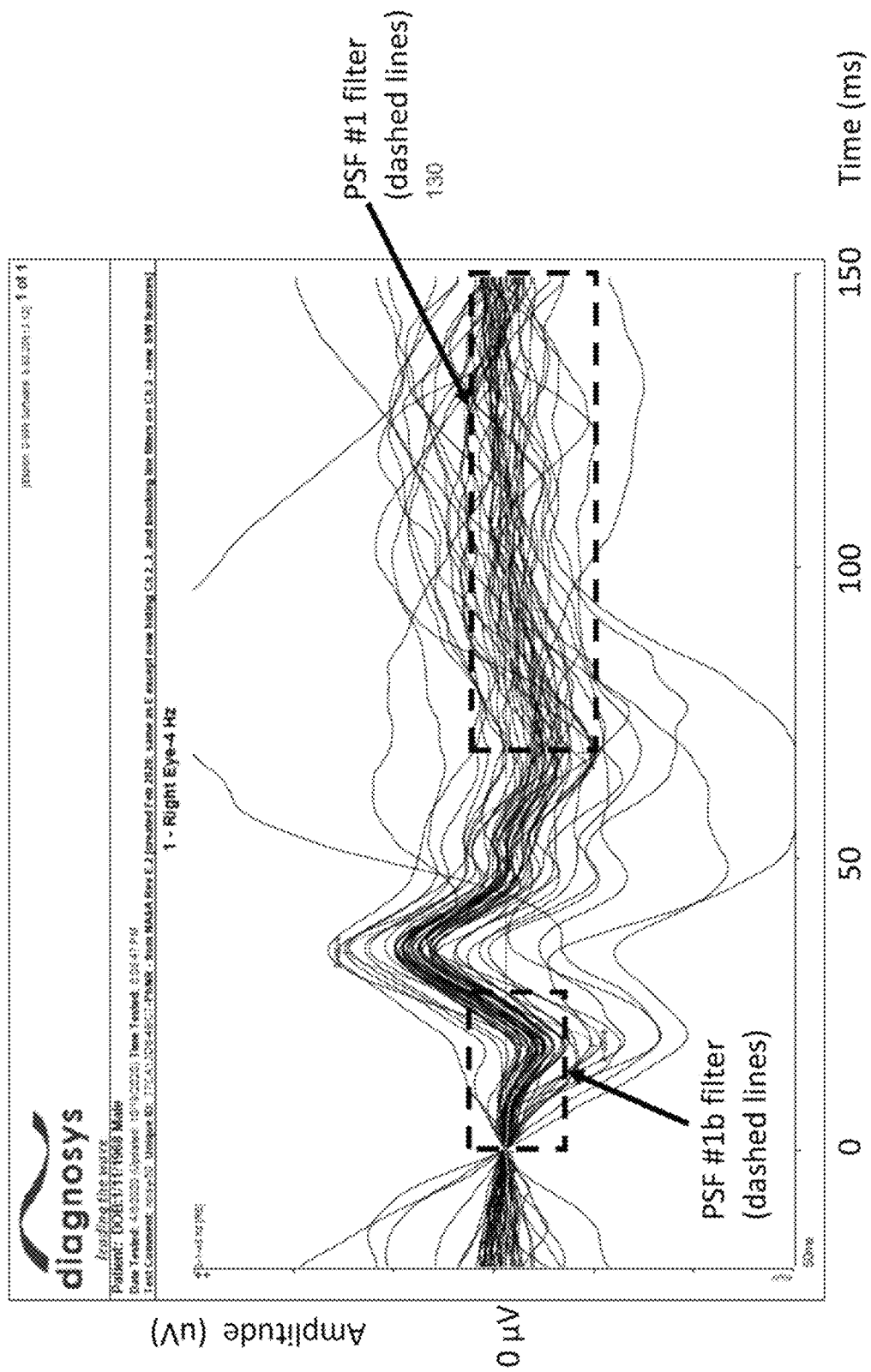

By way of further example but not limitation, and looking now at FIGS. 11a and 11b, there is shown a PSF 130 (dashed line box), which may be used in conjunction with a standard blink artifact rejection filter 135 (dotted line box), as shown in FIG. 11a, or without a standard blink artifact rejection filter, as shown in FIG. 11b.

Figure 12A:
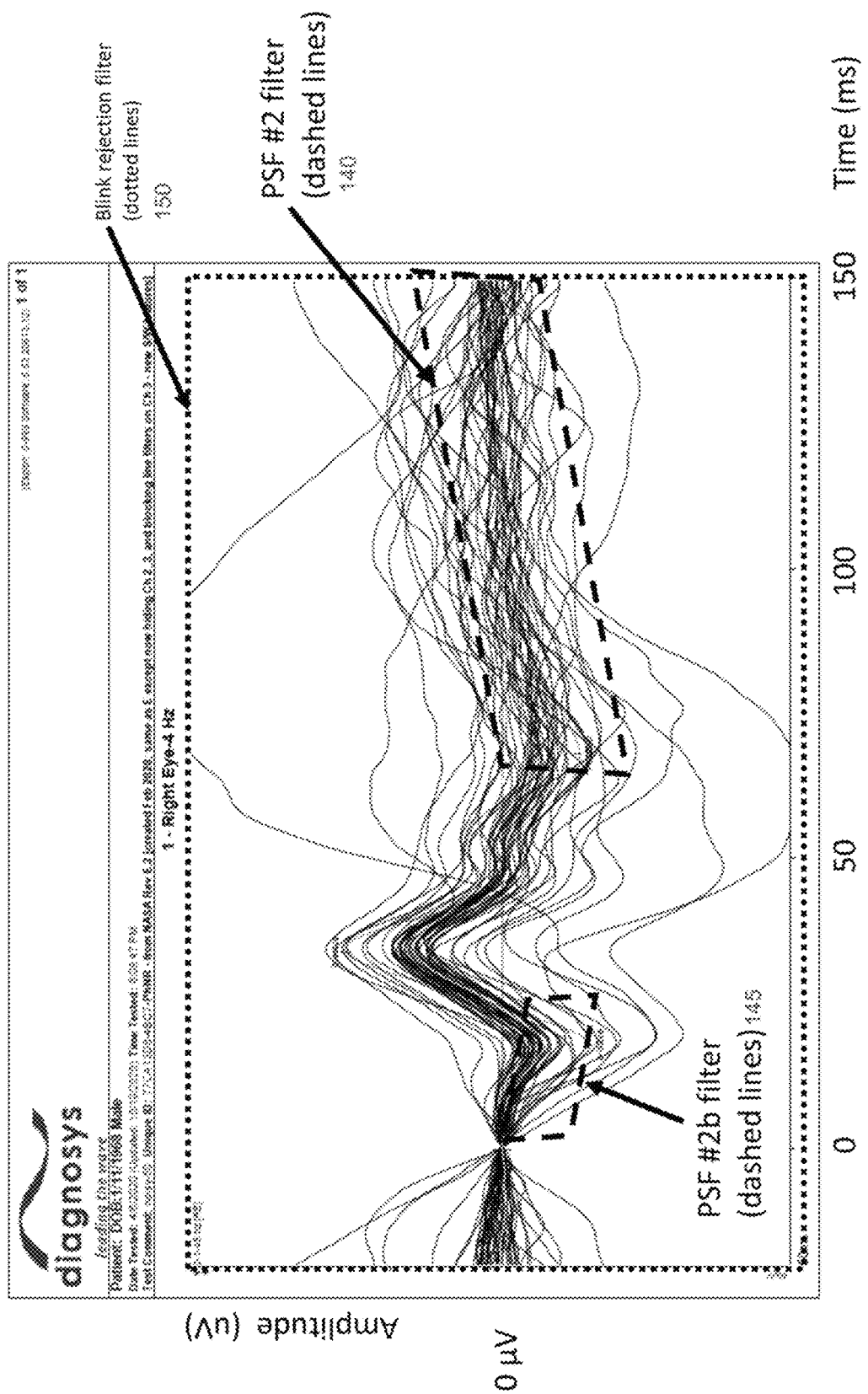
FIGS. 12*a* and 12*b* show still other Preferred Sweep Filters (PSF) formed in accordance with the present invention.
Figure 12B:
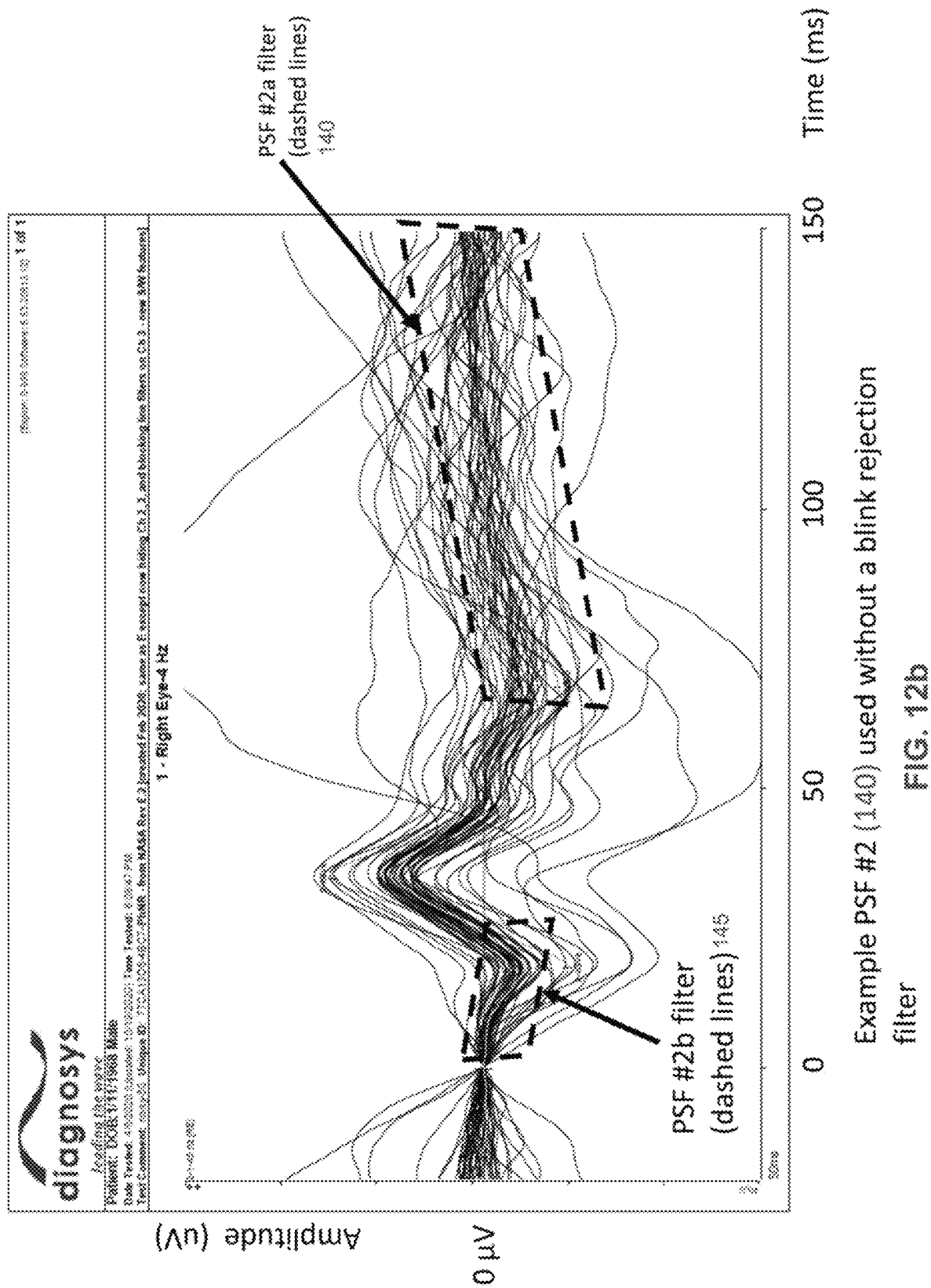

It will also be appreciated that other shapes of PSF are possible and may be effective in eliminating eye artifacts. By way of example but not limitation, FIGS. 12a and 12b show another novel PSF 140 and a novel PSF 145, with both PSF 140 and PSF 145 being generally in the shape of a parallelogram. As with the rectangularly-shaped PSFs 110, 115 discussed above (FIG. 9*c*), PSF 140 and/or PSF 145 may be used alone or in combination with one another. The primary difference between PSF 140 compared to PSF 110 is that the reject bars' amplitude levels of PSF 140 vary linearly across the time that is being evaluated by the filter, as shown in FIGS. 12*a* and 12*b*.

PSF 140 can also be used with a standard blink artifact rejection filter 150 (the dotted line box), as shown in FIG. 12*a*, or without standard blink artifact rejection filter 150, as shown in FIG. 12*b*.

Figure 13A:
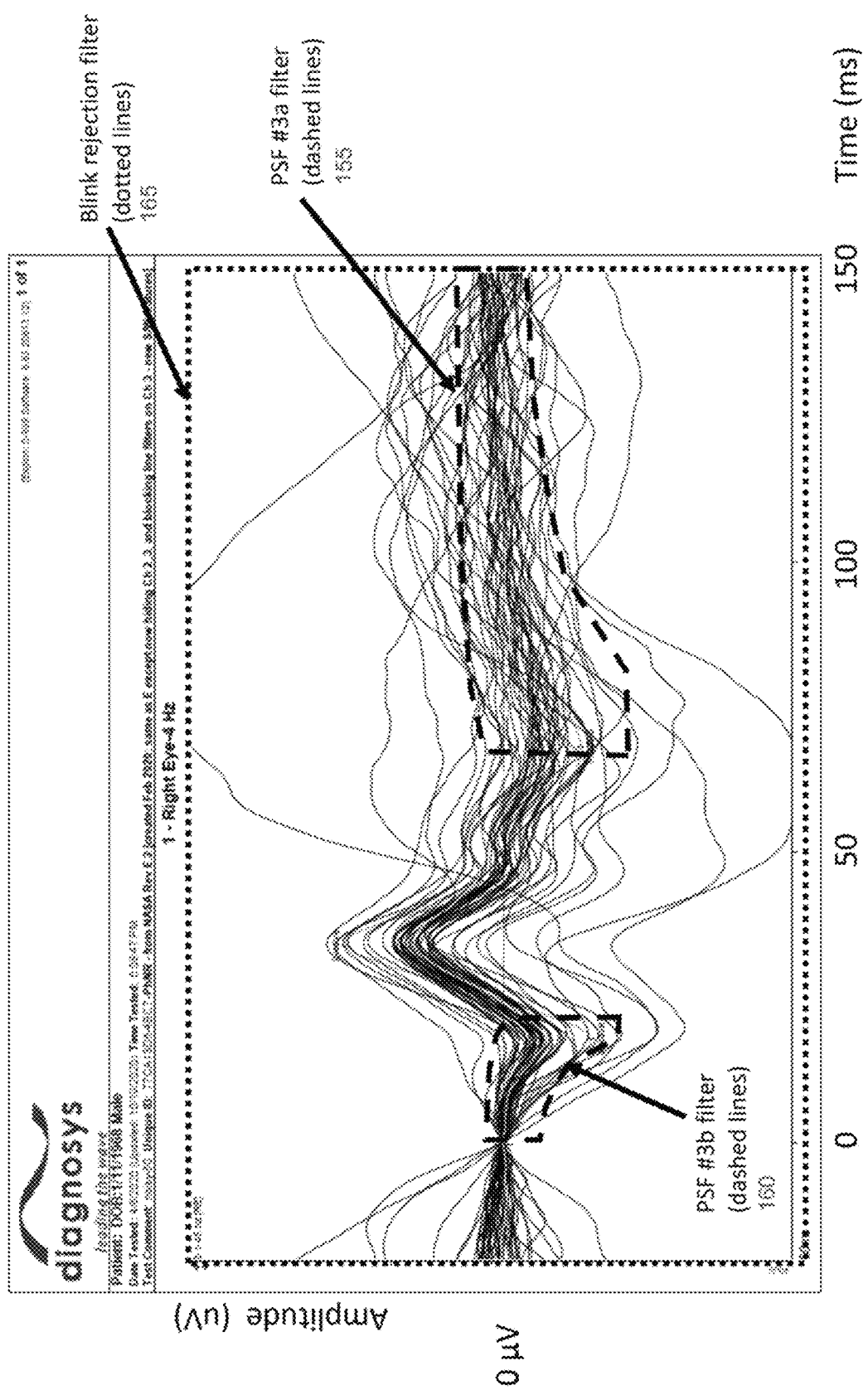
FIGS. 13*a* and 13*b* show yet other Preferred Sweep Filters (PSF) formed in accordance with the present invention.
Figure 13B:
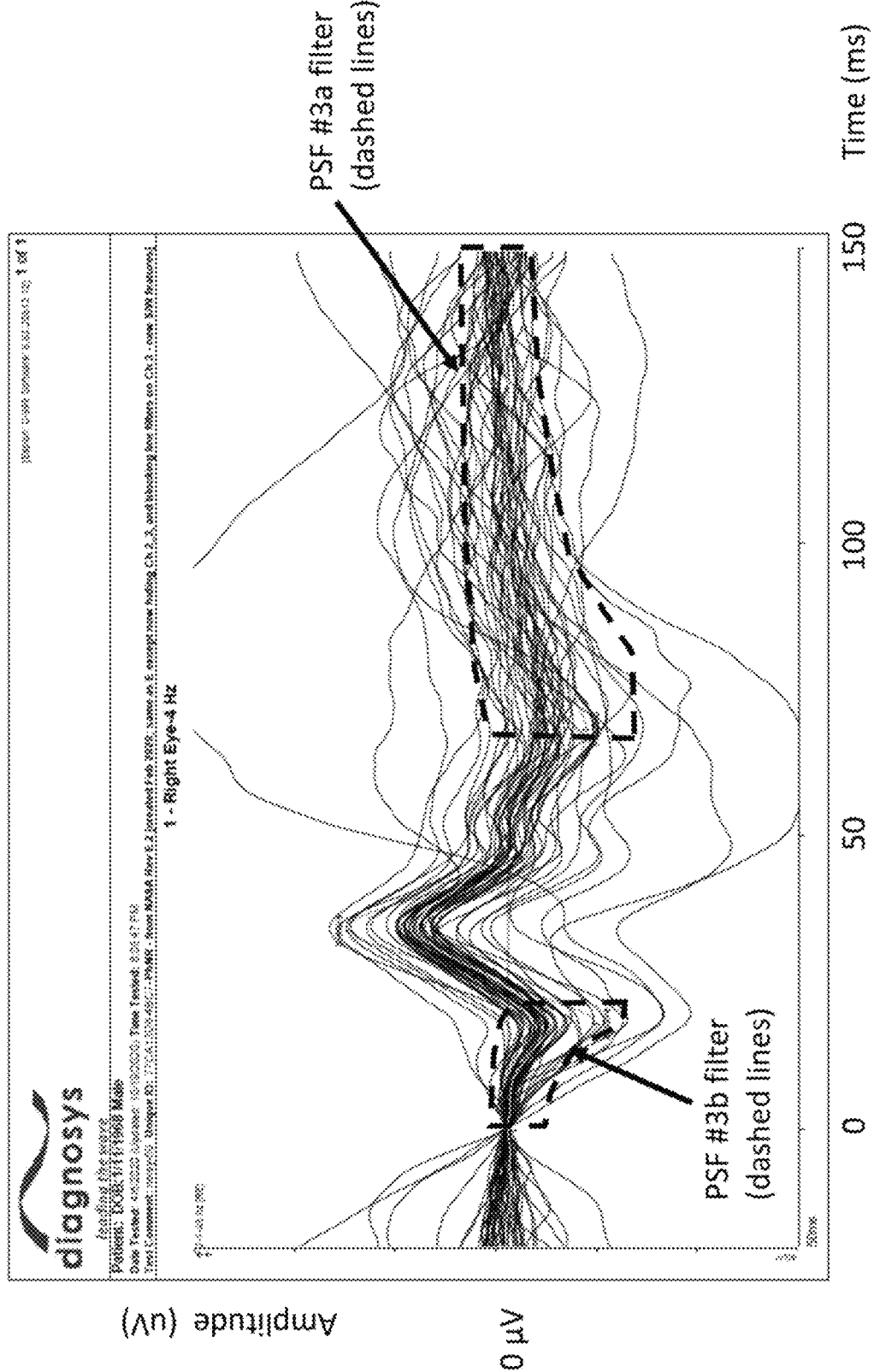

FIGS. 13*a* and 13*b* show yet another novel PSF 155 and a novel PSF 160 formed in accordance with the present invention. It will be appreciated that PSF 155 and PSF 160 may be used alone or in combination with one another. PSF 155 and/or PSF 160 may also be used in concert with a standard blink artifact rejection filter 165 (the dotted line box), as shown in FIG. 13*a*, or without standard blink artifact rejection filter 165, as shown in FIG. 13*b*. The primary difference between PSF 155 and PSF 130 (FIG. 11*a*) is that for PSF 155, the reject bars' amplitude levels vary non-linearly (and differently at the top and the bottom levels) across the time that is being evaluated by the filter, as shown in FIGS. 13*a* and 13*b*.

In addition to the foregoing, it should also be appreciated that the shape (i.e., timing and amplitude) of a PSF (e.g., the aforementioned PSFs 155, 160) may be determined dynamically during a test based on characteristics of the PhNR or ERG recording which are not generally affected by eye artifacts, namely, the a-wave and b-wave responses. By way of example but not limitation, the start timing of the PSF can be based on the timing of the peak a-wave, b-wave or some combination of the two. In addition (or alternatively), the amplitude cut-offs of the PSF can be based on a factor of the peak a-wave, b-wave or some combination of the two, in either a linear or non-linear shape that is scaled from the a-wave/b-wave information. This can be implemented to occur dynamically during the test or in post-analysis of the recording obtained during the test.

Figure 14:
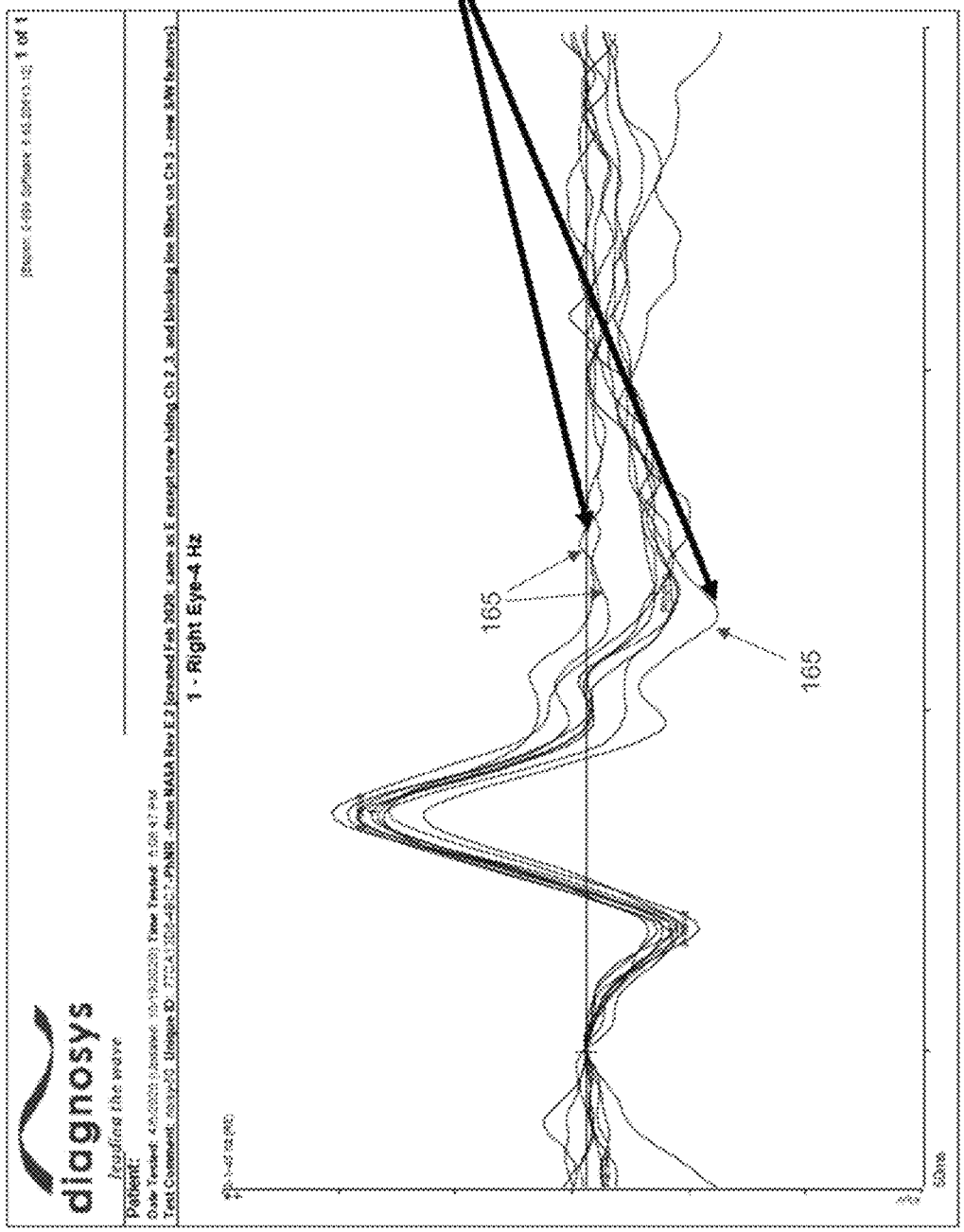
FIG. 14 shows another novel Preferred Sweep Filter (PSF) technique performed in accordance with the present invention.

FIG. 14 depicts the concept of another novel PSF technique (labeled "PSF #4" in FIG. 14) formed in accordance with the present invention. With the novel PSF technique depicted in FIG. 14, the root mean square (RMS) difference of each sweep (along the entire length of the sweep) is compared to the average of all sweeps as calculated at each time a data point is recorded (e.g., every 0.25, 0.5 or 1 millisecond). This can be done in any time window, including the full recording, or for a sub-set of the recording. The calculation then enables the ranking of each sweep according to how far, or close, it is to the average of all sweeps. Then, an arbitrary number of the "worst" sweeps (i.e., those sweeps which are not considered to be close to the average of all sweeps as determined by the aforementioned ranking) can be eliminated, thereby improving the repeatability of the remaining set of sweeps. FIG. 14 shows the test results from the test depicted in FIG. 9*d* after PSFs 110, 115 are applied, with the remaining 9 sweeps, and highlights three sweeps 165 that are the remaining "outlier" sweeps. Those three sweeps 165 can be objectively eliminated using "PSF #4" (i.e., the approach discussed above) with a time window of 50 to 150 ms, and a method choice to remove the "worst" 33% of remaining sweeps, which will eliminate 3 of the 9 sweeps based on the RMS criteria. Variations of PSF #4 include different time windows to be set (anywhere from time=0 to the end of the recording or anywhere in between), as well as various % of amounts of sweeps that can be removed (from 1% to 99%). Additionally, "PSF #4" can be used on its own.

EHPF and PSF Used in Combination

If desired, the EHPF and PSF discussed above can also be applied in combination with one another. By way of example but not limitation, any of the exemplary test results shown in FIGS. 6*a*-14 are tests which can have both EHPF and PSF applied in combination with one another. Combinations of the EHPF and PSF further strengthen the ability to remove eye artifacts.

Figure 15:
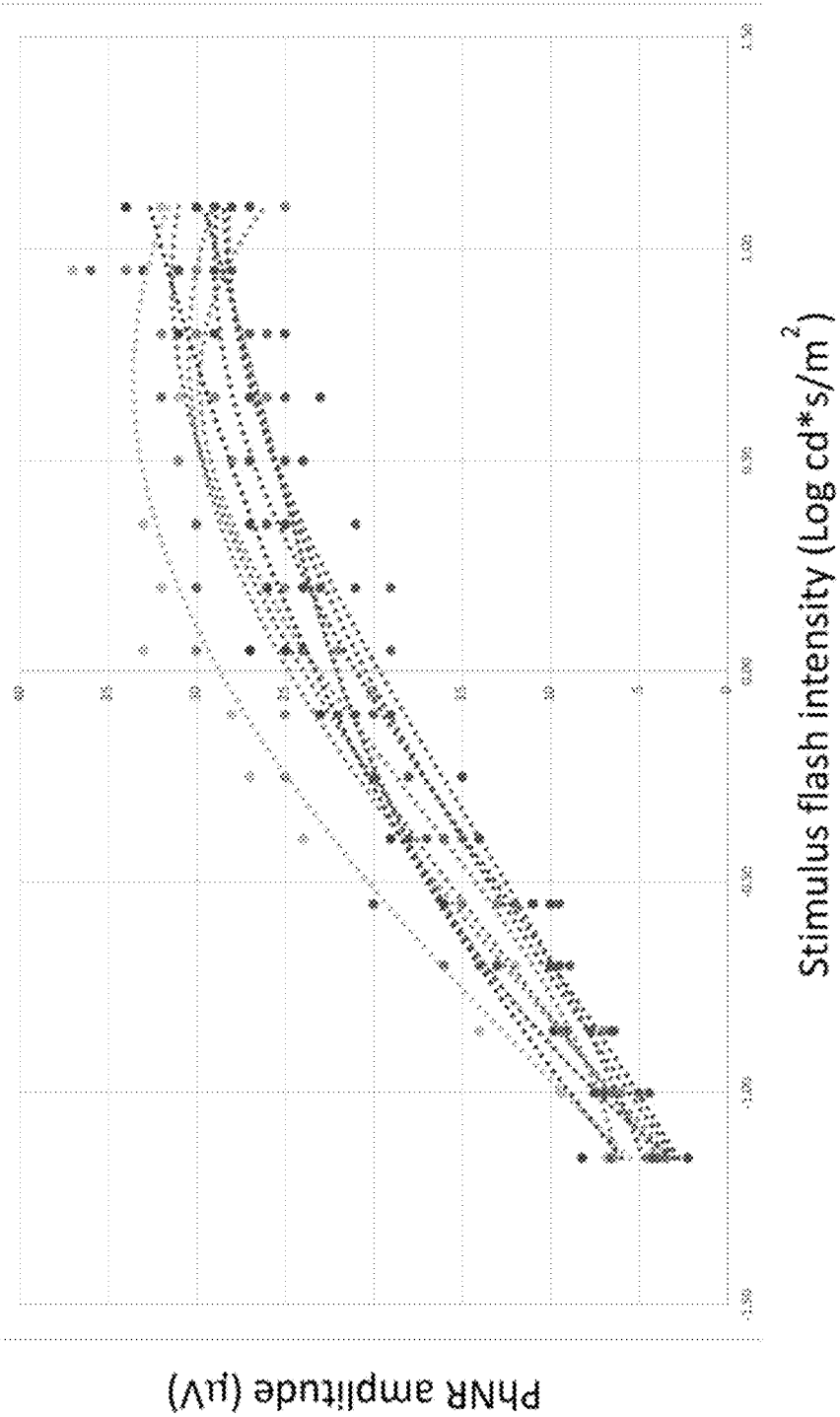
FIG. 15 shows the results of a PhNR intensity series using typical ISCEV international recording standards, including standard filter settings.

A commonly-used PhNR test records PhNR measurements in response to various stimulus flash intensities and plots the resulting PhNR peak amplitudes from each flash intensity on a graph. Various characteristics of the resulting plot can then be analyzed and a curve fit of the data can be generated to summarize those curves with fitting parameters. FIG. 15 shows a PhNR intensity series using typical ISCEV international recording standards, including standard filter settings (i.e., without application of the EHPF or PSF of the present invention). Each point on the graph represents a PhNR peak measurement (which, in turn, is itself the average of 50 sweeps recorded), with the PhNR peak amplitude plotted on the y-axis (in $\mu V$ units) and the flash intensity plotted on the x-axis (in Log cd*s/$m^2$ units). Each dotted line curve on the graph represents one set of PhNR measurements which were made at the flash intensities from −1.15 to +1.10 Log cd*s/$m^2$. Using the ISCEV standard filters, other than the general trend of increasing PhNR amplitudes with increasing flash intensities, there is little other information to be obtained from the tests (and very little apparent repeatability to the tests). For some of the test series, there is a peak PhNR amplitude and then decreasing PhNR amplitude with the highest flash intensities, which generally is expected from other similar tests, but that is not the case for all test series in this case. Even though this set of tests was conducted with the very best equipment and methods, as well as on a well-trained subject who was attempting to minimize their eye artifacts, the tests appear to be not very repeatable (nor "clean" in terms of a retinal response).

Figure 16:
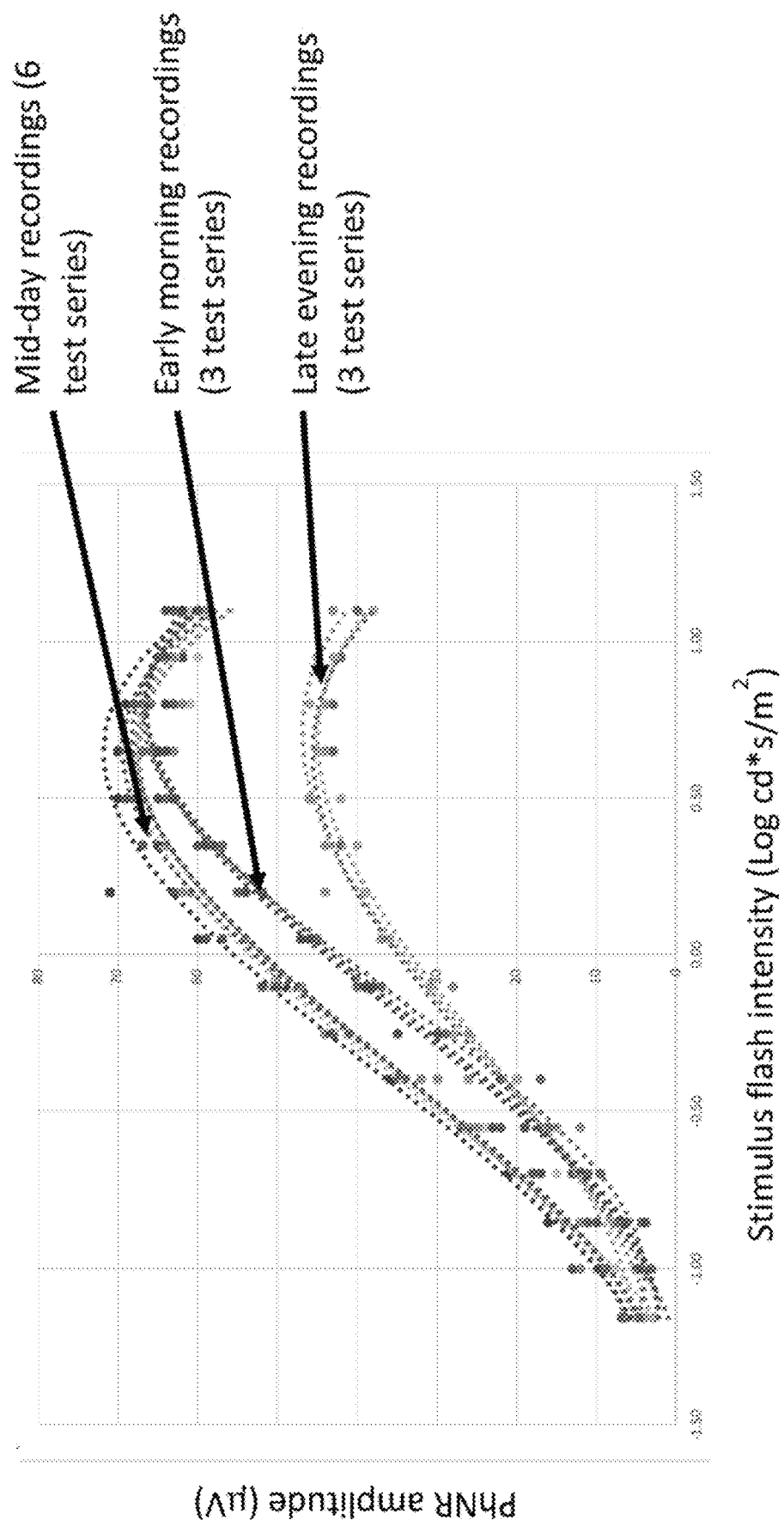
FIG. 16 shows the series of FIG. 15 after application of an Elevated High Pass Filter (EHPF) and a Preferred Sweep Filter (PSF) formed in accordance with the present invention.

FIG. 16 shows the same set of 12 tests as were plotted in FIG. 15, but in this case an EHPF (at 5 hz) formed in accordance with the present invention and a PSF (70 to 150 ms; +10 to −50 $\mu V$) formed in accordance with the present invention have been applied. After applying these novel filters, some very interesting trends and groupings may be observed. It is commonly known that functional responses of the retina can vary in repeatable ways across the day (e.g., as with other aspects of human physiology). It is interesting to note the pattern of the groupings depicted in FIG. 16: three test series were conducted in the late evening; three test series were conducted in early morning; and six test series were conducted in the middle of the day. Each of these align with each other (i.e., group together) very well, and are quite repeatable. These trends and repeatability were not apparent until applying the novel EHPF and the novel PSF formed in accordance with the present invention.

Benefits of Test-to-Test Repeatability Using the PSF

Figures 17A, 17B:
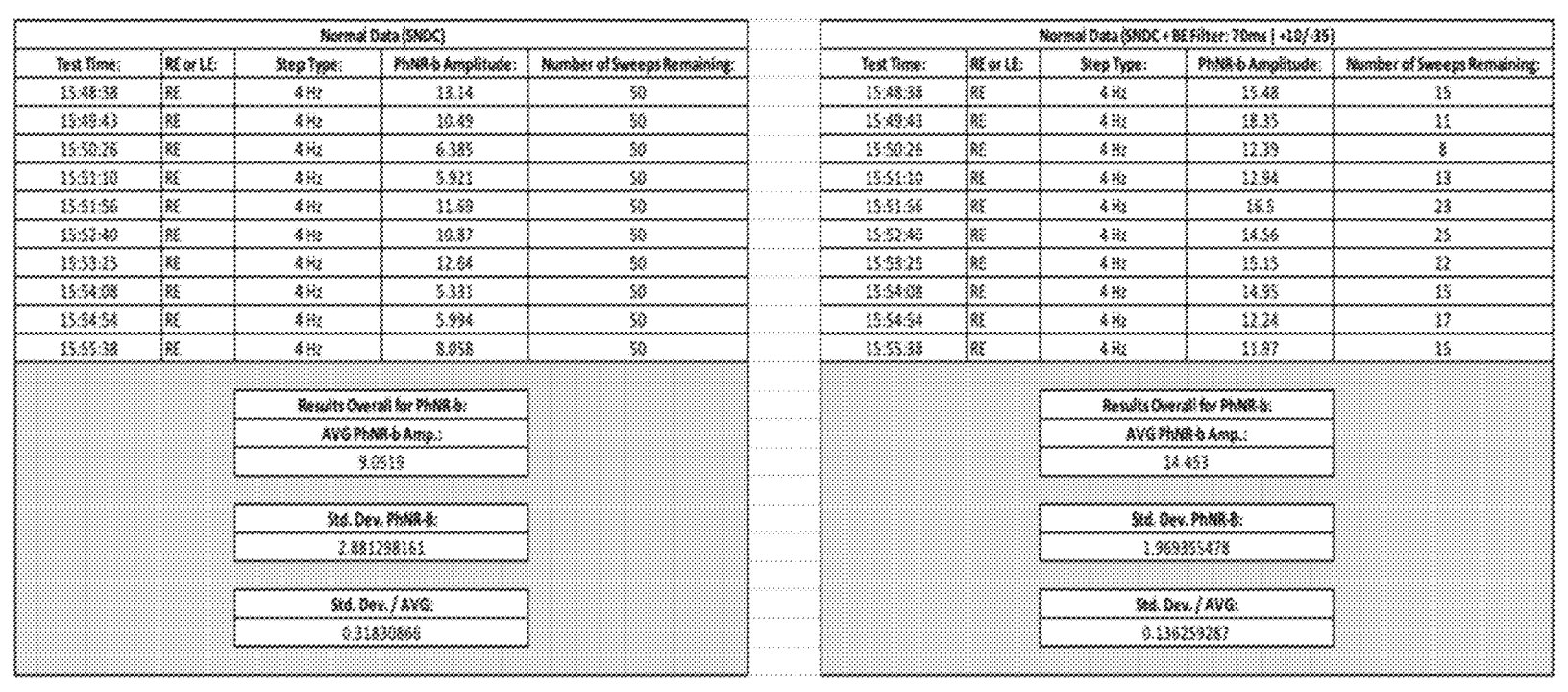
Figures 18A, 18B:
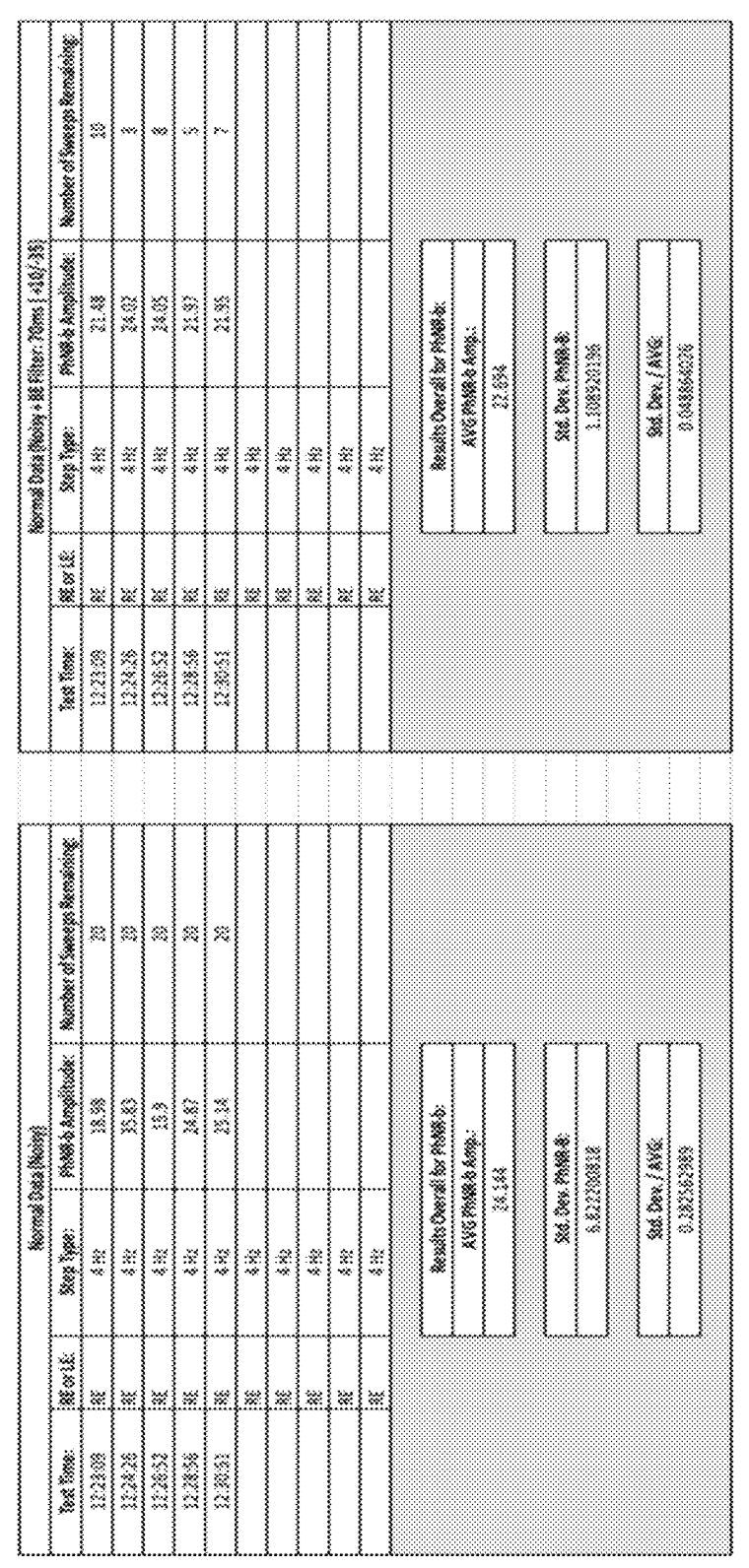

FIGS. 17*a*, 17*b*, 18*a* and 18*b* show the benefits of test-to-test repeatability that result from using the PSF of the present invention. In each test, a human subject was given ten (FIGS. 17a and 17b) and five (FIGS. 18a and 18b) PhNR tests using standard techniques. In FIGS. 17a and 18a, the test results using standard ISCEV filter techniques are summarized and the standard deviation divided by the average PhNR is calculated. FIGS. 17b and 18b show the same test results after a PSF (70 to 150 ms, +10 to −35 µV) formed in accordance with the present invention was applied. In case 1 (i.e., the results listed in FIGS. 17a and 17b), the test-to-test repeatability, as measured by PhNR standard deviation/average, went from 31.8% to 13.6%, a greater than twofold improvement in repeatability when using the PSF of the present invention in post-analysis. In case 2 (i.e., the results listed in FIGS. 18a and 18b), the test-to-test repeatability went from 28.3% to 4.9%, a greater than fivefold improvement in repeatability when using the PSF of the present invention in post-analysis.

Eye Artifacts which can be Used to Determine EHPF or PSF Filtering

Finally, if desired, techniques can be applied during an ERG test to gather further information about eye artifacts which can then be used to determine if an EHPF and/or PSF formed in accordance with the present invention is to be used (i.e., either during the test or in post-analysis of the test results) and, if such a filter is to be used, what type of PSF should be applied and the parameters of the filter. By way of example but not limitation, the PSF (and/or EHPF) of the present invention may not be applied, may be applied to a subset of sweeps or may be applied to all sweeps (either during the test or in post-analysis of the test results). Vision technology utilizing cameras, or other imaging devices such as infrared or LiDAR sensors, mounted near the stimulus, pointing at the subject's eyes, as well as algorithms to detect and record when an eye artifact occurs during the test, can be used to determine use of the EHPF and/or PSF of the present invention.

Figure 19:
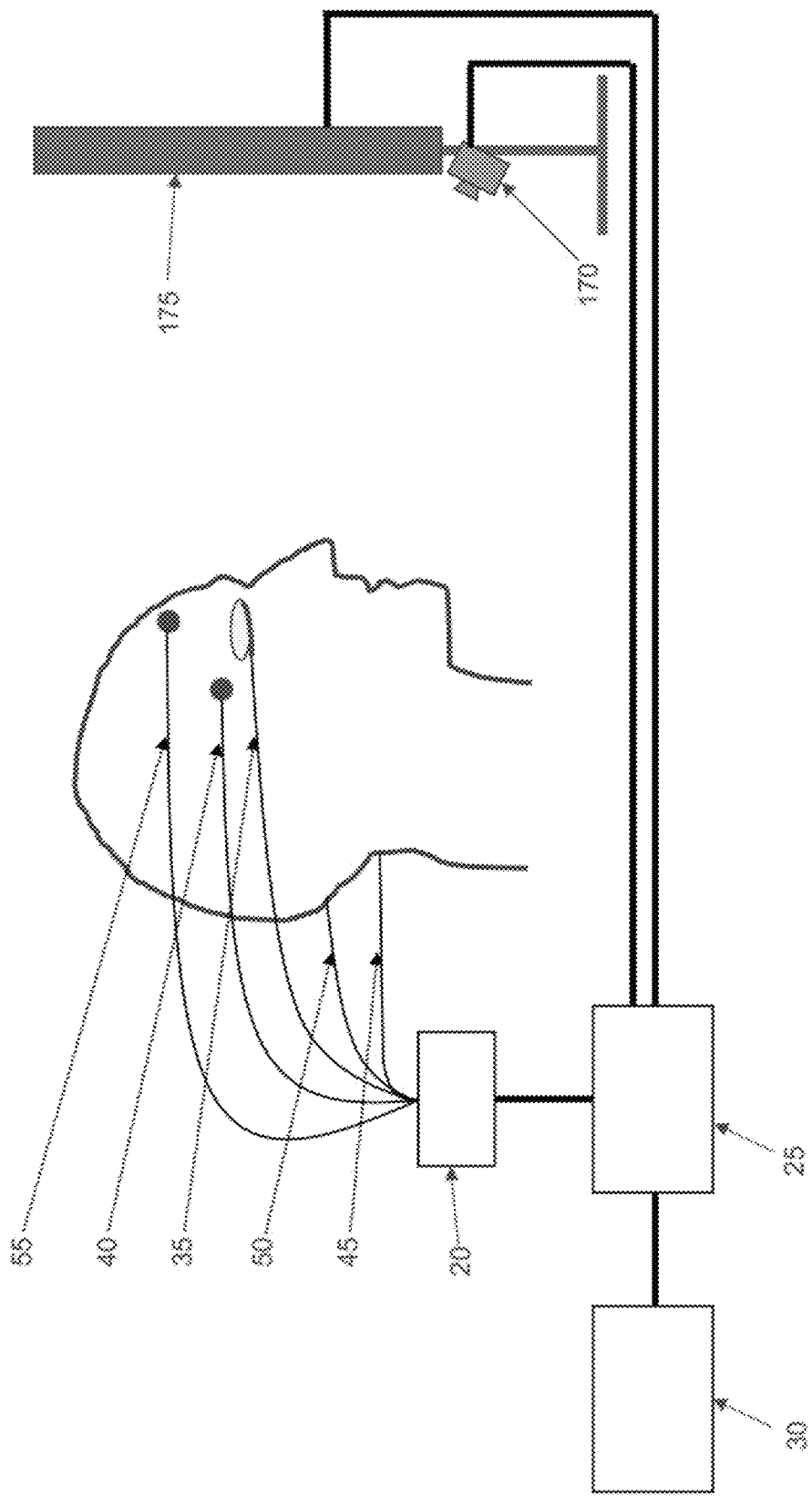
FIGS. 19 and 20 are schematic views showing a novel system formed in accordance with the present invention, wherein the system comprises at least one camera for tracking the test subject's eye and eyelid movement during performance of an ERG test.
Figure 20:
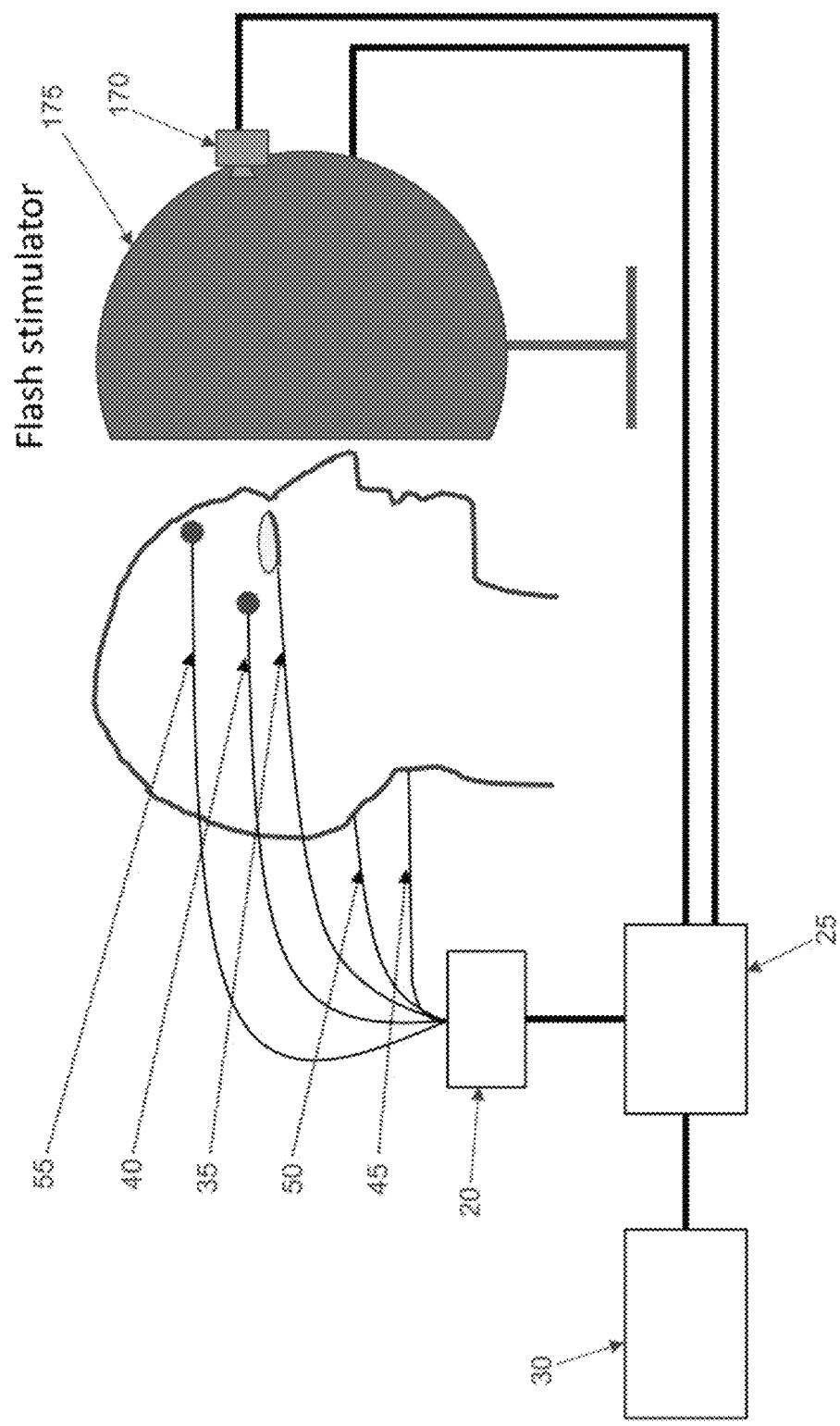

More particularly, and looking now at FIGS. 19 and 20, there is shown a camera 170 mounted to a display 175 (e.g., a monitor) configured to deliver a stimulus to a test subject. However, it should be appreciated that camera 170 may be located in any position offering a good view of the test subject's eyes and eye lids during the test (while not interfering with the stimulus in a way that would negatively impact the test results by blocking too much of the stimulus). Vision technology further enables use of the EHPF and/or PSF of the present invention during the test to immediately reject sweeps or, in post-analysis, to filter the sweeps either in time and/or frequency space.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for removing artifacts from an electroretinogram, the method comprising:
visually stimulating at least one eye of a test subject, and using at least two electrodes to measure electrical responses from the at least one eye of the test subject;
recording the electrical responses during, and for a predetermined period of time after, the time at which one or more visual stimuli are applied, whereby to generate a data set, wherein each electrical response is represented as a sweep comprising a plurality of voltage amplitude values and a plurality of corresponding time values;
plotting the voltage amplitude values of the data set on a first axis of an electroretinogram, and plotting the time values of the data set on a second axis of the electroretinogram, so as to produce a electroretinogram comprising a plurality of sweeps, wherein each sweep is defined to start at the time of a stimuli and generally represents a combination of signal components from (i) the electrical response of the retina of the at least one eye of the test subject to the visual stimulation, and (ii) an artifact;
identifying a zone of the electroretinogram plot defined by a predetermined upper voltage amplitude limit, a predetermined lower voltage amplitude limit, a predetermined start time limit, and a predetermined end time limit, with at least one of the voltage amplitude limits being smaller than the largest voltage amplitude value representing a recorded electrical response of the retina;
removing sweeps having voltage amplitude values that do not fall within the zone, whereby to produce a filtered electroretinogram depicting the sweeps not removed.

2. A method according to claim 1 further comprising:
applying an elevated high pass filter to each sweep, wherein the elevated high pass filter is configured to remove any signal components with a frequency value of <1 hz; and
plotting the resulting data set as an electroretinogram, in which the plurality of voltage amplitude values of the remaining signal is plotted on a first axis of an electroretinogram, and the plurality of corresponding time values of the remaining signal is plotted on a second axis of the electroretinogram.

3. A method according to claim 2 wherein the elevated high pass filter is applied to a group of averaged sweeps.

4. A method according to claim 2 wherein the elevated high pass filter is configured to remove any signal components with a frequency value of <5 hz.

5. A method according to claim 2 wherein the elevated high pass filter is configured to remove any signal components with a frequency value of <7 hz.

6. A method according to claim 2 wherein the elevated high pass filter comprises an analog filter.

7. A method according to claim 6 wherein the analog filter comprises one selected from the group consisting of a Bessel filter, a Butterworth filter, and a Chebyshev filter.

8. A method according to claim 2 wherein the elevated high pass filter comprises a Fourier filter.

9. A method according to claim 1 wherein the time over which the electroretinography is recorded is 150 milliseconds after each visual stimulus.

10. A method according to claim 1 wherein the electroretinogram comprises at least 50 sweeps.

11. A method according to claim 1 wherein at least one of the predetermined upper voltage amplitude limit of the zone, and the predetermined lower voltage amplitude limit of the zone varies as a function of time.

12. A method according to claim 11 wherein plotting the predetermined upper voltage amplitude limit of the zone and the predetermined lower voltage amplitude limit of the zone as a function of time results in the zone having an oval shape.

13. A method according to claim 1 wherein, before the step of identifying a zone of the electroretinogram defined by a predetermined upper voltage amplitude limit, a predetermined lower voltage amplitude limit, a predetermined start time limit, and a predetermined end time limit, a blink artifact rejection filter is applied to the electroretinogram in order to remove (i) any sweeps that have a voltage amplitude larger than +250 μV, and (ii) any sweeps that have a voltage amplitude smaller than −250 μV.

14. A method according to claim 1 wherein the predetermined upper voltage amplitude limit of the zone is +10 μV, the predetermined lower voltage amplitude limit of the zone is −50 μV, the predetermined start time limit of the zone is 70 milliseconds, and the predetermined stop time limit of the zone is 150 milliseconds.

15. A method according to claim 1 wherein at least one of the predetermined upper voltage amplitude limit of the zone, and the predetermined lower voltage amplitude limit of the zone varies linearly as a function of time.

16. A method according to claim 15 wherein plotting the predetermined upper voltage amplitude limit and the predetermined lower voltage amplitude limit as a function of time results in a zone having the shape of a parallelogram.

17. A method according to claim 1 wherein at least one of the predetermined start time limit of the zone, and the predetermined end time limit of the zone varies linearly as a function of voltage amplitude.

18. A method according to claim 17 wherein plotting the predetermined start time limit and the predetermined end time limit as a function of voltage amplitude results in a zone having the shape of a parallelogram.

19. A method according to claim 1 further comprising:
calculating an average voltage amplitude value for the plurality of sweeps for each time value;
calculating the root mean square (RMS) difference between the voltage amplitude value of each sweep at each time value and the average voltage amplitude value for all of the plurality of sweeps for that time value;
ranking the root mean square (RMS) difference of each sweep based on the difference between the calculated root mean square (RMS) difference of each sweep at each time value and the average voltage amplitude value for the plurality of the sweeps for that time value; and
discarding those ranked sweeps that are ranked below a predetermined value relative to the remaining sweeps, whereby to produce an electroretinogram depicting the sweeps not discarded.

20. A system for removing artifacts from an electroretinogram, the system comprising:
apparatus configured to visually stimulate at least one eye of a test subject, and using at least two electrodes to measure electrical responses from the at least one eye of the test subject;
a processing unit configured to:
record the electrical responses during, and for a predetermined period of time after, the time at which one or more visual stimuli are applied, whereby to generate a data set, wherein each electrical response is represented as a sweep comprising a plurality of voltage amplitude values and a plurality of corresponding time values;
plot the voltage amplitude values of the data set on a first axis of an electroretinogram, and plot the time values of the data set on a second axis of the electroretinogram, so as to produce a electroretinogram comprising a plurality of sweeps, wherein each sweep is defined to start at the time of a stimuli and generally represents a combination of signal components from (i) the electrical response of the retina of the at least one eye of the test subject to the visual stimulation, and (ii) an artifact;
identify a zone of the electroretinogram plot defined by a predetermined upper voltage amplitude limit, a predetermined lower voltage amplitude limit, a predetermined start time limit, and a predetermined end time limit, with at least one of the voltage amplitude limits being smaller than the largest voltage amplitude value representing a recorded electrical response of the retina;
remove sweeps having voltage amplitude values that do not fall within the zone, whereby to produce a filtered electroretinogram depicting the sweeps not removed.

21. A system according to claim 20 wherein the processing unit is further configured to:
apply an elevated high pass filter to each sweep, wherein the elevated high pass filter is configured to remove any signal components with a frequency value of <1 hz; and
plot the resulting data set as an electroretinogram, in which the plurality of voltage amplitude values of the remaining signal is plotted on a first axis of a electroretinogram, and the plurality of corresponding time values of the remaining signal is plotted on a second axis of the electroretinogram.

22. A system according to claim 21 wherein the elevated high pass filter is applied to a group of averaged sweeps.

* * * * *